United States Patent [19]
Conneely et al.

[11] Patent Number: 5,571,697
[45] Date of Patent: Nov. 5, 1996

[54] EXPRESSION OF PROCESSED RECOMBINANT LACTOFERRIN AND LACTOFERRIN POLYPEPTIDE FRAGMENTS FROM A FUSION PRODUCT IN ASPERGILLUS

[75] Inventors: Orla M. Conneely, Houston, Tex.; Denis R. Headon, Galway, Ireland; Bert W. O'Malley, Houston, Tex.

[73] Assignee: Baylor College of Medicine Texas Medical Center, Houston, Tex.

[21] Appl. No.: 303,009

[22] Filed: Nov. 2, 1994

Related U.S. Application Data

[63] Continuation-in-part of Ser. No. 145,681, Oct. 28, 1993, and a continuation of Ser. No. 250,308, May 27, 1994, which is a continuation-in-part of Ser. No. 873,304, Apr. 24, 1992, abandoned, said Ser. No. 145,681, is a continuation-in-part of Ser. No. 967,947, Oct. 27, 1992, abandoned, which is a continuation of Ser. No. 348,270, May 5, 1989, abandoned.

[51] Int. Cl.$^6$ .......................... C07K 14/79; C12N 15/12; C12N 15/62; C12N 15/80
[52] U.S. Cl. .......................... 435/69.7; 530/300; 530/395; 530/412; 530/400; 435/254.3; 435/320.1; 536/23.4; 536/23.5; 536/23.74; 536/24.1; 935/10; 935/11; 935/27; 935/47; 935/51; 935/68
[58] Field of Search .................. 424/439; 514/6; 435/69.7, 172.3, 252.3, 254.11, 254.21, 254.23, 254.3, 320.1; 530/350, 400, 412, 300, 395; 536/23.4, 23.5, 23.74, 24.1

[56] References Cited

U.S. PATENT DOCUMENTS

| | | | |
|---|---|---|---|
| 4,652,639 | 3/1987 | Stabinsky | 435/91.52 |
| 4,703,008 | 10/1987 | Lin | 435/240.2 |
| 4,710,465 | 12/1987 | Weissman et al. | 435/6 |
| 4,766,075 | 8/1988 | Goeddel et al. | 435/240.2 |
| 4,886,747 | 12/1989 | Derynck et al. | 435/69.4 |
| 4,959,318 | 9/1990 | Foster et al. | 435/172.3 |
| 4,965,190 | 10/1990 | Woo et al. | 435/6 |
| 5,019,508 | 5/1991 | Johnson et al. | 435/198 |
| 5,081,227 | 1/1992 | Millan | 530/328 |
| 5,304,633 | 4/1994 | Tomita et al. | 530/326 |

FOREIGN PATENT DOCUMENTS

| | | | |
|---|---|---|---|
| WO91/05045 | 4/1991 | WIPO . | |
| WO91/13982 | 9/1991 | WIPO | 530/400 |

OTHER PUBLICATIONS

Reid, K. B. M., Biochemical Journal, vol. 231, "Molecular cloning and characterization of the complementary DNA and gene coding for the B-chain of the subcomponent C1q of the human complement system", pp. 729–735. 1985.

Fortkamp, E., et al., DNA, vol. 5, No. 6, "Cloning and Expression in *Escherichia coli* of a Synthetic DNA for Hirudin, the Blood Coagulation Inhibitor in the Leech", pp. 511–517. 1986.

Wei, X., et al., Blood, vol. 72, No. 5, "Characterization of the complete cDNA sequence of human neutrophil lactoferrin and isolation of genomic clones", Supplement 1, p. 155a, Abstract 530. 1988.

(List continued on next page.)

*Primary Examiner*—Robert A. Wax
*Assistant Examiner*—William W. Moore
*Attorney, Agent, or Firm*—Albert P. Halluin; Pennie & Edmonds

[57] ABSTRACT

The subject invention provides for the production of lactoferrins and lactoferrin polypeptide fragments using the host cells Aspergillus in combination with novel plasmid constructs. More specifically, the subject invention provides novel vector constructs capable of producing lactoferrins and lactoferrin polypeptide fragments in Aspergillus host cells. More particularly, the subject invention provides for novel plasmid constructs suitable for use with Aspergillus and especially *Aspergillus awamori, niger* and *oryzae* host cells, which enables them to produce large amounts of recombinant lactoferrins and lactoferrin polypeptide fragments.

74 Claims, 60 Drawing Sheets

OTHER PUBLICATIONS

Anderson, B. F., et al., Proceedings of the National Academy of Sciences, U.S.A., vol. 84, "Structure of human lactoferrin at 3.2-A resolution", pp. 1769–1773. 1987.

Goodman, R. E., et al., Biochemical and Biophysical Research Communications, vol. 180, No. 1, "Bovine Lactoferrin mRNA: Sequence, Analysis, and Expression in the Mammary Gland", pp. 75–84. 1991.

LeGrand, D., et al., Biochimica et Biophysica Acta, vol. 787, No. 1, "Characterization and Localization of an Iron-binding 18-kDa Glycopeptide Isolated from the N-Terminal Half of Human Lactotransferrin", pp. 90–96. 1984.

Teng, C. T., et al., Somatic Cell and Molecular Genetics, vol. 13, No. 6, "Assignment of the Lactotransferrin Gene to Human Chromosome 3 and to Mouse Chromosome 9", pp. 689–693. 1987.

Campbell, T., et al., British Journal of Cancer, vol. 65, No. 1, "Isolation of a lactoferrin cDNA clone and its expression in human breast cancer", pp. 19–26. 1992.

Shirsat, N. V., et al., Gene, vol. 110, "Structure of the murine lactotransferrin gene is similar to the structure of other transferrin-encoding genes and shares a putative regulatory region with the murine myeloperoxidase gene", pp. 229–234. 1992.

Cunningham, G. A., et al., Biochemical and Biophysical Research Communications, vol. 189, No. 3, "Structural Organization of the Mouse Lactoferrin Gene", pp. 1725–1731. 1992.

Mount, S. M., Nucleic Acids Research, vol. 10, No. 2, "A catalogue of splice junction sequences", pp. 459–472. 1982.

Jeenes, David J. et al. "A truncated glucoamylase gene fusion for heterologous protein secretion from *Aspergillus niger*". *FEMS Microbiology Letters* 107: 267–272 (1993).

Ward, Michael et al. "Improved Production Of Chymosin In *Aspergillus* By Expression as a Glucoamylase–Chymosin Fusion". *Bio/Technology* 8: 435–440 (1990).

Vilja, Pekka et al. "A Rapid and Sensitive Non–Competitive Avidin–Biotin Assay for Lactoferrin". *Journal of Immunological Methods* 76: 73–83 (1985).

Ward, Pauline P. et al. "An inducible expression system for the production of human lactoferrin in *Aspergillus nidulans*". *Gene* 122: 219–223 (1992).

Bellamy W. et al. "Antibacterial spectrum of lactoferricin B, a potent bactericidal peptide derived from the N–terminal region of bovine lactoferrin". *Journal of Applied Bacteriology* 73: 472–479 (1992).

Alexander, L. J. et al. "Cloning and sequencing of the porcine lactoferrin cDNA". *Animal Genetics* 23: 251–256 (1992).

Rey, Michael W. et al. "Complete nucleotide sequence of human mammary gland lactoferrin". *Nucleic Acids Research* 18(17): 5288 (1990).

Johnston, Jennifer J. et al. "Correlation of Messenger RNA levels With Protein Defects in Specific Granule Deficiency". *Blood* 80(8): 2088–2091 (1992).

Mead, P. E. and Tweedie, J. W. "DNA and protein sequence of bovine lactoferrin". *Nucleic Acids Research* 18(23): 7167 (1990).

Stowell et al. "Expression of cloned human lactoferrin in baby–hamster kidney cells". *Biochem. J.* 276: 349–355 (1991).

Soukka, Tero et al. "Fungicidal effect of human lactoferrin against *Candida albicans*". *FEMS Microbiology Letters* 90: 223–228 (1992).

Christensen, Tove et al. "High Level Expression of Recombinant Genes in *Aspergillus Oryzae*". *Bio/Technology* 6: 1419–1422 (1988).

Metz–Boutigue, Marie–Helene et al. "Human lactotransferrin: amino acid sequence and structural comparisons with other transferrins". *European Journal of Biochemistry* 145: 659–676 (1984).

Bellamy, Wayne et al. "Identification of the bactericidal domain of lactoferrin". *Biochimica et Biophysica Acta.* 1121: 130–136 (1992).

Valenti, Piera et al. "Interaction between lactoferrin and ovotransferrin and *Candida* cells". *FEMS Microbiology Letters* 33: 271–275 (1986).

Rado, Thomas A. et al. "Isolation of Lactoferrin cDNA From a human Myeloid Library and Expression of mRNA During Normal and Leukemic Myelopoiesis". *Blood* 70(4): 989–993 (1987).

Pierce, Annick et al. "Molecular cloning and sequence analysis of bovine lactotransferrin". *European Journal of Biochemistry* 196: 177–184 (1991).

Lydon, John P. et al. "Nucleotide and primary amino acid sequence of porcine lactoferrin". *Biochem. Biophys. Acta.*: 97–99 (1992).

Powell, M. J. and Ogden, J. E. "Nucleotide sequence of human lactoferrin cDNA". *Nucleic Acids Research* 18(13): 4013 (1990).

Epstein, J. B. et al. "Oral Candidiasis: Pathogenesis and Host Defense". *Reviews of Infectious Diseases* 6(1): 96–106 (1984).

Panella, Timothy J. et al. "Polymorphism and Altered Methylation of the Lactoferrin Gene in Normal Leukocytes, Leukemic Cells, and Breast Cancer". *Cancer Research* 51: 3037–3043 (1991).

Ward, Pauline P. et al. "Production of Biologically Active Recombinant Human Lactoferrin In *Aspergillus Oryzae*". *Bio/Technology* 10: 784–789 (1992).

Huge–Jensen, Birgitte et al. "*Rhizomucor miehei* Triglyceride Lipase Is Processed and Secreted from Transformed *Aspergillus oryzae*". *Lipids* (24)9: 781–785 (1989).

Hutchens, T. William et al. "Structurally intact (978–kDa) forms of maternal lactoferrin purified from urine of preterm infants fed human milk: Identification of a trypsin–like proteolytic cleavage event in vivo that does not result in fragment dissociation". *Proceedings of the National Academy of Sciences, USA* 88: 2994–2998 (1993).

Figure 4

- natural human lactoferrin gene construct:

LF signal seq. --- Cys Leu Ala | Gly Arg Arg Arg Arg Ser Val Gln Trp Cys → mature natural human lactoferrin

- recombinant human lactoferrin gene construct in *A. awamori*:

glucoamy. gn. --- Ser Lys Arg* | Gly Arg Arg Arg Arg Ser Val Gln Trp Cys → mature recombinant human lactoferrin

*KEX-2 cleavage site

- rhLF N-terminal amino acid sequence:

Gly Arg Arg Arg Arg Ser Val Gln Trp Cys →

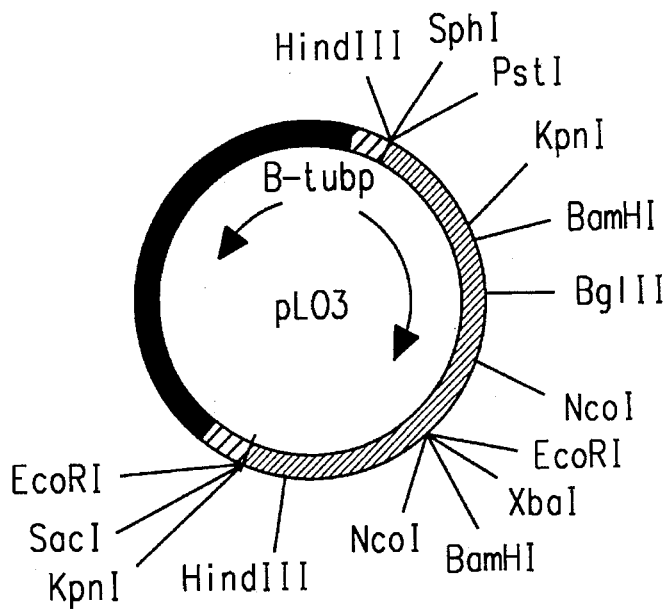
EcoRI SITES FILLED AND BLUNT LIGATED
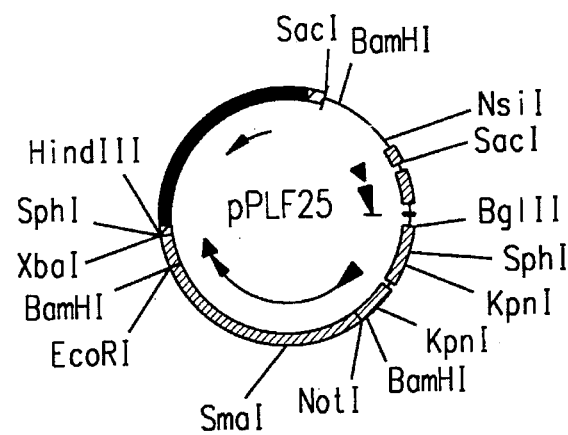
pPLF25 DIGESTED WITH HindIII
CONT. ON FIG.10C
FIG.10B FROM FIG.10B
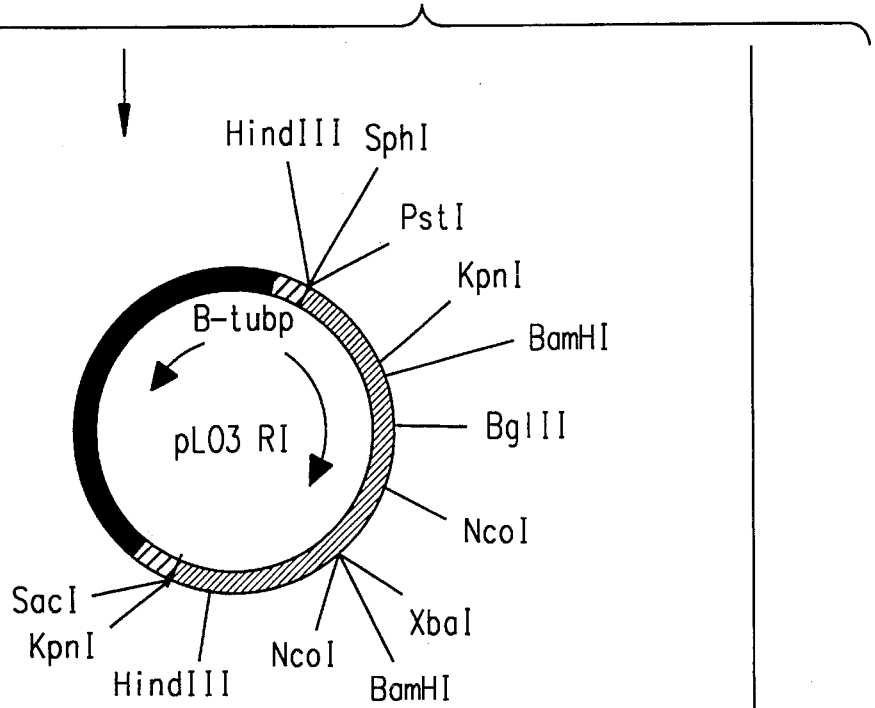
2.1 HindIII FRAGMENT ISOLATED; LIGATED TO pPLF25
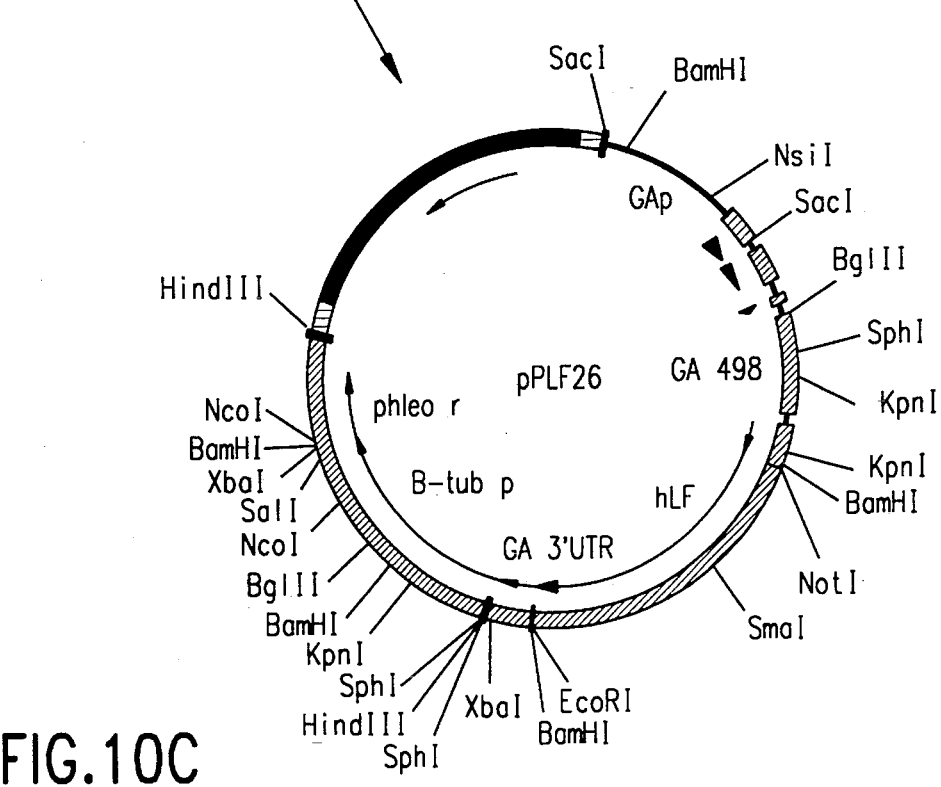
FIG.10C (Linear) MAPSORT of: hlf2 check: 7473 from: 1 to: 2360
Mismatch: 0 MinCuts = 1 MaxCuts: 10

AccI GT'mk_AC
Cuts at:     0    319    2360
  Size:       319   2041
AceIII CAGCTCnnnnnnn'nnnn_
Cuts at:     0    948    1125    2183    2219    2360
  Size:       948   177    1058    36     141
  Fragments arranged by size:
              1058   948    177    141    36
AhdI GACnn_n'nnGTC
Cuts at:     0    472    2360
  Size:       472   1888
AlwI GGATCnnnn'n_
Cuts at:     0    1341    1955    2360
  Size:       1341   614    405
  Fragments arranged by size:
              1341   614    405
AlwNI CAG_nnn'CTG
Cuts at:     0    1139    1913    2360
  Size:       1139   774    447
  Fragments arranged by size:
              1139   774    447
ApaI G_GGCC'C
Cuts at:     0    56    2360
  Size:       56    2304
ApaBI GCA_nnnnn'TGC
Cuts at:     0    1140    1789    2360
  Size:       1140   649    571
  Fragments arranged by size:
              1140   649    571
ApaLI G'TGCA_C
Cuts at:     0    101    2360
  Size:       101   2259
ApoI r'AATT_y
Cuts at:     0    1    930    1527    1932    2136    2318    2360
  Size:       1    929    597    405    204    182    42
  Fragments arranged by size:
              929    597    405    204    182    42    1

FIG. 13A

AvaI C'yCGr_G
Cuts at:    0    48    117    820    1010    1571    2360
  Size:    48    69    703    190    561    789
  Fragments arranged by size:
           789    703    561    190    69    48
AvaII G'GwC_C
Cuts at:    0    325    439    495    725    824    2067    2360
  Size:    325    114    56    230    99    1243    293
  Fragments arranged by size:
           1243    325    293    230    114    99    56
BanI G'GyrC_C
Cuts at:    0    657    1004    1298    1675    2360
  Size:    657    347    294    377    685
  Fragments arranged by size:
           685    657    377    347    294
BanII G_rGCy'C
Cuts at:    0    56    508    1521    2360
  Size:    56    452    1013    839
  Fragments arranged by size:
           1013    839    452    56
BbsI GAAGACnn'nnnn_
Cuts at:    0    20    2360
  Size:    20    2340
BbvI GCAGCnnnnnnnn'nnnn_
Cuts at:    0    168    394    528    1079    1126    1189    1780    1827
  Size:    168    226    134    551    47    63    591    47
Cuts at:    1827    1900    2360
  Size:    73    460
  Fragments arranged by size:
           591    551    460    226    168    134    73    63    47    47
Bce83I CTTGAGnnnnnnnnnnnnnn_nn'
Cuts at:    0    1088    1187    2360
  Size:    1088    99    1173
  Fragments arranged by size:
           1173    1088    99
BcefI ACGGCnnnnnnnnnnnn'n_
Cuts at:    0    62    343    823    1447    1670    1855    2360
  Size:    62    281    480    624    223    185    505
  Fragments arranged by size:
           624    505    480    281    223    185    62

FIG. 13B

BfaI C'TA_G
Cuts at:    0    952   1414   1834   2360
  Size:        952    462    420    526
  Fragments arranged by size:
               952    526    462    420
BfiI ACTGGG
Cuts at:    0   1664   2360
  Size:       1664    696
BglI GCCn_nnn'nGGC
Cuts at:    0    427    843   1807   2360
  Size:        427    416    964    553
  Fragments arranged by size:
               964    553    427    416
BglII A'GATC_T
Cuts at:    0    965   1575   2360
  Size:        965    610    785
  Fragments arranged by size:
               965    785    610
BmgI GkGCCC
Cuts at:    0    54   1007   1557   1631   2360
  Size:        54    953    550     74    729
  Fragments arranged by size:
               953    729    550     74     54
BpmI CTGGAGnnnnnnnnnnnnnnnn_nn'
Cuts at:    0    706   1714   2360
  Size:        706   1008    646
  Fragments arranged by size:
              1008    706    646
Bpu10I CC'TnA_GC
Cuts at:    0    502   1765   2188   2360
  Size:        502   1263    423    172
  Fragments arranged by size:
              1263    502    423    172
BsaWI w'CCGG_w
Cuts at:    0   1672   2360
  Size:       1672    688
BsaXI ACnnnnnCTCC
Cuts at:    0     87   1037   1268   2360
  Size:         87    950    231   1092
  Fragments arranged by size:
              1092    950    231     87

FIG. 13C

BsbI CAACAC
Cuts at:   0    778    2014    2227    2360
  Size:       778   1236    213     133
  Fragments arranged by size:
              1236    778    213    133
BscGI CCCGT
Cuts at:   0    324    494    681    1517    2360
  Size:       324    170    187    836    843
  Fragments arranged by size:
              843    836    324    187    170
BseRI GAGGAGnnnnnnnn_nn'
Cuts at:   0    617    1095    1181    2360
  Size:       617    478    86    1179
  Fragments arranged by size:
              1179    617    478    86
BsgI GTGCAGnnnnnnnnnnnnnnnn_nn'
Cuts at:   0    577    2360
  Size:       577    1783
BsiEI CG_ry'CG
Cuts at:   0    10    2360
  Size:       10    2350
BsiHKAI G_wGCw'C
Cuts at:   0    105    714    1592    2109    2360
  Size:       105    609    878    517    251
  Fragments arranged by size:
              878    609    517    251    105
BsmI GAATG_Cn'
Cuts at:   0    1694    2360
  Size:       1694    666
BsmAI GTCTCn'nnnn_
Cuts at:   0    187    670    682    1690    1882    2360
  Size:       187    483    12    1008    192    478
  Fragments arranged by size:
              1008    483    478    192    187    12
BsmBI CGTCTCn'nnnn_
Cuts at:   0    670    682    1690    2360
  Size:       670    12    1008    670
  Fragments arranged by size:
              1008    670    670    12
BsmFI GGGACnnnnnnnnnn'nnnn_
Cuts at:   0    338    479    614    762    810    2080    2360
  Size:       338    141    135    148    48    1270    280
  Fragments arranged by size:
              1270    338    280    148    141    135    48

FIG. 13D

Bsp24I GACnnnnnnTGGnnnnnnn_nnnnn'
Cuts at:    0     52    84    239    271    569    601    62    2094
  Size:    52    32    155    32    298    32    1461    32
Cuts at:  2094    2360
  Size:    266
  Fragments arranged by size:
         1461    298    266    155    52    32    3    32    32

Bsp1286I G_dGCh'C
Cuts at:    0    56    105    508    714    1009    1521    559    1592
  Size:    56    49    403    206    295    512    38    33
Cuts at:  1592    1633    2109    2360
  Size:    41    476    251
  Fragments arranged by size:
         512    476    403    295    251    206    56    49    41    38    33

BspMI ACCTGCnnnn'nnnn_
Cuts at:    0    1194    2360
  Size:    1194    1166

BsrI ACTG_Gn'
Cuts at:    0    206    789    1154    1667    1979    2360
  Size:    206    583    365    513    312    381
  Fragments arranged by size:
         583    513    381    365    312    206

BsrDI GCAATG_nn'
Cuts at:    0    220    1646    2360
  Size:    220    1426    714
  Fragments arranged by size:
         1426    714    220

BsrGI T'GTAC_A
Cuts at:    0    1273    2360
  Size:    1273    1087

BstXI CCAn_nnnn'nTGG
Cuts at:    0    942    1161    1256    2360
  Size:    942    219    95    1104
  Fragments arranged by size:
         1104    942    219    95

BstYI r'GATC_y
Cuts at:    0    965    1575    1947    2360
  Size:    965    610    372    413
  Fragments arranged by size:
         965    610    413    372

FIG. 13E

Bsu36I CC'TnA_GG
Cuts at:    0    2142    2360
  Size:    2142    218
CjeI ACnnnnnnTGGnnnnnnn'nnnnnn_
Cuts at:    0    79    188    266    563    618    2056 2360
  Size:    79    109    78    297    55    1438    304
  Fragments arranged by size:
          1438    304    297    109    79    78    55
CviRI TG'CA
Cuts at:    0    103    184    404    558    1216    1281    1476    1525
  Size:    103    81    220    154    658    65    195    49
Cuts at:    1525    1704    1730    2360
  Size:    179    26    630
  Fragments arranged by size:
          658    630    220    195    179    154    103    81
          65    49    26
DdeI C'TnA_G
Cuts at:    0    502    536    672    1684    1765    1828    2017    2142
  Size:    502    34    136    1012    81    63    189    125
Cuts at:    2142    2188    2297    2360
  Size:    46    109    63
  Fragments arranged by size:
          1012    502    189    136    125    109    81    63    63    46    34
DpnI GA'TC
Cuts at:    0    967    1348    1406    1577    1949    2360
  Size:    967    381    58    171    372    411
  Fragments arranged by size:
          967    411    381    372    171    58
DraIII CAC_nnn'GTG
Cuts at:    0    852    2020    2360
  Size:    852    1168    340
  Fragments arranged by size:
          1168    852    340
DsaI C'CryG_G
Cuts at:    0    358    1462    1492    1852    1870    2036    2360
  Size:    358    1104    30    360    18    166    324
  Fragments arranged by size:
          1104    360    358    324    166    30    18
EaeI y'GGCC_r
Cuts at:    0    74    523    2026    2360
  Size:    74    449    1503    334
  Fragments arranged by size:
          1503    449    334    74

FIG. 13F

EarI CTCTTCn'nnn_
Cuts at:    0    152   1509   2216   2360
   Size:       152   1357   707    144
   Fragments arranged by size:
               1357   707   152   144
EciI TCCGCC
Cuts at:    0    313    891   2360
   Size:       313    578   1469
   Fragments arranged by size:
               1469   578   313
Eco57I CTGAAGnnnnnnnnnnnnnnn_nn'
Cuts at:    0    432    629   2269   2360
   Size:       432    197   1640    91
   Fragments arranged by size:
               1640   432   197    91
EcoNI CCTnn'n_nnAGG
Cuts at:    0   1372   1905   2248   2360
   Size:      1372    533    343    112
   Fragments arranged by size:
               1372   533   343   112
EcoO109I rG'GnC_Cy
Cuts at:    0    52    53    725    824   2231   2360
   Size:       52     1    672     99   1407   129
   Fragments arranged by size:
               1407   672   129    99    52    1
EcoRI G'AATT_C
Cuts at:    0    1    2136   2360
   Size:        1   2135    224
   Fragments arranged by size:
               2135   224    1
EcoRV GAT'ATC
Cuts at:    0   1380   2360
   Size:      1380    980
FauI CCCGCnnnn'nn_
Cuts at:    0    590   1099   2360
   Size:       590    509   1261
   Fragments arranged by size:
               1261   590   509
FokI GGATGnnnnnnnnn'nnnn_
Cuts at:    0    189   460    882   1044   1272   1895   2252   2360
   Size:       189   271    422    162    228    623    357    108
   Fragments arranged by size:
               623   422   357   271   228   189   162   108

FIG. 13G

FspI TGC'GCA
Cuts at:    0    1143    2360
  Size:   1143    1217
GdiII y'GGCC_G
Cuts at:    0    74    2360
  Size:    74    2286
HaeI wGG'CCw
Cuts at:    0    123    219    280    430    525    2028    2360
  Size:   123    96    61    150    95    1503    332
  Fragments arranged by size:
          1503    332    150    123    96    95    61
HgiEII ACCnnnnnnGGT
Cuts at:    0    254    2360
  Size:   254    2106
HhaI G_CG'C
Cuts at:    0    1106    1144    1793    2360
  Size:   1106    38    649    567
  Fragments arranged by size:
          1106    649    567    38
Hin4I GAbnnnnnvTC
Cuts at:    0    471    727    1573    1578    1580    2263    2360
  Size:   471    256    846    5    2    683    97
  Fragments arranged by size:
          846    683    471    256    97    5    2
HinfI G'AnT_C
Cuts at:    0    195    881    981    1020    1862    2032    2360
  Size:   195    686    100    39    842    170    328
  Fragments arranged by size:
          842    686    328    195    170    100    39
HphI GGTGAnnnnnnn_n'
Cuts at:    0    380    916    1626    2360
  Size:   380    536    710    734
  Fragments arranged by size:
          734    710    536    380
MaeII A'CG_T
Cuts at:    0    691    1699    2360
  Size:   691    1008    661
  Fragments arranged by size:
          1008    691    661

FIG. 13H

MaeIII 'GTnAC_
Cuts at:   0    245    760    922   1149   1181   1338   1718   1823
  Size:    245    515    162    227    32    157    380    105
Cuts at: 1823   2360
  Size:   537
  Fragments arranged by size:
          537    515    380    245    227    162    157    105    32

MboII GAAGAnnnnnnn_n'
Cuts at:   0    20    169    383    524    876   1496   2170   2173
  Size:    20    149    214    141    352    620    674    3
Cuts at: 2173   2203   2360
  Size:    30    157
  Fragments arranged by size:
          674    620    352    214    157    149    141    30    20    3

MmeI TCCrACnnnnnnnnnnnnnnnnnnnn_nn'
Cuts at:   0    30   2360
  Size:    30   2330

MscI TGG'CCA
Cuts at:   0    525   2028   2360
  Size:    525   1503   332
  Fragments arranged by size:
          1503    525    332

MslI CAynn'nnrTG
Cuts at:   0    352   1461   2360
  Size:    352   1109   899
  Fragments arranged by size:
          1109    899    352

MspI C'CG_G
Cuts at:   0    553    821   1042   1097   1673   1959   2360
  Size:    553    268    221    55    576    286    401
  Fragments arranged by size:
          576    553    401    286    268    221    55

MspA1I CmG'CkG
Cuts at:   0    181    392    444    519    544   2360
  Size:    181    211    52    75    25    1816
  Fragments arranged by size:
          1816    211    181    75    52    25

NciI CC's_GG
Cuts at:   0    553    821    822   1097   1959   2360
  Size:    553    268    1    275    862    401
  Fragments arranged by size:
          862    553    401    275    268    1

FIG. 13I

NcoI C'CATG_G
Cuts at:    0    1492    1852    2036    2360
  Size:     1492    360    184    324
  Fragments arranged by size:
            1492    360    324    184
NdeI CA'TA_TG
Cuts at:    0    2051    2360
  Size:     2051    309
NlaIII _CATG'
Cuts at:    0    20    837    1253    1496    1762    1856    1869    2040
  Size:     20    817    416    243    266    94    13    171
Cuts at:    2040    2360
  Size:     320
  Fragments arranged by size:
            817    416    320    266    243    171    94    20    13
PleI GAGTCnnnn'n_
Cuts at:    0    189    975    2026    2360
  Size:     189    786    1051    334
  Fragments arranged by size:
            1051    786    334    189
Psp5II rG'GwC_Cy
Cuts at:    0    725    824    2360
  Size:     725    99    1536
  Fragments arranged by size:
            1536    725    99
PstI C_TGCA'G
Cuts at:    0    1283    1478    2360
  Size:     1283    195    882
  Fragments arranged by size:
            1283    882    195
PvuII CAG'CTG
Cuts at:    0    181    392    519    544    2360
  Size:     181    211    127    25    1816
  Fragments arranged by size:
            1816    211    181    127    25
RsaI GT'AC
Cuts at:    0    642    1032    1275    2360
  Size:     642    390    243    1085
  Fragments arranged by size:
            1085    642    390    243

FIG. 13J

SanDI GG'GwC_CC
Cuts at:    0    824    2360
  Size:      824   1536
SapI GCTCTTCn'nnn_
Cuts at:    0    1509   2216   2360
  Size:      1509   707    144
  Fragments arranged by size:
             1509   707    144
Sau3AI 'GATC_
Cuts at:    0    965   1346   1404   1575   1947   2360
  Size:      965   381    58    171    372    413
  Fragments arranged by size:
             965   413    381   372    171     58
SfaNI GCATCnnnnn'nnnn_
Cuts at:    0    230    860   1225   1235   2360
  Size:      230   630    365    10    1125
  Fragments arranged by size:
             1125   630    365   230     10
SfcI C'TryA_G
Cuts at:    0    304    460   1279   1474   2360
  Size:      304   156    819   195    886
  Fragments arranged by size:
             886   819    304   195    156
SmaI CCC'GGG
Cuts at:    0    822    2360
  Size:      822   1538
Sse8647I AG'GwC_CT
Cuts at:    0    725    2360
  Size:      725   1635
SspI AAT'ATT
Cuts at:    0    1539   2061   2360
  Size:      1539   522    299
  Fragments arranged by size:
             1539   522    299
StuI AGG'CCT
Cuts at:    0    280    430    2360
  Size:      280   150   1930
  Fragments arranged by size:
             1930   280    150
StyI C'CwwG_G
Cuts at:    0    1034   1492   1852   2036   2234   2360
  Size:      1034   458    360   184    198    126
  Fragments arranged by size:
             1034   458    360   198    184    126

FIG. 13K

TaqI T'CG_A
Cuts at:    0    999    1804    2360
  Size:    999    805    556
  Fragments arranged by size:
           999    805    556
TaqII GACCGAnnnnnnnnnn_nn'
Cuts at:    0    342    2360
  Size:    342    2018
TauI GCsGC
Cuts at:    0    310    380    2360
  Size:    310    70    1980
  Fragments arranged by size:
           1980    310    70
TfiI G'AwT_C
Cuts at:    0    881    1020    1862    2360
  Size:    881    139    842    498
  Fragments arranged by size:
           881    842    498    139
ThaI CG'CG
Cuts at:    0    1106    2360
  Size:    1106    1254
TseI GCwGC
Cuts at:    0    182    383    517    1093    1140    1178    1794    1841
  Size:    182    201    134    576    47    38    616    47
Cuts at:    1841    1914    2360
  Size:    73    446
  Fragments arranged by size:
           616    576    446    201    182    134    73    47    38
Tsp45I 'GTsAC_
Cuts at:    0    245    922    1181    1338    1718    1823    2360
  Size:    245    677    259    157    380    105    537
  Fragments arranged by size:
           677    537    380    259    245    157    105
Tsp509I 'AATT_
Cuts at:    0    1    485    930    1527    1932    2136    2280    2318
  Size:    1    484    445    597    405    204    144    38
Cuts at:    2318    2360
  Size:    42
  Fragments arranged by size:
           597    484    445    405    204    144    42    38

FIG. 13L

Tth111I GACn'n_nGTC
Cuts at:   0   64   2360
  Size:    64   2296
Tth111II CAArCAnnnnnnnnnn_nn'
Cuts at:   0   708   2360
  Size:    708   1652
UbaCI wGTACw
Cuts at:   0   1275   2360
  Size:    1275   1085
XcmI CCAnnnnn_n'nnnnTGG
Cuts at:   0   484   2360
  Size:    484   1876

Enzymes that do cut and were not excluded:

| | | | | |
|---|---|---|---|---|
| AccI | AceIII | AhdI | AlwI | AlwNI |
| ApaI | ApaBI | ApaLI | ApoI | AvaI |
| AvaII | BanI | BanII | BbsI | BbvI |
| Bce83I | BcefI | BfaI | BfiI | BglI |
| BglII | BmgI | BpmI | Bpu10I | BsaWI |
| BsaXI | BsbI | BscGI | BseRI | BsgI |
| BsiEI | BsiHKAI | BsmI | BsmAI | BsmBI |
| BsmFI | Bsp24I | Bsp1286I | BspMI | BsrI |
| BsrDI | BsrGI | BstXI | BstYI | Bsu36I |
| CjeI | CviRI | DdeI | DpnI | DraIII |
| DsaI | EaeI | EarI | EciI | Eco57I |
| EcoNI | EcoO109I | EcoRI | EcoRV | FauI |
| FokI | FspI | GdiII | HaeI | HgiEII |
| HhaI | Hin4I | HinfI | HphI | MaeII |
| MaeIII | MboII | MmeI | MscI | MsII |
| MspI | MspA1I | NciI | NcoI | NdeI |
| NlaIII | PleI | Psp5II | PstI | PvuII |
| RsaI | SanDI | SapI | Sau3AI | SfaNI |
| SfcI | SmaI | Sse8647I | SspI | StuI |
| StyI | TaqI | TaqII | TauI | TfiI |
| ThaI | TseI | Tsp45I | Tsp509I | Tth111I |
| Tth111II | UbaCI XcmI | | | |

Enzymes that do not cut:

| | | | | |
|---|---|---|---|---|
| AatII | AflII | AflIII | AscI | AvrII |
| BaeI | BamHI | BcgI | BcgI | BclI |
| BplI | Bpu1102I | BsaI | BsaAI | BsaBI |
| BsaHI | BspEI | BspGI | BspLU11I | BsrBI |
| BsrFI | BssHII | BssSI | Bst1107I | BstEII |
| ClaI | DraI | DrdI | DrdII | EagI |
| Eco47III | FseI | HaeII | HgaI | HincII |

FIG. 13M

| | | | | |
|---|---|---|---|---|
| HindIII | HpaI | KpnI | MluI | MseI |
| MunI | NarI | NgoAIV | NheI | NotI |
| NruI | NsiI | NspI | NspV | PacI |
| Pfl1108I | PflMI | PinAI | PmeI | PmlI |
| PshAI | Psp1406I | PvuI | RcaI | RleAI |
| RsrII | SacI | SacII | SalI | ScaI |
| SexAI | SfiI | SgfI | SgrAI | SnaBI |
| SpeI | SphI | SrfI | Sse8387I | SunI |
| SwaI | VspI | XbaI | XhoI | XmnI |

Enzymes excluded; MinCuts: 1    MaxCuts: 10

| | | | | |
|---|---|---|---|---|
| AciI | AluI | BccI | BsaJI | BslI |
| BsoFI | Cac8I | CjeI | CjePI | CjePI |
| CviJI | EcoRII | HaeIII | MnlI | MwoI |
| NlaIV | Sau96I | ScrFI | TspRI | |

FIG. 13N (Linear)MAPSORT of: piglac.gb_om check: 9514 from:1 to :2259
LOCUS      PIGLAC      2259 bp ss-mRNA            MAM
DEFINITION Sus scrofa lactoferrin mRNA, complete cds.
ACCESSION  M81327 M61828
KEYWORDS   lactoferrin.
SOURCE     Sus scrofa lactational mammary gland cDNA to mRNA.
  ORGANISM Sus scrofa . . .
Mismatch: 0 MinCuts = 1 MaxCuts: 10
With 209 enzymes: *

AceIII CAGCTCnnnnnnn'nnnn_
Cuts at:    0    497   915   1092   1740   2239   2259
  Size:       497   418   177    648    499    20
  Fragments arranged by size:
            648   499   497   418   177   20
AlwI GGATCnnnn'n_
Cuts at:    0    965   1531   1544   2036   2259
  Size:       965   566   13     492    223
  Fragments arranged by size:
            965   566   492   223   13
AlwNI CAG_nnn'CTG
Cuts at:    0    219   1034   1148   1196   2259
  Size:       219   815   114    48     1063
  Fragments arranged by size:
            1063   815   219   114   48
ApaLI G'TGCA_C
Cuts at:    0    1549   2259
  Size:       1549   710
ApoI r'AATT_y
Cuts at:    0    495   1488   1497   2259
  Size:       495   993   9      762
  Fragments arranged by size:
            993   762   495   9
AvaI C'yCGr_G
Cuts at:    0    33    787   2259
  Size:       33    754   1472
  Fragments arranged by size:
            1472   754   33
AvaII G'GwC_C
Cuts at:    0    791   932   1095   2259
  Size:       791   141   163   1164
  Fragments arranged by size:
            1164   791   163   141

FIG. 14A

BaeI ACnnnnGTAyC
Cuts at:    0   1614   2259
  Size:   1614   645

BamHI G'GATC_C
Cuts at:    0   1536   2259
  Size:   1536   723

BanI G'GyrC_C
Cuts at:    0   624   1265   1636   1770   2259
  Size:   624   641   371   134   489
  Fragments arranged by size:
         641   624   489   371   134

BanII G_rGCy'C
Cuts at:    0   475   2259
  Size:   475   1784

BccI CCATC
Cuts at:    0   81   197   233   530   842   956   1025   1229
  Size:   81   116   36   297   312   114   69   204
Cuts at:  1229   1769   2048   2259
  Size:   540   279   211
  Fragments arranged by size:
         540   312   297   279   211   204   116   114   81   69   36

BcefI ACGGCnnnnnnnnnnnn'n_
Cuts at:    0   1060   1075   1333   2259
  Size:   1060   15   258   926
  Fragments arranged by size:
         1060   926   258   15

BcgI CGAnnnnnnTGCnnnnnnnnnn_nn'
Cuts at:    0   367   401   2259
  Size:   367   34   1858
  Fragments arranged by size:
         1858   367   34

BfiI ACTGGG
Cuts at:    0   456   1823   2259
  Size:   456   1367   436
  Fragments arranged by size:
         1367   456   436

BglI GCCn_nnn'nGGC
Cuts at:    0   201   394   1768   2259
  Size:   201   193   1374   491
  Fragments arranged by size:
         1374   491   201   193

FIG. 14B

BglII A'GATC_T
Cuts at:    0   286   2259
  Size:        286   1973
BmgI GkGCCC
Cuts at:    0   518   1592   2259
  Size:        518   1074   667
  Fragments arranged by size:
               1074   667   518

BpII GAGnnnnnCTC
Cuts at:    0   171   2259
  Size:        171   2088
BpmI CTGGAGnnnnnnnnnnnnnnnn_nn'
Cuts at:    0   462   2259
  Size:        462   1797
Bpu10I CC'TnA_GC
Cuts at:    0   469   2149   2259
  Size:        469   1680   110
  Fragments arranged by size:
               1680   469    110
BsaI GGTCTCn'nnnn_
Cuts at:    0   1531   1841   1941   2259
  Size:        1531   310    100    318
  Fragments arranged by size:
               1531   318    310    100
BsaWI w'CCGG_w
Cuts at:    0   621   1939   2116   2259
  Size:        621   1318   177    143
  Fragments arranged by size:
               1318   621    177    143
BsbI CAACAC
Cuts at:    0   1332   1560   1696   1975   2259
  Size:        1332   228    136    279    284
  Fragments arranged by size:
               1332   284    279    228    136
BscGI CCCGT
Cuts at:    0   294   1011   2166   2259
  Size:        294   717    1155   93
  Fragments arranged by size:
               1155   717    294    93
BseRI GAGGAGnnnnnnnn_nn'
Cuts at:    0   1116   2151   2259
  Size:        1116   1035   108
  Fragments arranged by size:
               1116   1035   108

FIG. 14C

BsgI GTGCAGnnnnnnnnnnnnnnn_nn'
Cuts at:     0    624   2259
   Size:      624   1635
BsiEI CG_ry'CG
Cuts at:     0    273   2259
   Size:      273   1986
BsiHKAI G_wGCw'C
Cuts at:     0   1520   1553   2070   2259
   Size:     1520    33    517    189
   Fragments arranged by size:
             1520    517    189     33

BslI CCnn_nnn'nnGG
Cuts at:     0     69    449    612    788   1335   1577   1814   2084
   Size:      69    380    163    176    547    242    237    270
Cuts at:   2084   2142   2210   2259
   Size:      58     68     49
   Fragments arranged by size:
              547    380    270    242    237    176    163     69     68     58     49
BsmI GAATG_Cn'
Cuts at:     0    765   1655   2259
   Size:      765    890    604
   Fragments arranged by size:
              890    765    604
BsmAI GTCTCn'nnnn_
Cuts at:     0   1531   1841   1941   2078   2259
   Size:     1531    310    100    137    181
   Fragments arranged by size:
             1531    310    181    137    100
BsmFI GGGACnnnnnnnnnn'nnnn_
Cuts at:     0     50    308    729    777   2259
   Size:       50    258    421     48   1482
   Fragments arranged by size:
             1482    421    258     50     48
Bsp24I GACnnnnnnTGGnnnnnnn_nnnnn'
Cuts at:     0     37     69    215    247    536    568   2259
   Size:      37     32    146     32    289     32   1691
   Fragments arranged by size:
             1691    289    146     37     32     32     32
Bsp1286I G_dGCh'C
Cuts at:     0    475    520   1520   1553   1594   2070   2259
   Size:     475     45   1000     33     41    476    189
   Fragments arranged by size:
             1000    476    475    189     45     41     33

FIG. 14D

BspGI CTGGAC
Cuts at:     0    1098    1190    2259
  Size:   1098      92    1069
  Fragments arranged by size:
           1098    1069      92
BspMI ACCTGCnnnn'nnnn_
Cuts at:     0     394     703    2259
  Size:    394     309    1556
  Fragments arranged by size:
           1556     394     309
BsrI ACTG_Gn'
Cuts at:     0     119     257     459     756     860    1822    2259
  Size:    119     138     202     297     104     962     437
  Fragments arranged by size:
            962     437     297     202     138     119     104
BsrDI GCAATG_nn'
Cuts at:     0    1571    2259
  Size:   1571     688
BsrFI r'CCGG_y
Cuts at:     0     272     442    1117    2259
  Size:    272     170     675    1142
  Fragments arranged by size:
           1142     675     272     170
BssSI C'TCGT_G
Cuts at:     0    2251    2259
  Size:   2251       8
BstXI CCAn_nnnn'nTGG
Cuts at:     0     909    2259
  Size:    909    1350
BstYI r'GATC_y
Cuts at:     0     286     970    1536    2259
  Size:    286     684     566     723
  Fragments arranged by size:
            723     684     566     286
Bsu36I CC'TnA_GG
Cuts at:     0    1035    2209    2259
  Size:   1035    1174      50
  Fragments arranged by size:
           1174    1035      50
Cac8I GCn'nGC
Cuts at:     0    1069    1119    1250    1439    1461    1888    2133    2193
  Size:   1069      50     131     189      22     427     245      60
Cuts at:  2193    2259
  Size:     66
  Fragments arranged by size:
           1069     427     245     189     131      66      60      50      22

FIG. 14E

CjeI ACnnnnnnTGGnnnnnnn'nnnnnn_
Cuts at:   0    64   164   242   410   530   585   855   1526
  Size:       64   100   78   168   120   55   270   671
Cuts at: 1526  2259
  Size:    733
  Fragments arranged by size:
         733   671   270   168   120   100   78   64   55
CviRI TG'CA
Cuts at:   0   160   562   641   1156   1183   1322   1486   1551
  Size:      160   402   79   515   27   139   164   65
Cuts at: 1551  2259
  Size:    708
  Fragments arranged by size:
         708   515   402   164   160   139   79   65   27
DpnI GA'TC
Cuts at:   0   288   972   1538   2030   2259
  Size:      288   684   566   492   229
  Fragments arranged by size:
         684   566   492   288   229
DraIII CAC_nnn'GTG
Cuts at:   0   1557   2259
  Size:      1557   702
DrdI GACnn_nn'nnGTC
Cuts at:   0   1185   2259
  Size:      1185   1074
DrdII GAACCA
Cuts at:   0   364   1285   2259
  Size:      364   921   974
  Fragments arranged by size:
         974   921   364
DsaI C'CryG_G
Cuts at:   0   1090   1348   1453   2259
  Size:      1090   258   105   806
  Fragments arranged by size:
         1090   806   258   105
EaeI y'GGCC_r
Cuts at:   0   270   490   2259
  Size:      270   220   1769
  Fragments arranged by size:
         1769   270   220

FIG. 14F

EagI C'GGCC_G
Cuts at:    0    270   2259
  Size:       270   1989
EarI CTCTTCn'nnn_
Cuts at:    0    15    295   1711  2259
  Size:       15    280   1416  548
  Fragments arranged by size:
              1416  548   280   15
EcoNI CCTnn'n_nnAGG
Cuts at:    0    67    2208  2259
  Size:       67    2141  51
  Fragments arranged by size:
              2141  67    51
EcoO109I rG'GnC_Cy
Cuts at:    0    791   932   1031  2145  2259
  Size:       791   141   99    1114  114
  Fragments arranged by size:
              1114  791   141   114   99
EcoRI G'AATT_C
Cuts at:    0    1497  2259
  Size:       1497  762
FauI CCCGCnnnn'nn_
Cuts at:    0    26    1241  2086  2140  2259
  Size:       26    1215  845   54    119
  Fragments arranged by size:
              1215  845   119   54    26
FokI GGATGnnnnnnnnn'nnnn_
Cuts at:    0    1011  1239  1434  1671  2218  2259
  Size:       1011  228   195   237   547   41
  Fragments arranged by size:
              1011  547   237   228   195   41
FspI TGC'GCA
Cuts at:    0    524   1110  2259
  Size:       524   586   1149
  Fragments arranged by size:
              1149  586   524
GdiII y'GGCC_G
Cuts at:    0    270   2259
  Size:       270   1989
HaeI wGG'CCw
Cuts at:    0    397   492   1164  2259
  Size:       397   95    672   1095
  Fragments arranged by size:
              1095  672   397   95

FIG. 14G

HgiEII ACCnnnnnnGGT
Cuts at:    0    230    2259
  Size:        230    2029
HhaI G_CG'C
Cuts at:    0    525    1064    1089    1111    2259
  Size:        525    539    25    22    1148
  Fragments arranged by size:
           1148    539    525    25    22
Hin4I GAbnnnnnvTC
Cuts at:    0    83    171    1235    1541    1791    2259
  Size:        83    88    1064    306    250    468
  Fragments arranged by size:
           1064    468    306    250    88    83
HincII GTy'rAC
Cuts at:    0    1469    2259
  Size:        1469    790
HinfI G'AnT_C
Cuts at:    0    305    987    2173    2259
  Size:        305    682    1186    86
  Fragments arranged by size:
           1186    682    305    86
HphI GGTGAnnnnnnn_n'
Cuts at:    0    1373    1797    2259
  Size:        1373    424    462
  Fragments arranged by size:
           1373    462    424
MaeIII 'GTnAC_
Cuts at:    0    221    433    862    1617    1679    1784    1803    2039
  Size:        221    212    429    755    62    105    19    236
Cuts at:    2039    2259
  Size:        220
  Fragments arranged by size:
           755    429    236    221    220    212    105    62    19
MboII GAAGAnnnnnnn_n'
Cuts at:    0    2    151    312    353    491    980    1728    1912
  Size:        2    149    161    41    138    489    748    184
Cuts at:    1912    2259
  Size:        347
  Fragments arranged by size:
           748    489    347    184    161    149    138    41
           2

FIG. 14H

MscI TGG'CCA
Cuts at:    0    492    2259
   Size:       492    1767
MslII CAynn'nnrTG
Cuts at:    0    1422    1452    2259
   Size:       1422    30    807
   Fragments arranged by size:
              1422    807    30
MspA1I CmG'CkG
Cuts at:    0    282    557    1050    2181    2259
   Size:       282    275    493    1131    78
   Fragments arranged by size:
              1131    493    282    275    78
MwoI GCnn_nnn'nnGC
Cuts at:    0    201    210    394    470    810    1068    1135    1138
   Size:       201    9    184    76    340    258    67    3
Cuts at: 1138    1650    1768    2259
   Size:       512    118    491
   Fragments arranged by size:
              512    491    340    258    201    184    118    76    67    9    3
NciI CC's_GG
Cuts at:    0    192    413    714    788    789    1534    1625    1920
   Size:       192    221    301    74    1    745    91    295
Cuts at: 1920    2259
   Size:       339
   Fragments arranged by size:
              745    339    301    295    221    192    91    74    1
NcoI C'CATG_G
Cuts at:    0    1453    2259
   Size:       1453    806
NgoAIV G'CCGG_C
Cuts at:    0    1117    2259
   Size:       1117    1142
NlaIII _CATG'
Cuts at:    0    5    155    804    1457    1830    2105    2259
   Size:       5    150    649    653    373    275    154
   Fragments arranged by size:
              653    649    373    275    154    150    5

FIG. 14I

PflMI CCAn_nnn'nTGG
Cuts at:    0   1577   2259
  Size:        1577    682
Psp5II rG'GwC_Cy
Cuts at:    0    791   932   2259
  Size:         791   141   1327
  Fragments arranged by size:
            1327   791   141
PstI C_TGCA'G
Cuts at:    0   1158   2259
  Size:        1158   1101
PvuII CAG'CTG
Cuts at:    0    557   2181   2259
  Size:         557   1624    78
  Fragments arranged by size:
            1624   557    78
RcaI T'CATG_A
Cuts at:    0   2101   2259
  Size:        2101    158
RsaI GT'AC
Cuts at:    0    261   680   999   1014   2259
  Size:         261   419   319    15    1245
  Fragments arranged by size:
            1245   419   319   261    15
SanDI GG'GwC_CC
Cuts at:    0    791   2259
  Size:         791   1468
SapI GCTCTTCn'nnn_
Cuts at:    0    15   2259
  Size:         15   2244
Sau3AI 'GATC_
Cuts at:    0    286   970   1536   2028   2259
  Size:         286   684   566    492    231
  Fragments arranged by size:
             684   566   492   286    231
SfaNI GCATCnnnnn'nnnn_
Cuts at:    0    206   938   1192   1202   2259
  Size:         206   732   254     10    1057
  Fragments arranged by size:
            1057   732   254   206     10
SfcI C'TryA_G
Cuts at:    0    334   427   1154   2259
  Size:         334    93   727   1105
  Fragments arranged by size:
            1105   727   334    93

FIG. 14J

SmaI CCC'GGG
Cuts at:    0    789    2259
  Size:       789    1470
Sse8647I AG'GwC_CT
Cuts at:    0    932    2259
  Size:       932    1327
SspI AAT'ATT
Cuts at:    0    2022    2259
  Size:       2022    237
StuI AGG'CCT
Cuts at:    0    397    2259
  Size:       397    1862
StyI C'CwwG_G
Cuts at:    0    398    1453    1997    2259
  Size:       398    1055    544    262
  Fragments arranged by size:
              1055    544    398    262
TaqI T'CG_A
Cuts at:    0    77    377    749    2259
  Size:       77    300    372    1510
  Fragments arranged by size:
              1510    372    300    77
TauI GCsGC
Cuts at:    0    116    202    270    1065    2259
  Size:       116    86    68    795    1194
  Fragments arranged by size:
              1194    795    116    86    68
TfiI G'AwT_C
Cuts at:    0    305    987    2173    2259
  Size:       305    682    1186    86
  Fragments arranged by size:
              1186    682    305    86
ThaI CG'CG
Cuts at:    0    201    1064    2259
  Size:       201    863    1195
  Fragments arranged by size:
              1195    863    201
Tsp45I 'GTsAC_
Cuts at:    0    221    862    1679    1784    1803    2039    2259
  Size:       221    641    817    105    19    236    220
  Fragments arranged by size:
              817    641    236    221    220    105    19

FIG. 14K

Tsp509I 'AATT_
Cuts at:    0    495   1488   1497   1731   2244   2259
  Size:       495    993     9    234    513     15
  Fragments arranged by size:
              993    513    495    234     15      9
Tth111I GACn'n_nGTC
Cuts at:    0     49   2259
  Size:       49   2210
Tth111II CAArCAnnnnnnnnn_nn'
Cuts at:    0    234    577    675   1452   1922   2259
  Size:      234    343     98    777    470    337
  Fragments arranged by size:
              777    470    343    337    234     98
UbaCI wGTACw
Cuts at:    0    261    680   2259
  Size:      261    419   1579
  Fragments arranged by size:
             1579    419    261
XcmI CCAnnnn_n'nnnnTGG
Cuts at:    0    396   1829   2259
  Size:      396   1433    430
  Fragments arranged by size:
             1433    430    396
XmnI GAAnn'nnTTC
Cuts at:    0      9    348   2259
  Size:        9    339   1911
  Fragments arranged by size:
             1911    339      9

Enzymes that do cut and were not excluded:
| AceIII | AlwI | AlwNI | ApaLI | ApoI | AvaI | AvaII | BaeI |
| BamHI | BanI | BanII | BccI | BcefI | BcgI | BfiI | BglI |
| BglII | BmgI | BplI | BpmI | Bpu10I | BsaI | BsaWI | BsbI |
| BscGI | BseRI | BsgI | BsiEI | BsiHKAI | BslI | BsmI | BsmAI |
| BsmFI | Bsp24I | Bsp1286I | BspGI | BspMI | BsrI | BsrDI | BsrFI |
| BssSI | BstXI | BstYI | Bsu36I | Cac8I | CjeI | CviRI | DpnI |
| DraIII | DrdI | DrdII | DsaI | EaeI | EagI | EarI | EcoNI |
| EcoO109I | EcoRI | FauI | FokI | FspI | GdiII | HaeI | HgiEII |
| HhaI | Hin4I | HincII | HinfI | HphI | MaeIII | MboII | MscI |
| MslI | MspA1I | MwoI | NciI | NcoI | NgoAIV | NlaIII | PflMI |
| Psp5II | PstI | PvuII | RcaI | RsaI | SanDI | SapI | Sau3AI |
| SfaNI | SfcI | SmaI | Sse8647I | SspI | StuI | StyI | TaqI |
| TauI | TfiI | ThaI | Tsp45I | Tsp509I | Tth111I | Tth111II | UbaCI |
| XcmI | XmnI | | | | | | |

FIG. 14L

Enzymes that do not cut:

| | | | | | | | |
|---|---|---|---|---|---|---|---|
| AatII | AccI | AflII | AflIII | AhdI | ApaI | ApaBI | AscI |
| AvrII | BbsI | Bce83I | BclI | BfaI | Bpu1102I | BsaAI | BsaBI |
| BsaHI | BsaXI | BsmBI | BspEI | BspLU11I | BsrBI | BsrGI | BssHII |
| Bst1107I | BstEII | ClaI | DraI | EciI | Eco47III | Eco57I | EcoRV |
| FseI | HaeII | HgaI | HindIII | HpaI | KpnI | MaeII | MluI |
| MmeI | MseI | MunI | NarI | NdeI | NheI | NotI | NruI |
| NsiI | NspI | NspV | PacI | Pfl1108I | PinAI | PleI | PmeI |
| PmlI | PshAI | Psp1406I | PvuI | RleAI | RsrII | SacI | SacII |
| SalI | ScaI | SexAI | SfiI | SgfI | SgrAI | SnaBI | SpeI |
| SphI | SrfI | Sse8387I | SunI | SwaI | TaqII | TaqII | VspI |
| XbaI | XhoI | | | | | | |

Enzymes excluded; MinCuts: 1  MaxCuts: 10

| | | | | | | | |
|---|---|---|---|---|---|---|---|
| AciI | AluI | BbvI | BsaJI | BsoFI | CjeI | CjePI | CjePI |
| CviJI | DdeI | EcoRII | HaeIII | MnlI | MspI | NlaIV | Sau96I |
| ScrFI | TseI | TspRI | | | | | |

FIG. 14M (Linear) MAPSORT of: bovlactof.gb_om check: 2217 from: 1 to: 2351
LOCUS      BOVLACTOF    2351 bp ss-mRNA       MAM
DEFINITION  Bovine lactoferrin mRNA, complete cds.
ACCESSION   M63502
KEYWORDS    lactoferrin.
SOURCE      B.taurus, cDNA to mRNA.
  ORGANISM  Bos taurus . . .
Mismatch: 0  MinCuts = 1  MaxCuts: 10
With 209 enzymes: *

AceIII CAGCTCnnnnnnn'nnnn_
Cuts at:    0    494    526    969    1553    1841    2216    2351
   Size:      494    32    443    584    288    375    135
   Fragments arranged by size:
              584    494    443    375    288    135    32
AflIII A'CryG_T
Cuts at:    0    1913    2351
   Size:      1913    438
AhdI GACnn_n'nnGTC
Cuts at:    0    1460    2351
   Size:      1460    891
AlwI GGATCnnnn'n_
Cuts at:    0    480    1019    1032    2351
   Size:      480    539    13    1319
   Fragments arranged by size:
              1319    539    480    13
AlwNI CAG_nnn'CTG
Cuts at:    0    1600    1631    1928    1946    2351
   Size:      1600    31    297    18    405
   Fragments arranged by size:
              1600    405    297    31    18
ApoI r'AATT_y
Cuts at:    0    549    1442    1551    2351
   Size:      549    893    109    800
   Fragments arranged by size:
              893    800    549    109
AvaI C'yCGr_G
Cuts at:    0    101    522    652    2351
   Size:      101    421    130    1699
   Fragments arranged by size:
              1699    421    130    101

FIG. 15A

AvaII G'GwC_C
Cuts at:    0    305    416    460    770    845    986    1149    2244
  Size:       305   111    44    310    75    141    163    1095
Cuts at: 2244   2351
  Size:      107
  Fragments arranged by size:
              1095   310   305   163   141   111   107   75   44
BamHI G'GATC_C
Cuts at:    0    1024   2351
  Size:      1024   1327
BanI G'GyrC_C
Cuts at:    0    678    806    1319   1393   1690   1824   2351
  Size:       678   128    513    74    297    134    527
  Fragments arranged by size:
              678   527   513   297   134   128   74
BanII G_rGCy'C
Cuts at:    0    80     529    1062   1435   2351
  Size:       80    449    533    373    916
  Fragments arranged by size:
              916   533   449   373   80
BbsI GAAGACnn'nnnn_
Cuts at:    0    895    2351
  Size:      895   1456
BbvI GCAGCnnnnnnnn'nnnn_
Cuts at:    0    83     342    409    412    1842   1915   1920   2351
  Size:       83    259    67     3     1430   73    5     431
  Fragments arranged by size:
              1430   431   259   83    73    67    5    3
BccI CCATC
Cuts at:    0    120    128    162    278    881    1283   1823   2351
  Size:       120   8     34    116    603    402    540    528
  Fragments arranged by size:
              603   540   528   402   120   116   34   8
Bce83I CTTGAGnnnnnnnnnnnnnnnn_nn'
Cuts at:    0    524    2351
  Size:      524   1827
BcefI ACGGCnnnnnnnnnnnn'n_
Cuts at:    0    370    1129   1231   1387   1462   2113   2351
  Size:       370   759    102    156    75    651    238
  Fragments arranged by size:
              759   651   370   238   156   102   75
BfaI C'TA_G
Cuts at:    0    1365   2183   2351
  Size:      1365   818    168
  Fragments arranged by size:
              1365   818   168

FIG. 15B

BfiI ACTGGG
Cuts at:    0    1776    2351
   Size:    1776    575
BglI GCCn_nnn'nGGC
Cuts at:    0    448    1578    1822    2351
   Size:    448    1130    244    529
   Fragments arranged by size:
            1130    529    448    244
BglII A'GATC_T
Cuts at:    0    337    2351
   Size:    337    2014
BmgI GkGCCC
Cuts at:    0    1572    1646    2351
   Size:    1572    74    705
   Fragments arranged by size:
            1572    705    74
BpmI CTGGAGnnnnnnnnnnnnnnn_nn'
Cuts at:    0    516    727    2216    2351
   Size:    516    211    1489    135
   Fragments arranged by size:
            1489    516    211    135
Bpu10I CC'TnA_GC
Cuts at:    0    1699    2202    2351
   Size:    1699    503    149
   Fragments arranged by size:
            1699    503    149
BsaI GGTCTCn'nnnn_
Cuts at:    0    1373    2351
   Size:    1373    978
BsaAI yAC'GTr
Cuts at:    0    1916    2351
   Size:    1916    435
BsaHI Gr'CG_yC
Cuts at:    0    32    807    1218    2351
   Size:    32    775    411    1133
   Fragments arranged by size:
            1133    775    411    32
BsaWI w'CCGG_w
Cuts at:    0    15    1339    2351
   Size:    15    1324    1012
   Fragments arranged by size:
            1324    1012    15
BsaXI ACnnnnnCTCC
Cuts at:    0    634    1058    2351
   Size:    634    424    1293
   Fragments arranged by size:
            1293    634    424

FIG. 15C

BsbI CAACAC
Cuts at:    0    2029   2351
  Size:    2029   322
BscGI CCCGT
Cuts at:    0    449   498   702   2351
  Size:    449   49    204   1649
  Fragments arranged by size:
           1649   449   204   49
BseRI GAGGAGnnnnnnnn_nn'
Cuts at:    0    638   1119  1170  2198  2351
  Size:    638   481   51    1028  153
  Fragments arranged by size:
           1028  638   481   153   51
BsiHKAI G_wGCw'C
Cuts at:    0    191   1767  2351
  Size:    191   1576  584
  Fragments arranged by size:
           1576  584   191
BsmAI GTCTCn'nnnn_
Cuts at:    0    361   703   723   949   1373  1897  2351
  Size:    361   342   20    226   424   524   454
  Fragments arranged by size:
           524   454   424   361   342   226   20
BsmBI CGTCTCn'nnnn_
Cuts at:    0    703   723   2351
  Size:    703   20    1628
  Fragments arranged by size:
           1628  703   20
BsoFI GC'n_GC
Cuts at:    0    97    155   321   331   401   423   1193  1856
  Size:    97    58    166   10    70    22    770   663
Cuts at:   1856  1909  1929  2351
  Size:    53    20    422
  Fragments arranged by size:
           770   663   422   166   97    70    58    53    22    20    10
Bsp24I GACnnnnnnTGGnnnnnnnn_nnnnn'
Cuts at:    0    76    108   260   292   590   622   882   914
  Size:    76    32    152   32    298   32    260   32
Cuts at:   914   1725  1757  2351
  Size:    811   32    594
  Fragments arranged by size:
           811   594   298   260   152   76    32    32    32    32    32

FIG. 15D

Bsp1286I G_dGCh'C
Cuts at:   0    80   191   529   1062   1435   1574   1648   1767
  Size:       80   111   338   533    373    139    74    119
Cuts at: 1767  2351
  Size:      584
  Fragments arranged by size:
         584   533   373   338   139   119   111   80   74
BspEI T'CCGG_A
Cuts at:   0    15   2351
  Size:      15   2336
BspGI CTGGAC
Cuts at:   0   416   511   1634   2351
  Size:     416    95  1123    717
  Fragments arranged by size:
         1123   717   416   95
BspMI ACCTGCnnnn'nnnn_
Cuts at:   0   448   997   2351
  Size:     448   549  1354
  Fragments arranged by size:
         1354   549   448
BsrI ACTG_Gn'·
Cuts at:   0   324   635   773   810   1779   2351
  Size:     324   311   138    37   969    572
  Fragments arranged by size:
         969   572   324   311   138   37
BsrBI GAG'CGG
Cuts at:   0   1192   2351
  Size:    1192   1159
BsrDI GCAATG_nn'
Cuts at:   0   2101   2351
  Size:    2101   250
BstXI CCAn_nnnn'nTGG
Cuts at:   0   963   2351
  Size:     963   1388
BstYI r'GATC_y
Cuts at:   0   337   1024   2351
  Size:     337   687   1327
  Fragments arranged by size:
         1327   687   337
Bsu36I CC'TnA_GG
Cuts at:   0   1089   1153   2351
  Size:    1089    64   1198
  Fragments arranged by size:
         1198   1089   64

FIG. 15E

CviRI TG'CA
Cuts at:   0     425    577    616    695    1237   1491   1770   2174
  Size:    425   152    39     79     542    254    279    404
Cuts at:   2174  2351
  Size:    177
  Fragments arranged by size:
           542   425    404    279    254    177    152    79     39
DpnI GA'TC
Cuts at:   0     339    474    897    1026   1518   2351
  Size:    339   135    423    129    492    833
  Fragments arranged by size:
           833   492    423    339    135    129
DraIII CAC_nnn'GTG
Cuts at:   0     1886   2035   2351
  Size:    1886  149    316
  Fragments arranged by size:
           1886  316    149
DrdI GACnn_nn'nnGTC
Cuts at:   0     353    1239   2351
  Size:    353   886    1112
  Fragments arranged by size:
           1112  886    353
DrdII GAACCA
Cuts at:   0     146    634    659    2351
  Size:    146   488    25     1692
  Fragments arranged by size:
           1692  488    146    25
DsaI C'CryG_G
Cuts at:   0     1144   1213   1402   1477   1507   2351
  Size:    1144  69     189    75     30     844
  Fragments arranged by size:
           1144  844    189    75     69     30
EaeI y'GGCC_r
Cuts at:   0     321    382    977    1193   2041   2098   2351
  Size:    321   61     595    216    848    57     253
  Fragments arranged by size:
           848   595    321    253    216    61     57

FIG. 15F

EarI CTCTTCn'nnn_
Cuts at:   0    54   2351
  Size:       54   2297
EciI TCCGCC
Cuts at:   0    259   2351
  Size:       259   2092
Eco57I CTGAAGnnnnnnnnnnnnnnnn_nn'
Cuts at:   0    1787   2283   2351
  Size:       1787   496   68
  Fragments arranged by size:
              1787   496   68
EcoNI CCTnn'n_nnAGG
Cuts at:   0    206   840   1698   2351
  Size:       206   634   858   653
  Fragments arranged by size:
              858   653   634   206
EcoO109I rG'GnC_Cy
Cuts at:   0    305   845   986   1149   1628   2244   2351
  Size:       305   540   141   163   479   616   107
  Fragments arranged by size:
              616   540   479   305   163   141   107
EcoRI G'AATT_C
Cuts at:   0    1442   1551   2351
  Size:       1442   109   800
  Fragments arranged by size:
              1442   800   109
FauI CCCGCnnnn'nn_
Cuts at:   0    65    205   290   1071   1295   2140   2351
  Size:       65    140   85    781   224   845   211
  Fragments arranged by size:
              845   781   224   211   140   85    65
FokI GGATGnnnnnnnnn'nnnn_
Cuts at:   0    185   273   288   462   828   891   1293   1488
  Size:       185   88    15    174   366   63    402   195
Cuts at:   1488   2351
  Size:       863
  Fragments arranged by size:
              863   402   366   195   185   174   88    63    15

FIG. 15G

FspI TGC'GCA
Cuts at:     0    1541   2351
  Size:      1541  810
GdiII y'GGCC_G
Cuts at:     0    321   382   977   1193   2098   2351
  Size:      321   61    595   216   905    253
  Fragments arranged by size:
             905   595   321   253   216    61
HaeI wGG'CCw
Cuts at:     0    1315   2043   2351
  Size:      1315  728    308
  Fragments arranged by size:
             1315  728    308
HaeII r_GCGC'y
Cuts at:     0    810    1050   2351
  Size:      810   240    1301
  Fragments arranged by size:
             1301  810    240
HgaI GACGCnnnnn'nnnnn_
Cuts at:     0    40    1207   2351
  Size:      40    1167  1144
  Fragments arranged by size:
             1167  1144  40
HgiEII ACCnnnnnnnGGT
Cuts at:     0    275    2351
  Size:      275   2076
HhaI G_CG'C
Cuts at:     0    809   920   1049   1118   1542   2151   2239   2351
  Size:      809   111   129   69     424    609    88     112
  Fragments arranged by size:
             809   609   424   129    112    111    88     69
Hin4I GAbnnnnnnvTC
Cuts at:     0    1289   1459   1588   1845   2351
  Size:      1289  170    129    257    506
  Fragments arranged by size:
             1289  506    257    170    129
HincII GTy'rAC
Cuts at:     0    609    1523   2351
  Size:      609   914    828
  Fragments arranged by size:
             914   828    609

FIG. 15H

HindIII A'AGCT_T
Cuts at:     0    903   2351
  Size:    903   1448
HinfI G'AnT_C
Cuts at:    0    19    354    487    516   1002   1041   1597   1790
  Size:    19    335    133    29    486    39    556    193
Cuts at:  1790   1877   2351
  Size:    87    474
  Fragments arranged by size:
         556   486   474   335   193   133    87    39    29    19
HphI GGTGAnnnnnnn_n'
Cuts at:    0    191   1121   2351
  Size:    191   930   1230
  Fragments arranged by size:
         1230   930   191
KpnI G_GTAC'C
Cuts at:    0   1397   2351
  Size:   1397   954
MaeII A'CG_T
Cuts at:    0    112    712   1201   1705   1714   1915   2064   2351
  Size:    112    600    489    504     9    201    149    287
  Fragments arranged by size:
         600   504   489   287   201   149   112     9
MaeIII 'GTnAC_
Cuts at:    0    266    517   1202   1838   2093   2351
  Size:    266   251   685    636    255    258
  Fragments arranged by size:
         685   636   266   258   255   251
MboII GAAGAnnnnnnn_n'
Cuts at:    0    41    188    404    545    900   1094   1175   2082
  Size:    41    147    216    141    355    194    81    907
Cuts at:  2082   2351
  Size:    269
  Fragments arranged by size:
         907   355   269   216   194   147   141    81    41

FIG. 15I

MmeI TCCrACnnnnnnnnnnnnnnnnnnnn_nn'
Cuts at:    0    2248    2351
  Size:       2248    103
MscI TGG'CCA
Cuts at:    0    2043    2351
  Size:       2043    308
MseI T'TA_A
Cuts at:    0    724    2351
  Size:       724    1627
MslI CAynn'nnrTG
Cuts at:    0    204    373    480    1476    1506    2351
  Size:       204    169    107    996    30    845
  Fragments arranged by size:
              996    845    204    169    107    30
MspI C'CG_G
Cuts at:    0    16    237    302    431    653    976    1340    1678
  Size:       16    221    65    129    222    323    364    338
Cuts at:    1678    1974    2351
  Size:       296    377
  Fragments arranged by size:
              377    364    338    323    296    222    221    129    65    16
MspA1I CmG'CkG
Cuts at:    0    413    422    465    565    2351
  Size:       413    9    43    100    1786
  Fragments arranged by size:
              1786    413    100    43    9
NarI GG'CG_CC
Cuts at:    0    807    2351
  Size:       807    1544
NciI CC's_GG
Cuts at:    0    238    303    653    654    976    1679    1974    2351
  Size:       238    65    350    1    322    703    295    377
  Fragments arranged by size:
              703    377    350    322    295    238    65    1
NcoI C'CATG_G
Cuts at:    0    1507    2351
  Size:       1507    844
NheI G'CTAG_C
Cuts at:    0    2182    2351
  Size:       2182    169
NlaIII _CATG'
Cuts at:    0    44    287    858    1441    1511    2351
  Size:       44    243    571    583    70    840
  Fragments arranged by size:
              840    583    571    243    70    44

FIG. 15J

PflMI CCAn_nnn'nTGG
Cuts at:    0    1631    2351
  Size:    1631    720
PleI GAGTCnnnn'n_
Cuts at:    0    27    362    524    996    1591    2351
  Size:    27    335    162    472    595    760
  Fragments arranged by size:
         760    595    472    335    162    27
PmlI CAC'GTG
Cuts at:    0    1916    2351
  Size:    1916    435
Psp5II rG'GwC_Cy
Cuts at:    0    305    845    986    1149    2244    2351
  Size:    305    540    141    163    1095    107
  Fragments arranged by size:
         1095    540    305    163    141    107
Psp1406I AA'CG_TT
Cuts at:    0    112    2351
  Size:    112    2239
PstI C_TGCA'G
Cuts at:    0    697    1493    1772    2351
  Size:    697    796    279    579
  Fragments arranged by size:
         796    697    579    279
PvuII CAG'CTG
Cuts at:    0    413    422    565    2351
  Size:    413    9    143    1786
  Fragments arranged by size:
         1786    413    143    9
RsaI GT'AC
Cuts at:    0    125    501    1053    1122    1395    1665    2351
  Size:    125    376    552    69    273    270    686
  Fragments arranged by size:
         686    552    376    273    270    125    69
SanDI GG'GwC_CC
Cuts at:    0    305    2351
  Size:    305    2046
SapI GCTCTTCn'nnn_
Cuts at:    0    54    2351
  Size:    54    2297
Sau3AI 'GATC_
Cuts at:    0    337    472    895    1024    1516    2351
  Size:    337    135    423    129    492    835
  Fragments arranged by size:
         835    492    423    337    135    129

FIG. 15K

ScaI AGT'ACT
Cuts at:    0    1665    2351
  Size:   1665    686
SfaNI GCATCnnnnn'nnnn_
Cuts at:   0    250    251    806    1246    1256    2351
  Size:    250    1    555    440    10    1095
  Fragments arranged by size:
           1095    555    440    250    10    1
SfcI C'TryA_G
Cuts at:    0    693    1489    1768    2351
  Size:    693    796    279    583
  Fragments arranged by size:
           796    693    583    279
SmaI CCC'GGG
Cuts at:    0    654    2351
  Size:    654    1697
SspI AAT'ATT
Cuts at:    0    2076    2351
  Size:   2076    275
StyI C'CwwG_G
Cuts at:    0    71    80    223    452    1507    2351
  Size:    71    9    143    229    1055    844
  Fragments arranged by size:
           1055    844    229    143    71    9
TaqI T'CG_A
Cuts at:    0    116    523    1032    1819    2351
  Size:    116    407    509    787    532
  Fragments arranged by size:
           787    532    509    407    116
TaqII GACCGAnnnnnnnnn_nn'
Cuts at:    0    174    457    2351
  Size:    174    283    1894
  Fragments arranged by size:
           1894    283    174
TauI GCsGC
Cuts at:    0    155    321    1193    2351
  Size:    155    166    872    1158
  Fragments arranged by size:
           1158    872    166    155
TfiI G'AwT_C
Cuts at:    0    487    1041    1790    1877    2351
  Size:    487    554    749    87    474
  Fragments arranged by size:
           749    554    487    474    87

FIG. 15L

ThaI CG'CG
Cuts at:    0    246    1118    2239    2351
  Size:    246    872    1121    112
  Fragments arranged by size:
         1121    872    246    112

TseI GCwGC
Cuts at:    0    97    331    401    423    1856    1909    1929    2351
  Size:    97    234    70    22    1433    53    20    422
  Fragments arranged by size:
         1433    422    234    97    70    53    22    20

Tsp45I 'GTsAC_
Cuts at:    0    266    517    1202    1838    2093    2351
  Size:    266    251    685    636    255    258
  Fragments arranged by size:
         685    636    266    258    255    251

Tsp509I 'AATT_
Cuts at:    0    549    1442    1551    2298    2329    2351
  Size:    549    893    109    747    31    22
  Fragments arranged by size:
         893    747    549    109    31    22

TspRI CAGTGnn'
Cuts at:    0    171    642    742    817    1182    1232    1304    1772
  Size:    171    471    100    75    365    50    72    468
Cuts at: 1772    2036    2351
  Size:    264    315
  Fragments arranged by size:
         471    468    365    315    264    171    100    75    72    50

Tth111I GACn'n_nGTC
Cuts at:    0    88    515    1737    2351
  Size:    88    427    1222    614
  Fragments arranged by size:
         1222    614    427    88

Tth111II CAArCAnnnnnnnnnn_nn'
Cuts at:    0    279    604    729    1368    1938    1976    2351
  Size:    279    325    125    639    570    38    375
  Fragments arranged by size:
         639    570    375    325    279    125    38

FIG. 15M

UbaCI wGTACw
Cuts at:   0   1665   2351
    Size:   1665   686
XcmI CCAnnnn'n'nnnnTGG
Cuts at:   0   450   2351
    Size:   450   1901
XhoI C'TCGA_G
Cuts at:   0   522   2351
    Size:   522   1829
XmnI GAAnn'nnTTC
Cuts at:   0   48   232   2351
    Size:   48   184   2119
  Fragments arranged by size:
          2119   184   48
Enzymes that do cut and were not excluded:

| AceIII | AflIII | AhdI | AlwI | AlwNI | ApoI | AvaI | AvaII |
|---|---|---|---|---|---|---|---|
| BamHI | BanI | BanII | BbsI | BbvI | BccI | Bce83I | BcefI |
| BfaI | BfiI | BgII | BglII | BmgI | BpmI | Bpu10I | BsaI |
| BsaAI | BsaHI | BsaWI | BsaXI | BsbI | BscGI | BseRI | BsiHKAI |
| BsmAI | BsmBI | BsoFI | Bsp24I | Bsp1286I | BspEI | BspGI | BspMI |
| BsrI | BsrBI | BsrDI | BstXI | BstYI | Bsu36I | CviRI | DpnI |
| DraIII | DrdI | DrdII | DsaI | EaeI | EarI | EciI | Eco57I |
| EcoNI | EcoO109I | EcoRI | FauI | FokI | FspI | GdiII | HaeI |
| HaeII | HgaI | Hgi | EII | HhaI | Hin4I | HincII | HindIII |
| HinfI | HphI | KpnI | MaeII | MaeIII | MboII | MmeI | MscI |
| MseI | MslI | MspI | MspA1I | NarI | NciI | NcoI | NheI |
| NlaIII | PflMI | PleI | PmlI | Psp5II | Psp1406I | PstI | PvuII |
| RsaI | SanDI | SapI | Sau3AI | ScaI | SfaNI | SfcI | SmaI |
| SspI | StyI | TaqI | TaqII | TauI | TfiI | ThaI | TseI |
| Tsp45I | Tsp509I | TspRI | Tth111I | Tth111II | UbaCI | XcmI | XhoI |
| XmnI | | | | | | | |

Enzymes that do not cut:

| AatII | AccI | AflII | ApaI | ApaBI | ApaLI | AscI | AvrII |
|---|---|---|---|---|---|---|---|
| BaeI | BcgI | BcgI | BclI | BplI | Bpu1102I | BsaBI | BsgI |
| BsiEI | BsmI | BspLU11I | BsrFI | BsrGI | BssHII | BssSI | Bst1107I |
| BstEII | ClaI | DraI | EagI | Eco47III | EcoRV | FseI | HpaI |
| MluI | MunI | NdeI | NgoAIV | NotI | NruI | NsiI | NspI |
| NspV | PacI | Pfl1108I | PinAI | PmeI | PshAI | PvuI | RcaI |
| RleAI | RsrII | SacI | SacII | SalI | SexAI | SfiI | SgfI |
| SgrAI | SnaBI | SpeI | SphI | SrfI | Sse8387I | Sse8647I | StuI |
| SunI | SwaI | VspI | XbaI | | | | |

Enzymes excluded; MinCuts: 1 MaxCuts: 10

| AciI | AluI | BsaJI | BslI | BsmFI | Cac8I | CjeI | CjeI |
|---|---|---|---|---|---|---|---|
| CjePI | CjePI | CviJI | DdeI | EcoRII | HaeIII | MnlI | MwoI |
| NlaIV | Sau96I | ScrFI | | | | | |

FIG. 15N

```
                                          Mature ∝-Amylase
         ∝-Amlase Signal Sequence
1) ——————————————— AlaLeuAlaAlaThrProAlaAspTrpArgSerGlnSer Mature Human Lactoferrin
      Lactoferrin Signal Sequence
2) ——————————————— CysLeuAlaGlyArgArgArgArgSerValGlnTrpCys Mature Recombinant Lactoferrin
         ∝-Amylase Signal Sequence
3) ——————————————— AlaLeuAlaAlaGlyArgArgArgArgSerValGlnTrp
```

FIG. 16C

EXPRESSION OF PROCESSED RECOMBINANT LACTOFERRIN AND LACTOFERRIN POLYPEPTIDE FRAGMENTS FROM A FUSION PRODUCT IN ASPERGILLUS

This invention was made with government support under Grant No. HD27965 awarded by the National Institute of Health. The government has certain rights in the invention.

RELATED APPLICATIONS

This application is a continuation-in-part of co-pending application U.S. Ser. No. 08/145,681, filed on Oct. 28, 1993, which is a continuation-in-part of application Ser. No. 07/967,947, filed Oct. 27, 1992, now abandoned, which in turn is a continuation of application Ser. No. 07/348,270, filed May 5, 1989, now abandoned. This application is also a continuing application of U.S. Ser. No. 08/250,308, filed May 27, 1994, which is a continuation-in-part of application Ser. No. 07/873,304 filed Apr. 24, 1992, now abandoned. The disclosure in all of the above-mentioned patent applications are herein incorporated by reference, with particular reference to the Figures and Examples in these patent applications.

FIELD OF THE INVENTION

The present invention relates generally to the field of iron-binding glycoproteins and related polypeptides, namely lactoferrins. More specifically, the present invention relates to the recombinant production of various lactoferrins and lactoferrin polypeptide fragments in Aspergillus, especially *Aspergillus awamori, niger* and *oryzae*.

BACKGROUND DISCLOSURES

In co-pending patent application U.S. Ser. No. 08/145,681, the cDNA sequences for human lactoferrin was disclosed. Additionally, in the same co-pending patent application U.S. Ser. No. 08/145,681, the cDNA sequences for human lactoferrin were used to produce human lactoferrin in a variety of different organisms, including various fungi, such as *Saccharomyces cerevisiae, Aspergillus nidulans,* and *Aspergillus oryzae*.

DESCRIPTION OF THE PRIOR ART

Lactoferrin (LF) is an iron-binding glycoprotein found in milk and other secretions and body fluids. LF is a member of the transferrin family and is involved in iron binding and delivery in mammals.

LF was originally discovered in milk where it can be secreted at levels up to 7 grams/liter in colostrum. Since that original discovery, LF has been detected in other secreted fluids of humans and other mammals. Those fluids include tears, saliva and mucosal secretions and also in the secondary granules of polymorphonuclear leukocytes.

LF is a 78 kilodalton (kDa) glycoprotein having a bilobal structure with a high degree of homology between the C and N terminal halves which is evident in both the amino acid sequence and the three dimensional structure levels. Each of these lobes can reversibly bind one ferric iron with high affinity and with the concomitant binding of bicarbonate. The biological functions of lactoferrin include static and cidal effects against microbial pathogens, transport of iron, promotion of cell growth, regulation of immune cell function and inflammatory response, and regulation of myelopoiesis. It has been found that the deglycosylated protein retains all biological functions of native LF.

The bactericidal domain from lactoferrin has a broad spectrum of antimicrobial action. Bellamy, W. M. et al., *J. App. Bact.* 73, 472–479 (1992). Although Bellamy et al. report that bovine lactoferrin isolated from milk can provide commercial quantities of the bovine polypeptide by pepsin digestion, the materials used in both studies had a maximum purity of 95%. Bellamy, et al. do not provide information for the large scale production of synthetic human or bovine lactoferrin or lactoferrin polypeptides. Neither does Bellamy et al. discuss methods which provide the ability to produce peptides that are not available by enzyme digestion.

Filamentous fungi have been employed as hosts in the industrial production of extracellular glycoproteins. Certain industrial strains are capable of secreting gram quantities of these proteins. In addition, filamentous fungi are able to correctly perform post-translational modifications of eukaryotic proteins and many proteins have U.S. Food and Drug Administration approval. Furthermore, large scale fermentation technology and downstream processing experience is available. However, there have been reports that lactoferrin is toxic to certain fungi (Valenti, et al, *FEMS Microbiology Letters*, 33:271–275 (1986); Epstein, et al, *Reviews of Infectious Diseases*, 6:96–106 (1984);Soukka, et al, *FEMS Microbiology Letters,* 90:223–228 (1992)) and consequently, workers have not employed fungi universally, particularly for production of lactoferrins.

Production of lactoferrins in filamentous fungi, particularly, Aspergillus, was first reported by the present inventors (Ward, et al, *Gene,* 122:219–223 (1992); Ward, et al., *Biotechnology,* 10:784–789 (1992); Conneely et al., *Production of Recombinant Human Lactoferrin,* PCT/US 93/22348, International Application Number PCT/US93/03614, having a priority date of Apr. 24, 1992 and published on Nov. 11, 1993; and Conneely, et al., U.S. Ser. No. 08/250/308 filed May 27, 1994, which is a continuing application of U.S. Ser. No. 07/873,304, filed Apr. 24, 1992, now abandoned, all of which are incorporated herein by reference). However, while these processes were a significant breakthrough, they have been limited in their ability to effectively produce large commercial quantities of lactoferrin.

Currently, there is a need for a more efficient and economical way to produce LF, either human, bovine, or porcine, in addition to a way to produce lactoferrin polypeptides. Consequently, there is also a need for the development of an efficient and commercial method for the production of human lactoferrin for nutritional and therapeutic applications and for further investigation into its mechanism of action. The subject invention satisfies this need by providing the production of lactoferrins and lactoferrin polypeptide fragments using the host cells Aspergillus in connection with novel vector constructs and especially methods of producing lactoferrins in Aspergillus host cells, which enables them to produce commercial amounts of recombinant lactoferrins and lactoferrin polypeptide fragments.

SUMMARY OF THE INVENTION

The subject invention provides for the production of lactoferrins and lactoferrin polypeptide fragments using the host cells Aspergillus in combination with novel plasmid constructs. More specifically, the subject invention provides novel vector constructs capable of producing lactoferrins and lactoferrin polypeptide fragments in Aspergillus host cells. More particularly, the subject invention provides for novel plasmid constructs suitable for use with Aspergillus and especially *Aspergillus awamori, niger* and *oryzae* host cells, which enables them to produce large amounts of recombinant lactoferrins and lactoferrin polypeptide fragments.

The subject invention also provides for a novel expression plasmid vector construct which enables the production of lactoferrin and lactoferrin polypeptide fragments. The plasmid vector constructs contain two important components which provide such high levels of lactoferrin to be produced. In addition to a promoter, cDNA coding for protein of choice, a signal sequence, transcription termination sequence and a selectable marker, the plasmid vector construct additionally contains (a) 5' half of a highly expressed endogenous gene whose product is secreted from the Aspergillus cell, and (b) a linker sequence whereby there is an endogenous proteolytic enzyme for the linker sequence. The product of this novel plasmid vector construct is a fusion protein comprised of half of the highly expressed gene fused to lactoferrin or lactoferrin polypeptide fragment. The fusion protein thereafter is processed by an endogenous proteolytic enzyme which is preferably specific for the Kex2 peptidase cleavage site. For example, if the glucoamylase promoter from *A. awamori* is used, the vector would also contain the 5' half of the *A. awamori* glucoamylase gene. The lactoferrin produced would be fused to one-half of the glucoamylase gene and would then be processed by an endogenous *A. awamori* proteolytic enzyme which is specific for the Kex2 peptidase cleavage site. As another example, if the glucoamylase promoter from *A. niger* is used, the vector would also contain the 5' half of the *A. niger* glucoamylase gene. The fusion product produced by the vector construct (LF fused to one half of glucoamylase gene) would then be processed by an *A. niger* endogenous proteolytic enzyme specific for the Kex2 peptidase cleavage site releasing the desired lactoferrin protein or LF polypeptide fragment. Also, if *A. oryzae* cells were to be used, the vector construct would contain the *A. oryzae* promoter from the α-amylase gene and a portion of the *A. oryzae* α-amylase gene. The vector would be used to transform *A. oryzae* cells and the fused product (LF fused to half of the α-amylase gene) would be processed by an *A. oryzae* endogenous proteolytic enzyme specific for the Kex 2 peptidase cleavage site yielding the desired LF or LF polypeptide fragment.

Thus, the subject invention provides a novel vector plasmid construct for producing LF or LF polypeptide fragments in commercial quantities in any strain of Aspergillus.

Another embodiment of the subject invention comprises the following components operably linked from 5' to 3' to form an expression plasmid vector:

(a) a promoter;

(b) a signal sequence;

(c) 5' portion of a highly expressed endogenous gene whose product is secreted from Aspergillus cells (i.e. glucoamylase gene);

(d) a linker sequence; and (e) a nucleotide sequence corresponding to the desired lactoferrin or lactoferrin polypeptide fragment.

The above DNA sequences (a) through (e) are then cloned together to form a plasmid. The resulting expression plasmid is used to transform Aspergillus cells which will express the lactoferrin protein or lactoferrin polypeptide fragment (corresponding to the lactoferrin nucleotide sequence inserted into the expression plasmid) fused to one half of the highly expressed endogenous gene, for example, the glucoamylase gene. The LF or LF polypeptide fragment is processed by an endogenous proteolytic enzyme specific for the Kex2 peptidase cleavage site.

Another embodiment of the claimed invention is a process for producing lactoferrin which comprises culturing a transformed Aspergillus fungal cell containing a recombinant plasmid, wherein said plasmid comprises a nucleotide sequence which codes for lactoferrin proteins or lactoferrin polypeptide fragments, wherein said transformed Aspergillus fungal cells are cultured in a suitable nutrient medium until lactoferrin protein is formed as a fusion product and then processed via an endogenous proteolytic enzyme specific for Kex2 peptidase cleavage site, wherein said processed lactoferrin is secreted into the nutrient medium and wherein said lactoferrin is isolated or recovered from the nutrient medium.

The present invention is further defined in that the above mentioned plasmid vector further comprises a promoter, a signal sequence, a 5' portion of the glucoamylase gene, a linker sequence, a transcription termination sequence, and a selectable marker gene. For the purpose of this invention, "linker sequence" and "protease recognition sequence" are used interchangeably.

This expression vector is further defined wherein the promoter which is selected from the genes of the group consisting of alcohol dehydrogenase, α-amylase, glucoamylase, and benA and wherein the promoter is further defined to be from *A. awamori* glucoamylase gene.

The above described process is further defined wherein said promoter is from the glucoamylase gene, wherein said promoter is from the glucoamylase gene of *A. awamori* and wherein the signal sequence is from the *A. awamori* glucoamylase gene. This process is further defined wherein the above described signal sequence further comprises a 5' portion of the glucoamylase gene that is from *A. awamori*.

The above described process can be further defined wherein said promoter is derived from the glucoamylase gene, wherein said promoter is from the glucoamylase gene of *A. niger* and the signal sequence is from the *A. niger* glucoamylase gene. This process is further defined wherein the above described signal sequence further comprises a 5' portion of the glucoamylase gene that is from *A. niger*.

The above described process is still further defined wherein said promoter is from the α-amylase gene, wherein said promoter is from the α-amylase gene of *A. oryzae* and wherein the cDNA sequence corresponding to the signal sequence is from the *A. oryzae* α-amylase gene. This process is further defined wherein the above described signal sequence further comprises a 5' portion of the α-amylase gene that is from *A. oryzae*.

The above described process is further defined wherein the linker sequence is a peptidase recognition sequence. This invention is yet further defined wherein the linker sequence encodes the Kex2 peptidase recognition sequence. For the purpose of this invention, Kex2 peptidase recognition sequence and Kex2 peptidase cleavage site are the same.

The above described process is further defined wherein the transcription termination sequence is selected from the genes of the group consisting of alpha-amylase, glucoamylase, alcohol dehydrogenase and benA. This invention is yet further defined in that the transcription termination sequence is from the glucoamylase gene and wherein the transcription termination sequence is from the glucoamylase gene of *A. niger*

The above described process is further defined wherein the selectable marker gene is selected from the genes of the group consisting of pyr4, pyrG, amdS, argB, trpC, and phleomycin resistance. This process is yet further defined in that the selectable marker is from the phleomycin resistance gene.

This invention is further defined wherein the lactoferrin protein or lactoferrin polypeptide fragment is human, porcine or bovine lactoferrin protein. The invention is further defined and wherein any lactoferrin product has been deglycosylated.

Another embodiment of the present invention is a plasmid which consists essentially of DNA encoding the amino acids of a human lactoferrin and a plasmid vector for the expression of the DNA in the cell wherein said plasmid is used for expressing the DNA of a human lactoferrin in *Aspergillus awamori* fungal cells. A particular preferred plasmid is defined as one having the characteristics of ATCC Accession Number 74290 and designated Awa LF 24-1 wherein Awa LF 24-1 is *Aspergillus awamori* transformed with expression plasmid pPLF-19 containing DNA encoding human lactoferrin, i.e., Seq. I.D. Listing No. 1 of U.S. Ser. No. 08/145,681, the latter of which is incorporated herein by reference. Another embodiment of this invention is *Aspergillus awamori* fungal cells containing the above described plasmid.

Yet a specific embodiment of the present invention is a process comprising culturing a transformed *Aspergillus awamori, niger* and *oryzae* fungal cell containing a recombinant plasmid, wherein said plasmid comprises a plasmid vector containing:

(a) a promoter from the *A. awamori* glucoamylase gene;

(b) a signal sequence from the *A. awamori* glucoamylase gene;

(c) a 5' portion of a highly expressed endogenous gene, for example, the *A. awamori* glucoamylase gene;

(d) a linker sequence encoding kex2 peptidase cleavage site;

(e) DNA encoding the amino acids for human lactoferrin;

(f) a transcription termination sequence from the *A. niger* glucoamylase gene; and (g) a phleomycin resistance selectable marker gene;

wherein said transformed *Aspergillus awamori, niger* and *oryzae* fungal cells are cultured in a suitable nutrient medium until lactoferrin protein is formed as a fusion product and then processed by an endogenous proteolytic enzyme specific for the Kex2 peptidase cleavage site, wherein said lactoferrin protein is the product of the cDNA encoding the amino acid sequence of human LF and, wherein lactoferrin is secreted into the nutrient medium and isolated therefrom. For the purpose of this invention, "Kex2 peptidase cleavage site" and "kex2 peptidase recognition sequence" are used interchangeably.

Another embodiment of this invention is a method of isolating lactoferrin from fungal nutrient medium comprising culturing a transformed Aspergillus fungal cell containing a recombinant plasmid vector, wherein said plasmid vector comprises a promoter, signal sequences, a 5' portion of the glucoamylase gene, linker sequences, DNA encoding the amino acids of human lactoferrin, transcription termination sequences, and a selectable marker gene and wherein said transformed Aspergillus fungal cells are cultured in a suitable nutrient medium until lactoferrin protein is formed as a fusion product and then processed by an endogenous proteolytic enzyme, and wherein lactoferrin is secreted into the nutrient medium and isolated therefrom.

The above described method of isolating lactoferrin from fungal nutrient medium is further defined wherein the plasmid vector contains a promoter from the *A. awamori* glucoamylase gene, a signal sequence from *A. awamori* glucoamylase gene, a 5' portion of the *A. awamori* glucoamylase gene, a linker sequence encoding kex2 peptidase cleavage site, a transcription termination sequence from the *A. niger* glucoamylase gene, and a phleomycin resistance selectable marker gene.

Another embodiment of this invention is a novel recombinant expression plasmid vector comprising the following components operably linked from 5' to 3':

1) promoter from the *A. awamori* glucoamylase gene;

2) signal sequence from the *A. awamori* glucoamylase gene;

3) 5' portion of the *A. awamori* glucoamylase gene;

4) linker sequence encoding kex2 peptidase cleavage site;

5) a nucleotide sequence encoding the amino acids for human lactoferrin or lactoferrin polypeptide fragments;

6) transcription termination sequence from the *A. niger* glucoamylase gene; and 7) phleomycin resistance selectable marker gene.

The invention also comprises production of the complete and partial sequences of the cDNA for human, bovine or porcine lactoferrins and substitution analogs or allelic variations thereof which code for biologically active polypeptides having homology with a portion of lactoferrin, especially those that are not available from enzyme digests of natural lactoferrins, the method of making polypeptides by use and expression of partial cDNA sequences, and the polypeptide products produced by the methods of this invention. The desired partial sequences can be produced by restriction enzyme cleavage, as for example at the cleavage sites indicated in FIGS. 13, 14, and 15. FIG. 13 through 15 shown restriction enzyme cleavage sites for the human, bovine and porcine LF cDNA sequence, respectively. The partial sequences may also be synthesized, obtained by PCR amplification, by a combination of cleavage, ligation and synthesis, or by other methods known to those skilled in the art.

The cDNA sequence for porcine lactoferrin (Lydon, J. P., et al., *Biochem. Biophys. ACTA*, 1132: 97–99 (1992); Alexander, L. J., et al., *Animal Genetics*, 23:251–256 (1992)) and for bovine lactoferrin (Mead, P. E., et al., *Nucleic Acids Research*, 18:7167 (1990); Pierce, A., et al., *Eur. J. Biochem.*, 196:177–184 (1991)) have since been determined and reported in the literature. The references containing the cDNA sequences for bovine and porcine lactoferrin are herein incorporated into this patent application by reference.

Fragments of polypeptides derived from lactoferrin are also known to be biologically active and they may be produced by the method of the present invention. An N-terminal human lactoferrin fragment, including a bactericidal domain of hLF, was isolated from a pepsin digest of intact hLF. Bellamy, W. M., et al., *Biochem. Biophys. ACTA*, 1121:130–136 (1992). Synthetic 23 and 25 amino acid polypeptides were synthesized and found to have activities similar to the fragment derived by pepsin digestion. The synthesis details, yields and purity of the synthetic peptide were not reported. Bellamy et al. do not provide a practical route to large scale production of the bovine or human lactoferrin polypeptides free of the contaminants resulting from isolation from natural products. These polypeptides fragments may be produced by the method of the present invention, and form a preferred embodiment thereof.

The amino acid sequences and corresponding cDNA sequences for the following disclosures are incorporated herein by reference:

(a) Powell, et al., Nucleic Acids Research, 18 (13): 4013 (1990; mammary);

(b) Rey, et al., Nucleic Acids Research, 18 (17): 5288 (1990; mammary);

(c) Rado, et al., Blood, 70 (4): 989–993 (1987; neutrophil);

(d) Stowell, et al., Biochem. J., 276:349–355 (1991);

(e) Panella, et al., Cancer Research, 51:3037–3043 (1991; mammary); and (f) Johnston, et al., Blood, 79 (11): 2998–3006 (1992; leukemic).

Any of these sequences, or modified forms of these sequences may be used in the method of the present invention, the preferred sequence is one having the polypeptide sequence reported to GenBank by the present inventors, and having Accession No. A31000, all of which are incorporated herein by reference.

BRIEF DESCRIPTION OF THE DRAWINGS

So that the manner in which the above recited features, advantages, and objects of the invention, as well as others which will become clear, are obtained and can be understood in detail, more particular descriptions of the invention briefly summarized above may be had by reference to certain embodiments thereof which are illustrated in the appended drawings. These drawings form a part of this specification.

It is to be noted, however, that the appended drawings illustrate preferred embodiments of the invention and therefore not to be considered limiting of its scope. The invention may admit to other equally effective equivalent embodiments.

FIG. 4 presents the results from N-terminal sequencing of the first 10 amino acids of recombinantly produced hLF in *A. awamori*.

FIG. 13 shows restriction enzyme cleavage sites for the human LF cDNA sequence.

FIG. 14 shows restriction enzyme cleavage sites for the bovine LF cDNA sequence.

FIG. 15 shows restriction enzyme cleavage sites for the porcine LF cDNA sequence.

FIG. 16C represents N-terminal amino acid sequence of recombinant hLF produced in *A. oryzae*.

DETAILED DESCRIPTION OF THE INVENTION

Definitions

Figure 1A:
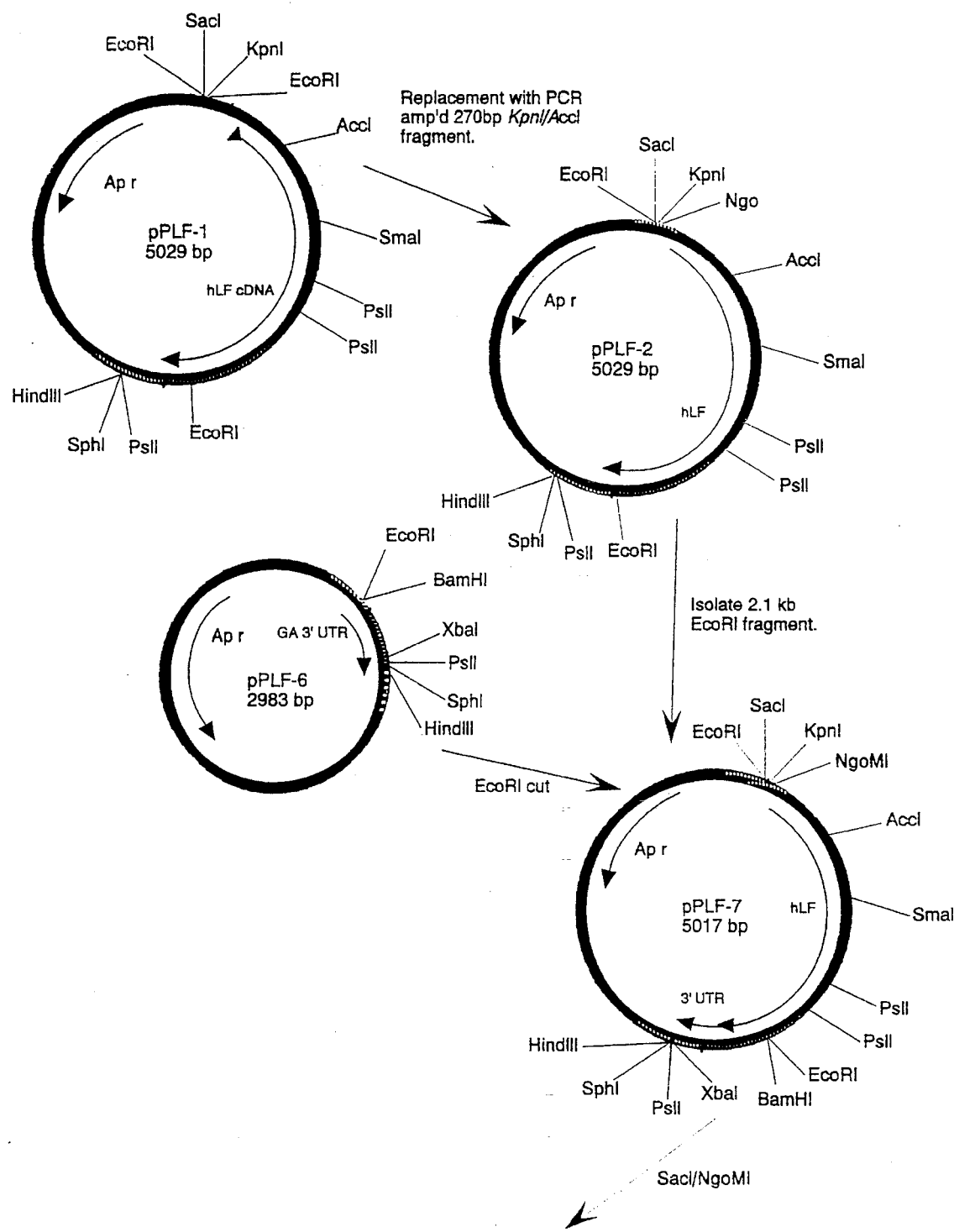
FIG. 1 shows the construction of the plasmid vector containing the hLF cDNA for expression in *Aspergillus awamori* designated "pPLF-19." Abbreviations used in this figure are as follows: Apr: ampicillin resistance; hLF: human lactoferrin; GA: glucoamylase; pGA: promoter from glucoamylase; GA 3'UTR: glucoamylase 3' untranslated region; s.s.: signal sequence; phleo r: phleomycin gene resistance. Example 4 details the construction of this vector.
Figure 1B:
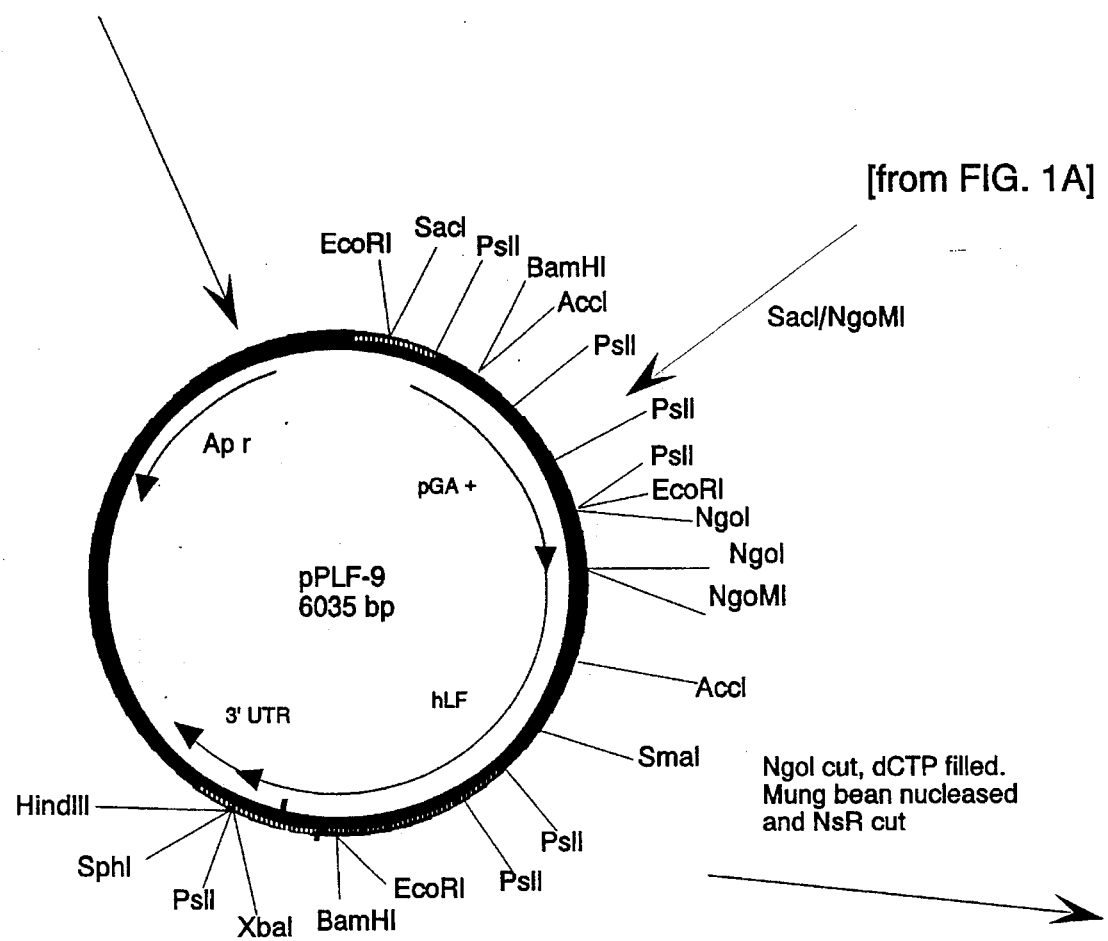
Figure 1C:
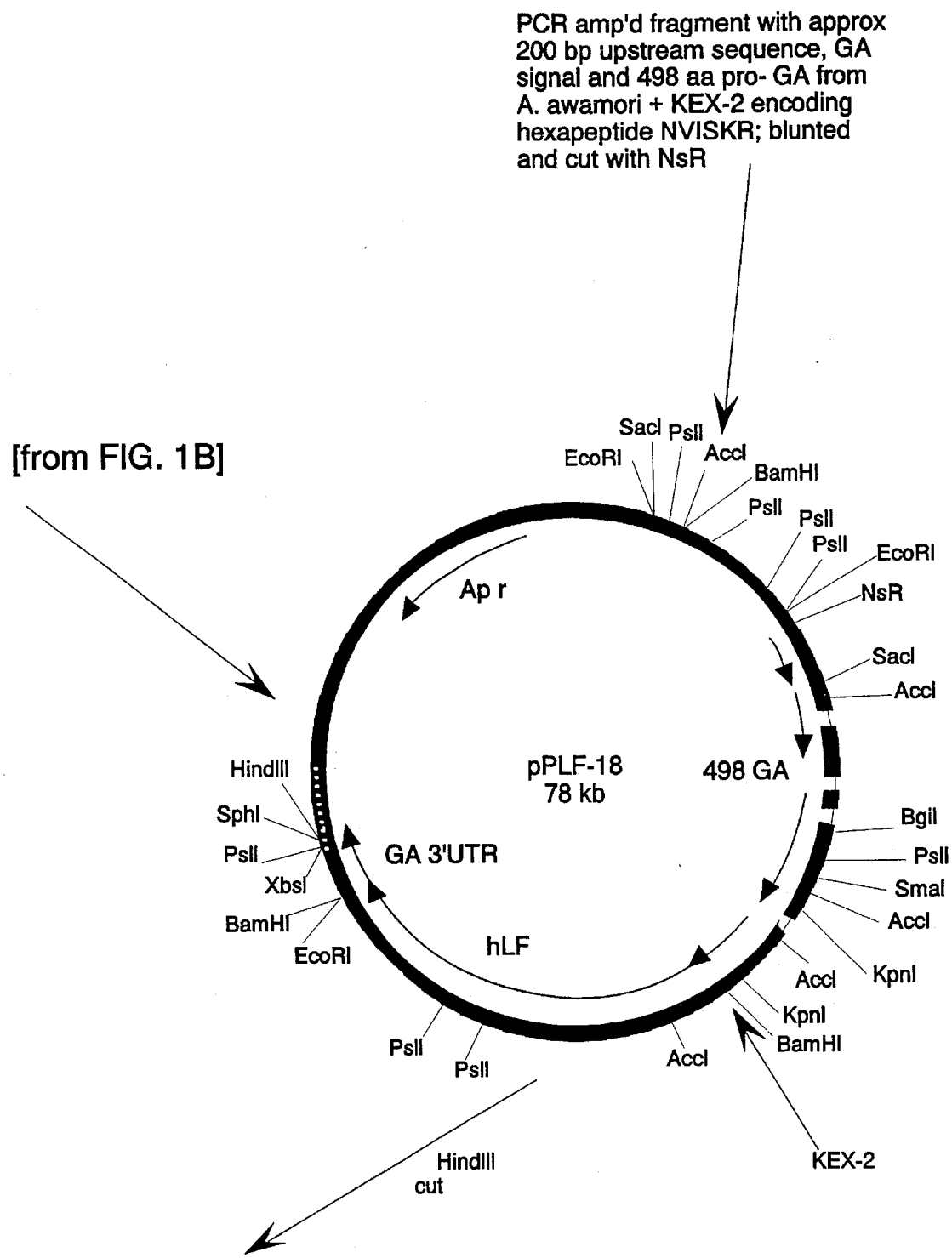
Figure 1D:
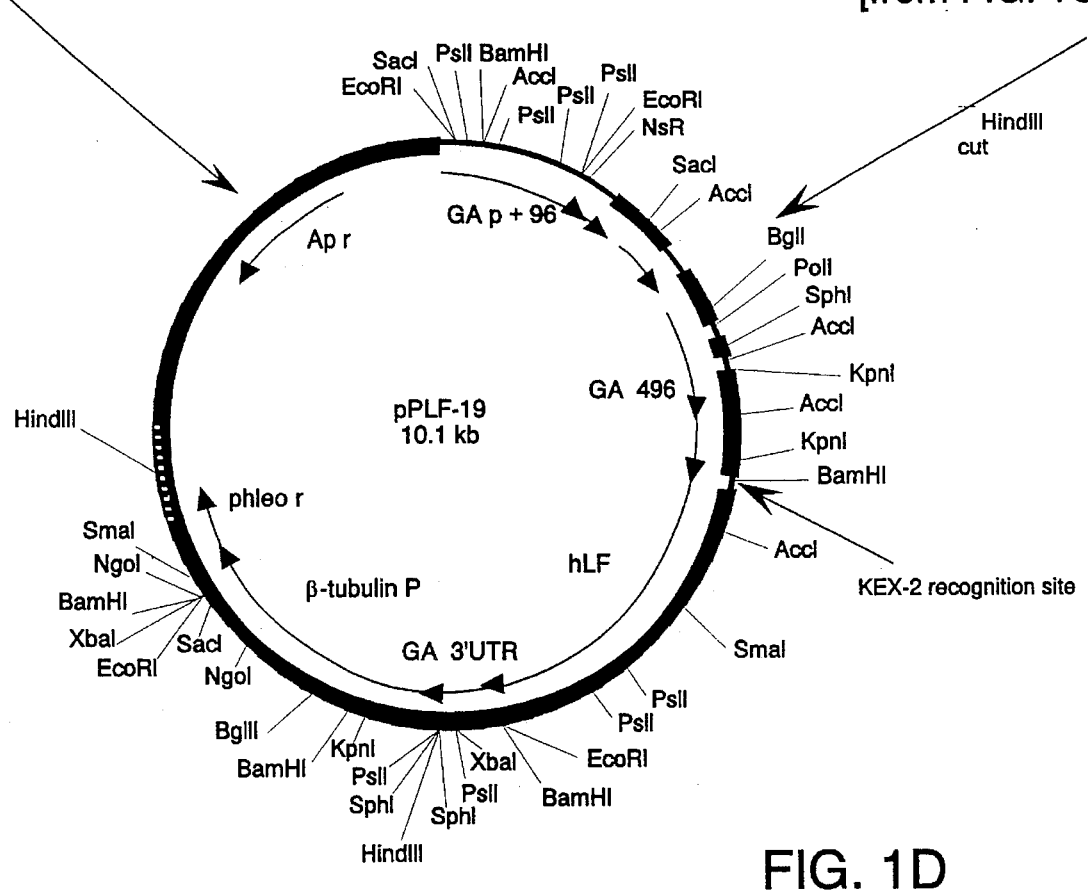

For the purpose of the subject application, the following terms are defined for a better understanding of the invention.

The term "transferrin family" means a family of iron binding proteins including serum transferrin, ovotransferrin and lactoferrin. These proteins are all structurally related.

The term "lactoferrin" means a member of the transferrin family which is found in milk and other secretions. Lactoferrin is an 78 KD iron binding protein.

Additionally, the term "domain" is used to define a functional fragment of the lactoferrin protein or lactoferrin polypeptide which includes all or part of the molecular elements which effect a specified function such as iron binding, bactericidal properties, receptor binding, immune stimulation, etc.

The term "polypeptide" or "polypeptides" means several amino acids attached together to form a small peptide or polypeptide.

The term "substitution analog" or "allelic variation" or "allelic variant" all refer to a DNA sequence which one or more codons specifying one or more amino acids of lactoferrin or a lactoferrin polypeptide are replaced by alternate codons that specify the same amino acid sequence with a different DNA sequence. Where "substitution analog" or "allelic variant" refers to a protein or polypeptide it means the substitution of a small number, generally five or less amino acids as are known to occur in allelic variation in human and other mammalian proteins wherein the biological activity of the protein is maintained. Amino acid substitutions have been reported in the sequences of several published hLF cDNAs which are most likely due to allelic variations. See FIG. 16, and discussion related to this Figure.

The term "vector(s)" means plasmid, cosmid, phage or any other vehicle to allow insertion, propagation and expression of lactoferrin cDNA.

The term "host(s)" means any cell that will allow lactoferrin expression.

The term "promoter(s)" means regulatory DNA sequences that control transcription of the lactoferrin cDNA.

The term "multiple cloning cassette" means a DNA fragment containing unique restriction enzyme cleavage sites for a variety of enzymes allowing insertion of a variety of cDNAs.

The term "transformation" means incorporation permitting expression of heterologous DNA sequences by a cell.

The term "iron binding capacity" means ability to bind Fe. Fully functional human lactoferrin can bind two atoms of iron per molecule of LF.

The term "biological activity or biologically active" means functional activity of lactoferrin as measured by its ability to bind iron, or kill microorganisms, or retard the growth of microorganisms, or to function as an iron transfer protein, or bind to specific receptors, stimulate immune response or regulate myelopoiesis.

The promoter useful in the present invention may be any that allows regulation of the transcription of the lactoferrin cDNA. Preferably, the promoter is selected from the group of alcohol dehydrogenase, α-amylase and glucoamylase genes. Thus, many different promoters are known to those skilled in this art but the inventors prefer to use the glucoamylase promoter isolated from *A. awamori*.

Many different signal sequence and sources of these signal sequences are known to those skilled in this art but the inventors prefer to use the glucoamylase signal sequence plus the 5' portion of the glucoamylase gene derived from *A. awamori*.

The signal sequence useful in the present method may be any that contains a translation initiation codon and secretory signal together with part of a coding region for any highly expressed endogenous gene.

The linker sequence useful in the present method contains a recognition sequence for any proteolytic enzyme, preferably the Kex2 peptidase recognition sequence.

The transcription termination sequence useful in the present method may be any that allows stabilization and correct termination of the lactoferrin mRNA transcripts. Preferably, the transcription termination sequence is derived from the α-amylase, glucoamylase, alcohol dehydrogenase or benA genes. Thus, many different transcription termination sequences are known to those skilled in this art but the inventors prefer using the 3' untranslated region from the glucoamylase gene from *A. niger*.

The selectable marker gene useful in the method of the present invention may be any that permits isolation of cells transformed with a lactoferrin cDNA plasmid. Preferably, the selectable marker gene is selected from pyr4, pyrG, argB, trpC, amdS, or phleomycin resistance genes. Thus, many different selectable markers are known to those skilled in this art but the inventors prefer to use the phleomycin resistance gene.

Additionally, recombinant production of lactoferrin protein has been described above in its preferred embodiments. LF can be produced in a number of sources: cell sources such as Aspergillus; *Saccharomyces cerevisiae, Kluyveromyces lactis,* or *Pichia pastorsis;* insect cells such as SF9; and mammalian cells such as Cos cells.

The cells, preferably eukaryotic cells, useful in the present invention are any that allow for integration of a vector, preferably a plasmid comprising the lactoferrin cDNA and expression of the lactoferrin cDNA. Preferably, the eukaryotic cells are filamentous fungal cells or insect cells. Insect cells such as SF9 are useful in the method of the present invention. More preferably, the cells are fungal Aspergillus cells. Most preferably, the eukaryotic cells useful in the present invention are Aspergillus strains, such as *A. oryzae A. niger, A. nidulans* and *A. awamori*.

The confirmation of the cDNA sequence encoding hLF and the deduced amino acid have been proven by multiple confirmation procedures.

These are:
1. Multiple sequence analyses.
2. Transcription and translation of hLF protein from the cDNA with positive identification using an anti-hLF antibody.

The cDNA sequence encoding hLF can be used to prepare recombinant human lactoferrin, thus making available a source of protein for therapeutic and nutritional applications. The confirmed cDNA sequence can be used in an appropriate cloning vehicle to replicate the cDNA sequence. Also, the cDNA can be incorporated into a vector system for human lactoferrin production. Other lactoferrin DNA sequences can be substituted for the human lactoferrin cDNA sequence to provide bovine, porcine, equine or other lactoferrins. Partial cDNA sequences can also be employed to give desired lactoferrin derived polypeptides. The expression systems of the invention can be used to provide lactoferrin derived polypeptides that are not available by enzymatic digestion of naturally occurring lactoferrin. The subject invention further provides an expression system for producing lactoferrin and lactoferrin related polypeptides in Aspergillus cells. The invention allows for the production of lactoferrin free of lactoperoxidase, lysozyme, or other proteins that are contaminants of lactoferrin isolated from milk or other natural sources. This invention is not limited to any particular uses of the human cDNA sequence or production of lactoferrin of other species from the appropriate DNA sequences.

The recombinant LF being a protein derived by recombinant techniques can be used in a variety of applications. The human gene can be transferred to mammalian systems such as cows and other agriculturally important animals and expressed in milk. The incorporation of a lactoferrin gene and expression in the milk of animals can combat an iron deficiency typical in piglets. The inclusion of a lactoferrin gene with expression should improve an animal's disease resistance to bacterial and viral infection. The tissue specific expression of human lactoferrin in mammary glands, for instance, would impart the bacteriocidal and virucidal benefit of the expressed gene to young feeding on the milk and would provide a production means for the secreted protein for therapeutic use.

The LF produced by recombinant methods of the subject invention can be used in a variety of products including human or animal foods, as therapeutic additives to enhance iron transport and delivery, and for the virucidal and bacteriocidal qualities, as additives for eyedrops, contact lens and other eye care solutions, topical skin care products, eardrops, mouthwashes, chewing gum and toothpaste. The recombinant LF would provide a safe, naturally occurring product which can be topically applied as well as ingested safely. The bactericidal lactoferrin polypeptides are useful as preservatives in the above listed products, and as therapeutic anti-infection agents. The iron binding polypeptides are useful as iron or other metal ion carrier proteins for nutritional and therapeutic uses, and as bacteriostats and bactericides, especially in products of the types listed above. Each protein may also be used as a nutrition supplement and as a source of amino acids and metals.

Different components of plasmid expression vectors as used to produce recombinant human lactoferrin are presented below and are not meant to be limitations of the present invention in any form. Many different promoters are known to those skilled in this art but the inventors prefer to use the glucoamylase promoter isolated from *A. awamori*. Many different signal sequence and sources of these signal sequences are known to those skilled in this art but the inventors prefer to use the glucoamylase signal sequence plus the 5' portion of the glucoamylase gene derived from *A. awamori*. Many different linker sequences are known to those skilled in this art but the inventors prefer to use a synthetic linker which codes for the Kex2 peptidase cleavage site. Many different transcription termination sequences are known to those skilled in this art but the inventors prefer using the 3' untranslated region from the glucoamylase gene from *A. niger*. Many different selectable markers are known to those skilled in this art but the inventors prefer to use the phleomycin resistance gene.

One of ordinary skill in this art understands and appreciates that a variety of different parameters can be modified while not affecting the quantity or quality of lactoferrin produced by the claimed invention. The following is a list of such parameters that can be altered and yet still not affect the amount and quality of lactoferrin produced: temperature; pH; nutrients required; scale-up considerations; type of equipment used; ratio of oxygen/air used; use of stirred vs. static systems; harvest times, etc.

Different growth and production conditions can be used for the expression of recombinant human lactoferrin in *Aspergillus awamori*. The following descriptions are presented for the purposes of illustrating various conditions which can be used for the expression of hLF in *Aspergillus awamori* and are not meant to be limitations of the present invention in any form. Presented below is a general outline of the fermentation production process and the process used to recover the produced lactoferrin. One of ordinary skill in this art understands that the protocol may be changed or modified in minor ways in order to enhance the production of the desired lactoferrin or lactoferrin polypeptide.

The following examples are given for the purposes of illustrating various embodiments of the present invention and are not meant to be limitations of the present invention in any form.

EXAMPLE 1

CONSTRUCTION OF EXPRESSION VECTOR pPLF-19 FOR THE EXPRESSION OF RECOMBINANT HUMAN LACTOFERRIN IN *ASPERGILLUS AWAMORI*.

This example demonstrates the construction of an expression vector which is used to express recombinant human lactoferrin in Aspergillus awamori.

I. STRAINS, PLASMIDS, ENZYMES AND MEDIA

A. Bacterial and fungal strains

*Aspergillus awamori* strain ATCC 22342 was used as the host strain for the heterologous expression of human lactoferrin. *E. coli* strain DH5α was used in the construction of the human lactoferrin expression vector, pPLF-19.

B. Plasmids

The plasmids pUC19 and pGEM4 (Promega, Madison, Wis.) were used in various cloning steps leading to the final construction of the human lactoferrin expression plasmid pPLF-19.

The phleomycin resistance vector, pLO-3, which contains the phleomycin resistance gene (a phleomycin binding protein gene from *Streptoalloteichus hindustanus*) coupled to a yeast cytochrome C1 terminator was derived from the plasmid pUT713 (CAYLA, Toulouse-Cedex, FR). It is expressed in fungus by the β-tubulin promoter from *A. niger*.

C. Enzymes

Restriction enzymes were obtained from New England Biolabs (Beverly, Mass.). T4 Ligase, T4 Polymerase, T4 Kinase, and the Klenow fragment from *E. coli* DNA Polymerase I were purchased from Bethesda Research Laboratories (BRL, Gaithersburg, Md.). Mung Bean Nuclease was obtained from Stratagene (La Jolla, Calif.). Taq Polymerase was obtained from Promega Corporation (Madison, Wis.). DNA sequencing of plasmid constructs was accomplished using the Sequenase Version 2.0 T7 DNA Polymerase enzyme and kit (United Stated Biochemicals, Cleveland, Ohio). Novozym 234, a spheroplasting enzyme was purchased from Novo BioLabs (Bagsvaerd, Denmark).

D. General Growth Media

*E. coli* strains were grown in L-broth (Difco, Detroit, MI). Bacterial transformants were grown on L-broth plates containing 1.5% agar and 125 ug/ml ampicillin. Complete Media (CM) for growth of *A. awamori* in liquid is composed of: 50 ml of 20X Clutterbuck's salts (120 g $Na_2NO_3$, 10.4 g KCl, 10.4 g $MgSO_4 \cdot 7H_2O$, 30.4 g $KH_2PO_4$), 2.0 ml Vogel's Trace Elements (0.3M citric acid, 0.2M $ZnSO_4$, 25 mM Fe$[NH4]_2[SO_4]_2 \cdot 6H_2O$, 10mM $CuSO_4$, 3mM $SO_4^{-2}$, 8mM boric acid, 2mM $Na_2MoO_4 \cdot 2H_2O$), 5.0 g tryptone, 5.0 g yeast extract, 10 g glucose in one liter of distilled water). 1.5% agar was added for CM slants. PDA slants contained 39.0 g/L Potato Dextrose Agar in water (Difco, Detroit, Mich.), 10.0 g/L glucose, 10.0 g/L agar, 0.1 g/L MgSO4.7$H_2O$, 0.12 g/L $KH_2PO_4$, 0.25 g/L $(NH4)_2HPO_4$.

*A. awamori* lactoferrin-producing transformants were grown in KT-4 media: 150 g/L maltose, 60 g/L soyfine soymilk LF, 79.8 g/L $C_6H_5O_7Na_3.2H_2O$, 15 g/L, [NH4]$_2$SO$_4$, 1.0 g/L $NaH_2PO_4$, 2.05 g/L $MgSO_4.7H_2O$, 1.0 ml/L Tween 80, 2.0 ml/L antifoam 204; Dunn-Coleman et al., 1991, Bio/technology 9: 976–981.

E. ATCC Cell Deposit

The following transformed strain was deposited with the American Type Culture Collection pursuant to the provisions of the Budapest Treaty for the International Recognition of the Deposit of Microorganisms for the Purposes of Patent Procedure (American Type Culture Collection, 12301 Parklawn Drive, Rockville, Md. 20852) by the Applicants on Jul. 8, 1994: "Awa LF 24-1" is *Aspergillus awamori* transformed with the expression plasmid pPLF-19 containing the cDNA encoding human lactoferrin. This deposit was given ATCC Accession Number 74290. Applicants further agree to make this deposit available, without restriction to responsible third parties upon the granting of a patent from this application in the United States and comply with existing laws and regulations pertaining thereto, without limitation, except as to third parties adherence to applicants rights as prescribed by the claims of a patent issuing from this application.

II. METHODS

A. Construction of Human Lactoferrin Expression Plasmids

The following plasmids were constructed as progenitors to the final expression plasmid, pPLF-19. A diagram of the pPLF-19 construct is shown in FIG. 1. Abbreviations used in this figure are as follows: Apr: ampicillin resistance; hLF: human lactoferrin; GA: glucoamylase; pGA: promoter from glucoamylase; GA 3'UTR: glucoamylase 3' untranslated region; s.s.: signal sequence; phleo r: phleomycin resistance vector.

pPLF-1

The hLF cDNA was removed from pGEM4hLFc as a 2.3 kb SacI/HindIII fragment and subcloned into vector pUC-19. This subcloning was made in order to remove the cDNA from the pGEM4 backbone which contains an unwanted NgoMI site.

pPLF-2

The 5' end of hLF was modified to introduce a unique NgoMI site which can be used for a seamless addition of the glucoamylase (GA) promoter and signal sequence. Modification was made through PCR amplification of a 270 bp fragment spanning the 5' end of the mature lactoferrin coding sequence to a unique AccI site. The primers are listed below and are shown in SEQ. ID. No. 1 and 2, respectively.

```
              KpnI            NgoMI
5hLFFW  5'-G GGG TAC CGC  GCC GGC  CGT AGG AGA AGG AGT G
                          Gly Arg  Arg Arg Arg Ser
                              (Mature hLF N-term)

AccI
5hLFRV  5' - TTCGGTCCCGTAGACTTCCGCCGCT
```

The 270 bp fragment was amplified using Promega's Taq Polymerase with the following conditions: 1.25 to 5 mM MgCl2; 0.5 µM each primer (5hLFFW and 5hLFRV); 10 ng pGEM4hLFc as template. Cycled in Perkin Elmer 9600 Thermocycler: 1 @ 2 min, 96° C.; 30 @ 20 sec, 96° C./20 sec, 55° C./20.sec 72° C.; 1 @ 5 min, 72° C.

Fragments were isolated from agarose, enzymatically blunted and phosphorylated and subcloned into pUC 19 cut with SmaI to give plasmid pPUC270. Sequence of the amplified product was confirmed using M13 universal forward and reverse primers. The fragment was then removed from pPUC270 as a KpnIAccI fragment and used to replace the Kpn/AccI fragment of pPLF-1. The resulting plasmid was designated pPLF-2.

pPLF-6

A 280bp EcoRI/PstI fragment carrying the last 17 bp of hLF and 160 bp of GA 3' untranslated region (UTR) was subcloned from vector pAhLFG(+1) into EcoRI/PstI cut pUC19.

pPLF-7

The modified hLF gene of pPLF-2 was subcloned as an EcoRI fragment into vector pPLF-6. Correctly oriented plasmid (pPLF-7) contains full length mature hLF sequence with a unique NgoMI site immediately upstream and 160 bp of GA 3' UTR immediately downstream. GA promoter and signal sequences (see below) will be added to this vector.

The GA promoter and signal sequence was obtained by PCR amplification from genomic DNA isolated from *A. awamori* strain ATCC 22342. The forward primer spans a SacI site approximately 1.1 kb upstream of the GA signal sequence. Sequence of this primer was designed from published sequence for ATCC 10864 (GenBank Accession number X56442) and are shown in SEQ. ID. No. 3 and 4, respectively.

```
GAFW:  5'-TATGCAGAGGAGCTCTCCCCTGAC
                     SacI
```

The reverse primer incorporates an NgoMI site for attachment to hLF.

```
                      NgoMI
GARV: 5'-GAT TCC  GCC GGC  CAA CCC TGT GCA GAC GAG GC
             ←—  Ala Leu  Gly Thr Cys Val Leu ←—
                 ↑            (Processing point)
```

Correct sized fragments (1.1 kb) were amplified from ATCC 22342 genomic DNA using the following conditions: 2.5 mM MgCl$_2$,: 0.5 µM each primers (GAFW and GARV) and 100 ng genomic DNA. Cycling parameters were set at 1 @ 2 min, 95° C.; 30 @ 30 sec, 95° C./30 sec 60° C./45 sec, 72° C.; and 1 @ 5 min 72° C.

Amplified products were blunted, phosphorylated and subcloned into pUC-19 cut with SmaI. DNA sequence was generated from the 3' end of the amplified fragment to check for fidelity of amplification spanning the GA signal sequence region. Clones with verified sequence were used as the stock source of GA promoter and s.s. fragments.

pPLF-9

The PCR amplified GA promoter and signal sequences was ligated to vector pPLF-7 as a SacI/NgoMI fragment to give vector pPLF-9. Sequence generated through the junctions in one direction verified a clean ligation.

pPLF-18

The final GA expression plasmid contains the GA promoter, signal sequence, and sequence encoding 498 aa of pro-glucoamylase fused to hLF. The pro-hexapeptide of glucoamylase which ends in the dibasic KEX-2 recognition sequence Lys-Arg is engineered between the GA and hLF sequences. Presumably, the chimeric protein will be better recognized by the endogenous GA secretory pathway resulting in higher secretion titers of hLF. The KEX-2 linker should allow for accurate processing of hLF away from GA.

pPLF9 was cut first with NgoMI. The ends were filled with dCTP using Klenow fragment. Mung bean nuclease was then used to remove the remaining 5' overhangs to give a blunt end ready for an in-frame protein fusion. The vector was then cut with NsiI in order to accept the GA sequence which was PCR amplified as described below.

A fragment encoding the desired GA fragment was PCR amplified from strain ATCC 22342 with the following set of primers as shown in SEQ. ID. No. 5, 6, and 7, respectively.

GA-1.5' -GAATTCAAGCTAGATGCT

This forward primer spans bases 1–18 of published ATCC 22342 (NRRL 3112) GA upstream sequence (Nunberg et al. Mol Cell Bio 1984, p 2306–2315). This sequence lies approximately 50 bp upstream of a unique NstI site which was used in the construction.

|   | Ser | Val | Thr | Ser | Thr | Ser | Lys | Asn | Val | Ile | Ser |
|---|---|---|---|---|---|---|---|---|---|---|---|
| 5' - | AGC | GTG | ACC | TCG | ACC | AGC | AAG | AAT | GTG | ATT | TCC |
|   | AAG | CGC | | | | | | | | | |
|   | Lys | Arg | | | | | | | | | |
| KX2GA: 3' - | TCG | CAC | TGG | AGC | TGG | TCG | TTC | TTA | CAC | TAA | AGG |
|   | TTC | GCG-5' | | | | | | | | | |

This reverse primer sequence is complementary to the inserted pro-hexapeptide (underlined) encoding sequence and followed by the complement of pro-GA sequence encoding as 492–498.

The 2.0kb fragment was PCR amplified using Taq polymerase. 2.5 mM $MgCl_2$ was empirically determined to give the best amplification. The fragment was enzymatically blunted with Klenow in order to clean up potentially ragged ends leftover from the amplification. The blunted fragment was then cut with NsiI and then subcloned into manipulated vector pPLF-9 (see above) as an NsiI/blunt fragment to give plasmid pPLF-18. Sequence was verified through the GA/KEX-2/hLF junction through di-deoxy sequencing.

pPLF-19

A phleomycin resistance marker derived from CAYLA vector pUT713 (*Streptoalloteichus hindustanus* ble gene) and expressed from the *A. niger* tubulin promoter (pPLO-3) was added to pPLF-18 as a 2.3kb HindIII fragment to give the final expression plasmid pPLF-19.

B. DNA Transformation of *Aspergillus awamori* Strain ATCC 22342.

*Aspergillus awamori* strain ATCC 22342 was spheroplasted and transformed by a procedural modification of Tilburn et al, 1983, Gene 26: 205–221. Conidating cultures of *A. awamori* ATCC 22342 grown on Complete Media (CM) slants for four to seven days at 30° C. were scraped with 2 mls of NP40 water (0.005% Nonidet-40) to obtain a spore suspension. One ml of the spore suspension (approximately $1 \times 10^8$ spores) was added to 50 mls of CM and grown for 22 hours at 30° C., 200 rpm. Mycelia was collected by filtration through a double layer of cheesecloth and added to 50 mls of KCM buffer (Cantoral, et al., 1987, Biotechnology 5: 494–497; KCM: 0.7 M KCl, 10 mM MOPS, pH 5.8) with 5 mg/ml of Novozym 234 (Novo Biolabs, Bagsvaerd, Denmark) and incubated at 30° C., 90 rpm overnight for spheroplast generation.

The spheroplasts were harvested by filtration through a funnel packed with miracloth (Calbiochem; La Jolla, GA) and covered with cheesecloth into four 15 ml conical centrifuge tubes, then spun at 1800 rpm for ten minutes in a bench-top centrifuge. The pellets were gently resuspended in a total of 15 mls of KCM buffer and re-centrifuged. The pellet was again washed in 15 mls of KCM buffer, then resuspended in KCMC (KCM+50 mM $CaCl_2$) buffer to a final density of $5 \times 10^7$ cells/ml.

Five µgs of pPLfF19 plasmid DNA in 20 ul TE buffer (10 mM Tris-HCl, 1 mM EDTA, pH 8.0) was added to 200 ul of spheroplasts, and 50 ul of PCM (Cantoral et al; PCM: 40% PEG 8000, 10 mM MOPS, pH 5.8, 50 mM $CaCl_2$ [$CaCl_2$ added prior to use]) was gently pipetted into the DNA-spheroplast mixture and incubated on ice for thirty minutes.

One ml of freshly prepared PCM was added to the transformation mix, the mix was pipetted into 50 mls of Regeneration Agar (CM+1 .3M Mannitol, 3% agar) cooled to 50° C. that was then divided into five petri plates. Spheroplasts were allowed to regenerate 3 to 5 hours at 30° C. before overlaying with an equal amount of OL+120 ug/ml phleomycin(OL: 1% peptone, 1% agar; phleomycin [CAYLA; Toulouse, FR]). Putative transformants were transferred to PDA slants containing 125–150 ug/ml phleomycin.

C. Fermentation Conditions for Human Lactoferrin Expression in *Aspergillus awamori*

Spores from putative HLF-producing transformants were transferred from selective PDA slants to CM slants and grown for four days at 30° C. Conidia was harvested by scraping the slant with 1.5 ml of NP40 Water, and aliquot of $1 \times 10^8$ spores was added to 30 ml of KT-4 media in a 250 ml flask. Cultures were fermented for six days at 30° C. 200 rpm. Lactoferrin samples were collected by centrifuging one ml of fermentation broth at 3000 rpm for 15 minutes and assaying the retained supernatant.

D. Human Lactoferrin Assay

Lactoferrin was quantified by a modification of a Non-Competitive Avidin-Biotin Immunoassay developed by Vilja et al, 1985, J. of Imm. Methods 76: 73–83. A ninety-six well microtiter plate (U-Bottom Microtest III; Baxter, Chicago, Ill.) was coated with 100 ul of 0.1 ug/ml rabbit antihuman lactoferrin antibody (Sigma, St. Louis, Mo.) in Coating Buffer (0.1M Sodium Carbonate/Bicarbonate, pH 9.6), and was shaken overnight at 4° C.

The next day, the coating solution was removed, and the plates were washed three times with Washing Buffer (1X PBS pH 7.4, 0.5% Tween 20) prior to blocking with 250 ul of Diluent Buffer (1X PBS pH 7.4, 1% BSA [Fraction V, RIA grade, United States Biochemicals, Cleveland, Ohio], 0.05% Tween 20) for at least one hour at room temperature. The Diluent Buffer was discarded and 100 ul of diluted fermentation samples and known lactoferrin standards were added to the plate, which was then incubated for one hour at 37° C. The collected supernatant from the fermentation samples was diluted 1:1000 with Diluent Buffer prior to its addition to the microtiter plate. Lactoferrin standards consisted of human lactoferrin (Sigma, St. Louis, Mo.) diluted 1 to 1000 ng/ml in Diluent Buffer.

After reaction at 37° C. the samples were discarded and the plate was washed three times with Wash Buffer. One hundred ul of biotinylated anti-HLF antibody (Biotin-SP-Rabbit anti-hLF IgG, Jackson Immuno-Research Labs) diluted 1:7500 in Diluent Buffer from a 1 mg/ml stock was added to each well and incubated for one hour at 37° C.

The solution was discarded and the plate was washed three times with Wash Buffer before adding 100 ul of ABC reagent (Vectastain ABC Kit, Vector Labs, Burlingame, Ga.) and incubating the plate at 37° C. for one hour. Vectastain Reagent A was diluted 1:200 and Reagent B was diluted 1:400 in Diluent Buffer prior to combining both solutions and allowing them to preincubate one hour at room temperature before use.

The ABC solution was discarded and the plate was washed five times with Wash Buffer. One hundred ul of OPD Substrate Solution (10 ml Substrate Buffer [25 mM citric acid, 50 mM $Na_2HPO_4 7H_2O$, pH 5.0], 8 mg o-Phenylenediamine [Bethesda Research Labs, Gaithersburg, Md.], 100 ul 30% $H_2O_2$ [Sigma, St. Louis, Mo.]) was added and the plate was incubated in the dark for twenty minutes with gentle agitation at room temperature. After color development, 100 ul of 2M $H_2SO_4$ was added to stop the reaction. The plate was then read at 490 nm, and lactoferrin concentrations were determined by comparison to the known standards.

EXAMPLE 2

EXPRESSION AND PROCESSING OF hLF (pPLF-19) IN *ASPERGILLUS AWAMORI*

When the human lactoferrin expression cassette pPLF-19 is transformed into *A. awamori* 22342, secreted lactoferrin is detected in the media by both the ELISA assay and by Western blot analysis. One transformant, #19-254, produces approximately 250 mg/l of human lactoferrin (hLF). A more preferred transformant, Awa LF 24-1 (ATCC Accession No. 74290; #19–24.1) produces approximately 500 mg/l of human lactoferrin. Experiments improving yield and strain development are ongoing in order to increase the production of recombinant hLF in *A. awamori*. To date, the inventors have obtained titers >900 mg/l hLF produced in *A.awamori*-transformants containing strain Awa LF 24-1. The results are shown in the comparative Production Table below.

Since the pPLF-19 expression product is a chimeric protein made up of 498 amino acids of glucoamylase and the complete coding region of hLF separated by a KEX-2 cleavage site, SDS-PAGE, and silver staining, Western blot analysis and N-terminal sequencing were conducted to determine whether the protein was correctly processed.

A. Silver stained SDS-Polyacrylamide Gel Analysis of Recombinant Human Lactoferrin Purified from *Aspergillus awamori* Transformants.

Figure 2:
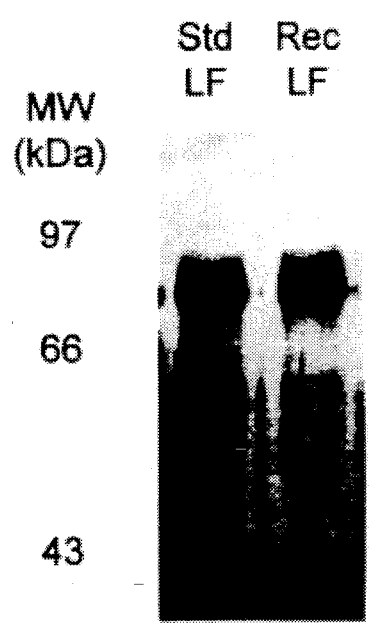
FIG. 2 is an SDS-PAGE of recombinant hLF (500 ng) purified from the growth medium of *Aspergillus awamori* transformants containing pPLF-19.

Recombinant human lactoferrin was purified from the growth medium of *Aspergillus awamori* transformants by ion-exchange chromatography using CM-Sephadex C50 (Stowell, K. M. et al., Biochem J., 276:349–355). Standard human breast milk LF (Std hLF) and purified recombinant hLF (Rec hLF) were resolved on a 7.5% SDS-Polyacrylamide gel and silver-stained. The results of this analysis are shown in FIG. 2. The recombinant hLF protein migrates at the expected size for processed hLF (lane 2) and is identical as in size to the standard hLF (lane 1). The position of the molecular weight markers are indicated on the left.

B. Western Blot Analysis of Glycosylated and Deglycosylated Recombinant Human Lactoferrin Purified from *Aspergillus awamori* Transformants.

Figure 3:
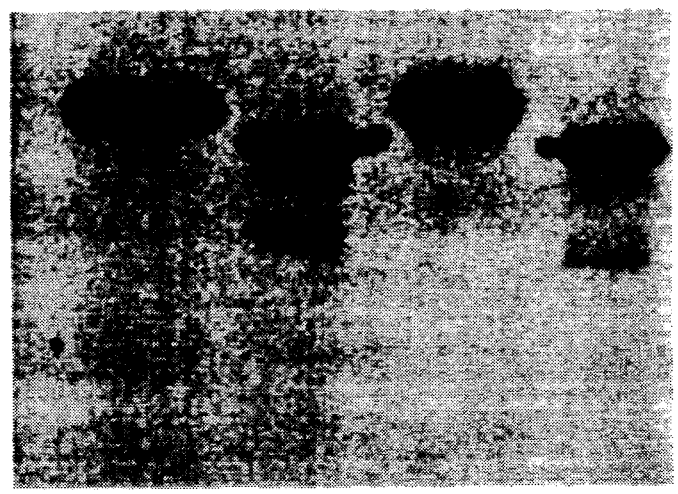
FIG. 3 is a Western blot of glycosylated (1 µg) and deglycosylated recombinant hLF (1 µg) purified from the growth medium of *Aspergillus awamori* transformants containing pPLF-19.

Recombinant human lactoferrin purified from the growth medium of *Aspergillus awamori* transformants, untreated and treated with N-glycosidase F, were resolved by SDS-polyacrylamide electrophoresis, transferred to nitrocellulose and probed using a specific IgG directed against human lactoferrin (Sigma). The results of this analysis are shown in FIG. 3. Comparison of untreated recombinant hLF with untreated standard breast milk hLF illustrate that both of these proteins co-migrate (FIG. 3 lanes 3 and 1, respectively). N-glycosidase F is an enzyme which hydrolyses the glycosylamine linkage generating a carbohydrate free peptide of smaller molecular weight. Comparison of recombinant hLF with standard hLF after treatment with N-glycosidase F illustrates that both proteins migrate identically suggesting that both proteins are similarly N-linked to carbohydrate (FIG. 3, lanes 4 and 2, respectively).

EXAMPLE 3

N-TERMINAL SEQUENCE ANALYSIS CONFIRMS THAT RECOMBINANT HUMAN LACTOFERRIN IS CORRECTLY PROCESSED IN *ASPERGILLUS AWAMORI*

In order to confirm that the recombinant hLF produced in *A. awamori* is correctly processed, the N-terminal portion of the recombinantly produced hLF was sequenced. First, recombinant hLF was expressed in *A. awamori* as a fusion protein to the catalytic domain of the *A. niger* glucoamylase gene (498 AA) which is separated by a synthetic linker which codes for KEX-2 proteolytic cleavage site. Next, the recombinant hLF was purified from the growth medium using CM-sephadex C50 (previously described by Stowell et al., Biochem J, 276; 349–59 (1991)). To determine if recombinant hLF was correctly processed at its N-terminus, the first 10 N-terminal amino acids of the purified protein were sequenced using the automated Edman degradation procedure (5 ug). The results of this analysis are outlined in FIG. 4. The sequence of the recombinant protein is identical to the corresponding amino acids in human breast milk lactoferrin. Hence, recombinant hLF has been correctly processed at the KEX-2 proteolytic cleavage site in *A. awamori*.

EXAMPLE 4

FUNCTIONAL ANALYSIS OF HUMAN LACTOFERRIN PRODUCED IN *ASPERGILLUS AWAMORI*

A. Iron Binding and Saturation of Standard and Recombinant hLF

Figure 5:
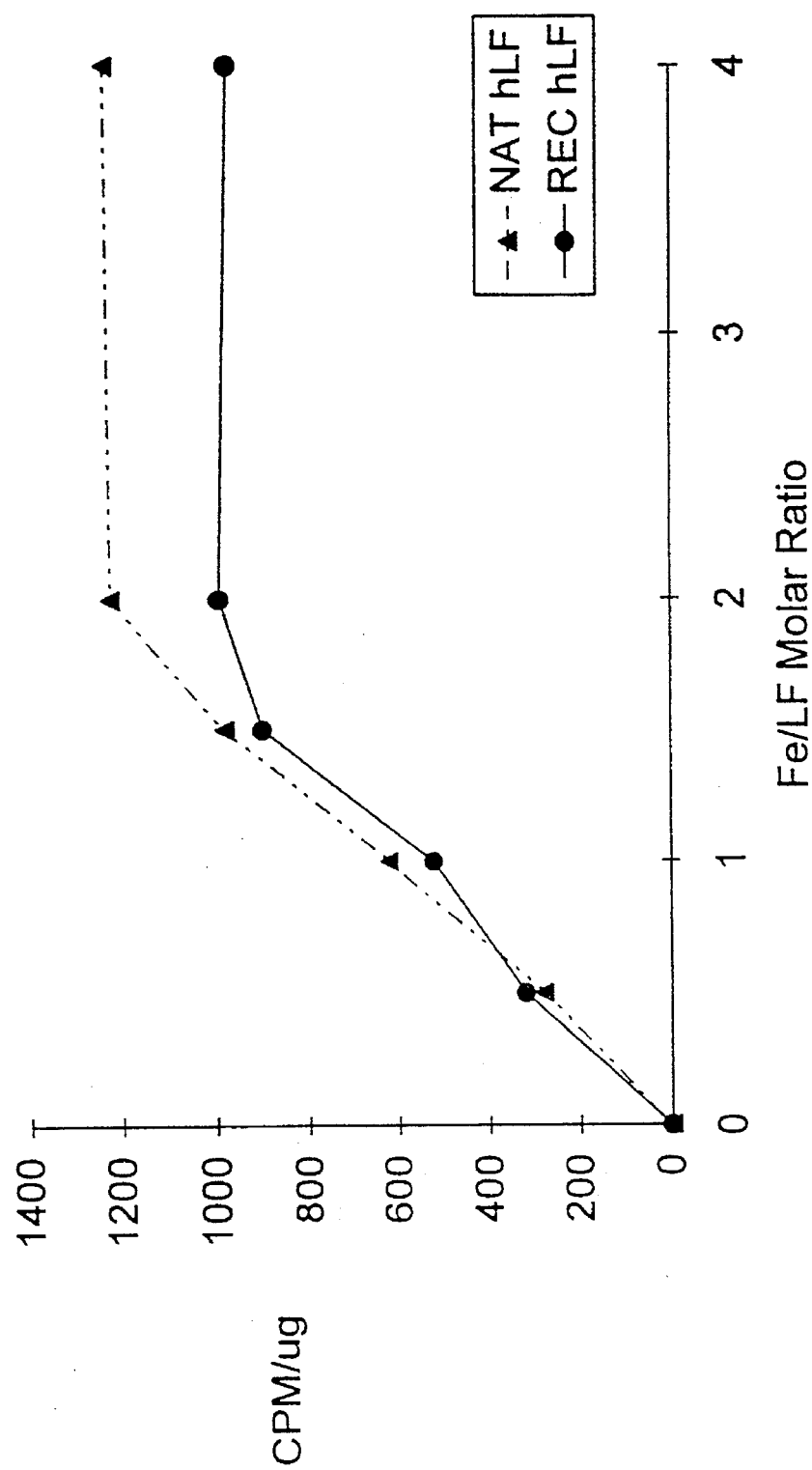
FIG. 5 presents the results of an iron binding and saturation of standard and recombinant hLF study.

Lactoferrin is an iron-building glycoprotein having the capacity to bind two moles of iron per mole of LF. To determine if the binding of iron by recombinant lactoferrin was saturable, an iron-binding assay was performed. To generate apo-lactoferrin, purified Rec hLF and human breast milk were dialyzed against 0.1M citric acid, pH 2.0 followed by extensive dialysis against $H_2O$. The pH of the solution was slowly raised to pH 7.6 using 5 mM sodium phosphate. Increasing concentrations (0.5 to 4.0 molar excess) of $FeCl_3$:$^{59}FeCl_3$:NTA (400:1:8) were added to hLF (500 ug) in 1 ml binding buffer (0.025 M Tris, pH 7.8; 0.01 M Sodium bicarbonate; 0.1 M NaCl). Samples were incubated at room temperature for 30 minutes. Iron-bound hLF was separated from unbound iron and NTA by passage over a NAP-10 column which had been equilibrated with 15 ml of binding buffer. The amount of iron bound to LF was quantified using liquid scintillation counting. The results of this analysis are outlined in FIG. 5. Recombinant and standard hLF bind iron in a similar manner. This binding of iron is dose dependent. Furthermore, binding of iron by both standard and recombinant hLF is saturable at a 2:1 molar ratio of iron to lactoferrin. Typically, saturation levels are reached at 92.5% of maximal binding. This is indicative of initial 7.5% iron still bound to the lactoferrin after dialysis. For the purpose of this invention, "standard hLF" or "natural hLF" is human lactoferrin isolated from human breast milk and purchased from Sigma.

B. pH Stability of Iron-Binding to Standard and Recombinant hLF

Figure 6:
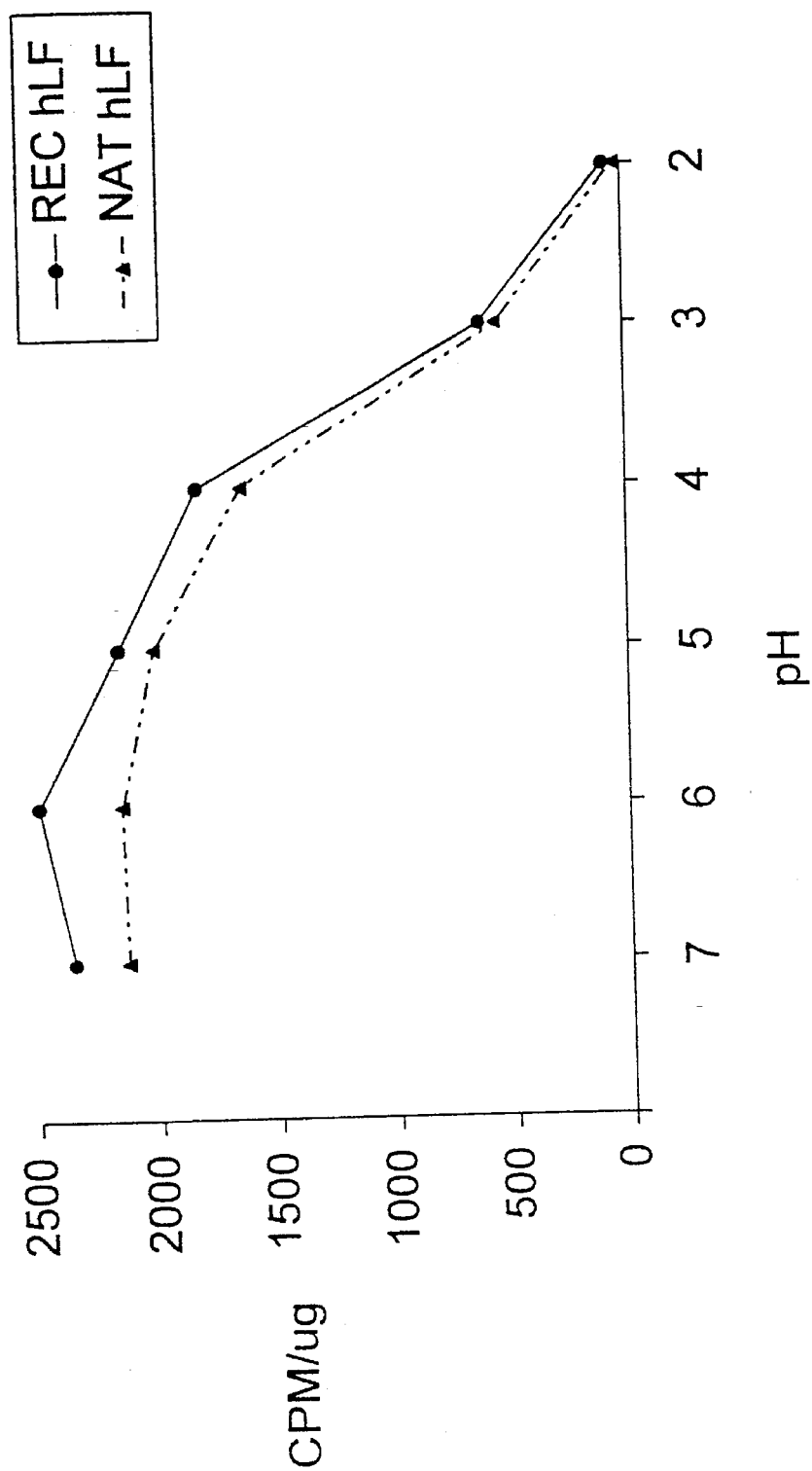
FIG. 6 presents the results from comparing the pH stability of iron-binding to standard and recombinant hLF.

To determine the pH stability of iron-binding to standard and recombinant hLF, $^{59}$Fe-saturated standard and recombinant hLF (500 ug) were dialyzed against buffers ranging from pH 7.0 to pH 2.0 for 48 hours at 4° C. to remove unbound iron (Stowell et al; Biochem J, 276; 349–59 (1991). Iron bound to the hLF samples after dialysis was quantified using liquid scintillation counting. The results of this analysis are shown in FIG. 6. The pH-dependent release of iron from both standard and recombinant hLF is identical. Both standard and recombinant hLF retain most of the iron over a pH range of 7–4 and are essentially iron-free at pH 2.0.

C. Antimicrobial Action of Natural and Recombinant hLF against *E. coli* 0111

Figure 7:
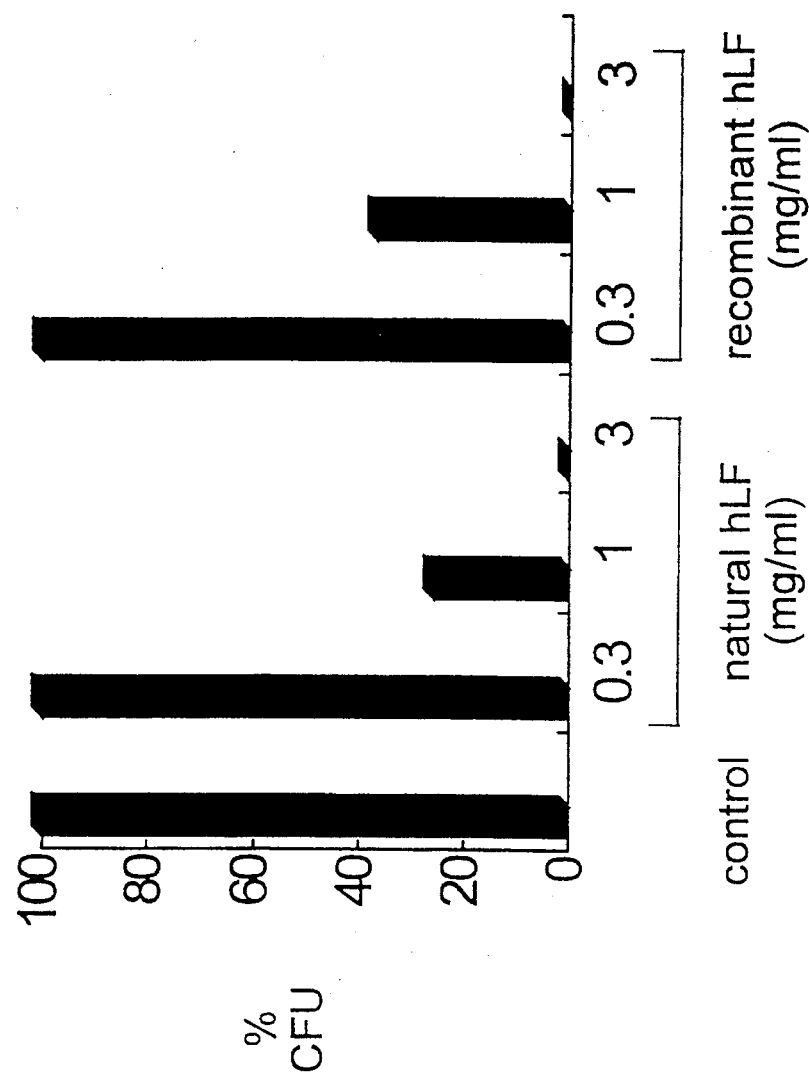
FIG. 7 presents the antimicrobial action of natural and recombinant hLF against *E. coli* 0111.

The antimicrobial activity of both natural (standard) and recombinant hLF against *E. coli* 0111 was determined using an in vitro microtitre plate assay (Nonnecker and Smith., J. Dairy Sci, 67; 606–613 (1984). Briefly, a standard inoculum of logarithmic-phase cells ($1\times10^6$ CFU/ml) were incubated in the presence or absence of increasing concentrations of Apo-Std or Apo-Rec hLF in 1% Basal Bactopeptone medium (100 ul). The samples were cultured at 37° C./200 RPM for 4 hours. Aliquots were removed, serially diluted and plated overnight on MacConkey agar plates for enumeration. The results of this analysis are shown in FIG. 7. Natural and recombinant hLF exert similar dose dependent antimicrobial action against *E. coli* 0111 at all concentrations tested.

D. Antimicrobial Action of Natural and Recombinant hLF Against *Shigella flexneri*.

Figure 8:
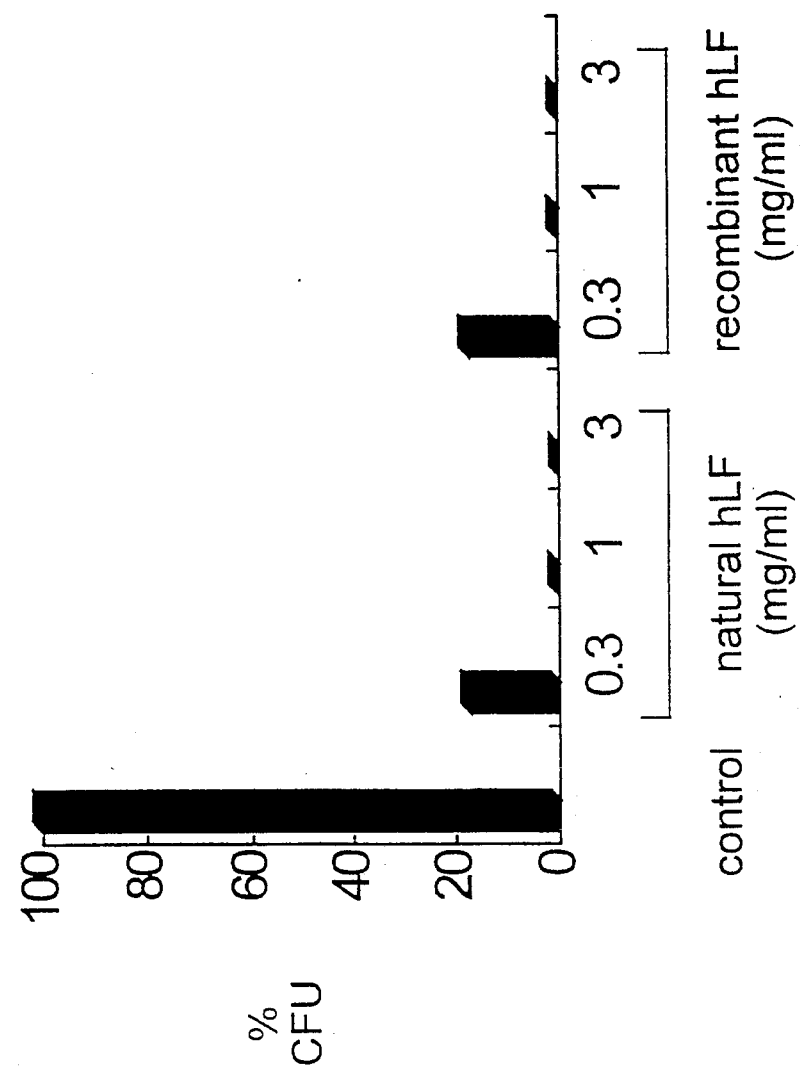
FIG. 8 presents the results obtained from studies on antimicrobial action of natural and recombinant hLF against *Shigella flexneri*.

The antimicrobial action of both natural (standard) and recombinant hLF against *S.flexneri* was determined as described in Example 4(C). The results of this analysis are shown in FIG. 8. Both natural and recombinant hLF exert similar dose dependent inhibition of *S.flexneri* at all concentrations tested.

E. Antimicrobial Action of Natural and Recombinant hLF Against *Shigella flexneri* (Time Kill Study)

Figure 9:
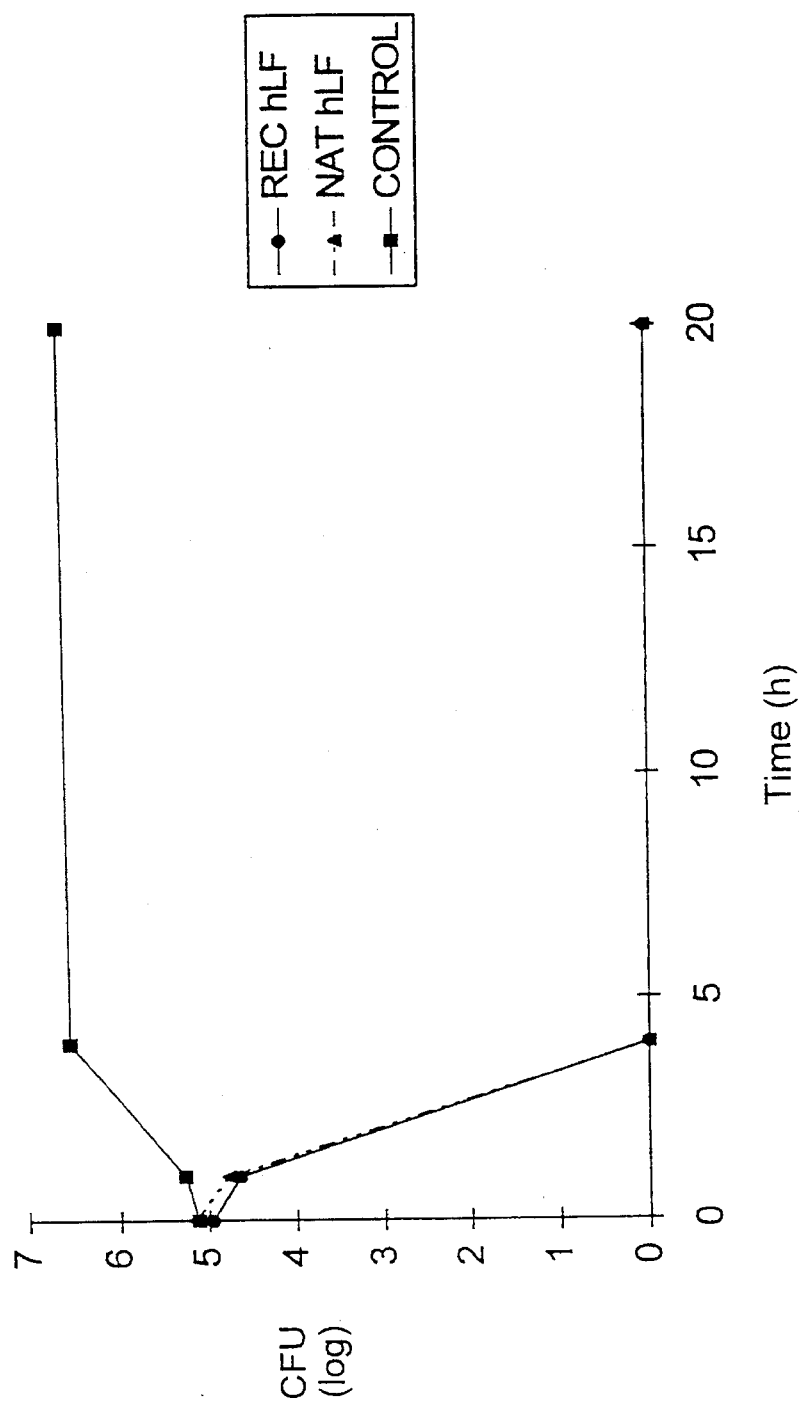
FIG. 9 presents the results of antimicrobial action of natural and recombinant hLF against *Shigella flexneri* in a time kill study.

A time course of the antimicrobial activity of natural and recombinant hLF was carried out. Briefly, a standard inoculum of logarithmic-phase *S.flexneri* cells ($1\times10^6$ CFU/ml) were incubated in the presence or absence of Apo-Std or Apo-Rec hLF (300 ug) in 1% Basal Bactopeptone medium (100 ul). The samples were cultured at 37° C./200 RPM. Aliquots were removed at various time intervals (0, 1, 4 and 20 hours), serially diluted and plated overnight on MacConkey agar plates for enumeration. The results of this analysis are shown in FIG. 9. Recombinant natural and recombinant hLF exert similar antimicrobial action against *S.flexneri* in a time dependent manner with no detectable *S. flexneri* CFUs remaining after 4 hours.

EXAMPLE 5

CONSTRUCTION OF A UNIVERSAL SHUTTLE VECTOR pPLF-26 TO ALLOW IN FRAME SUBCLONING OF ANY cDNA

This Example describes the design and construction of human lactoferrin shuttle vectors capable of expressing mutant forms of hLF in Aspergillus species. Unique NotI and EcoRI sites were created in order to facilitate the cloning of altered forms of lactoferrin into the vector. Protein is expressed under the direction of the glucoamylase promoter and signal sequence as a glucoamylase: hLF chimera, which is process in vivo through the recognition of a KEX-2 cleavage site. Both vectors also contain the glucoamylase 3' untranslated region for enhanced mRNA stability and phleomycin resistance gene for selection in Aspergillus.

I. Human Lactoferrin Expression Vector Constructions

A. Construction of pPLF-26

In order to create an expression vector capable of accepting mutuant forms of lactoferrin, several restriction sites were altered to allow for unique cloning sites. To substitute mutant forms of lactoferrin into the plasmid, the addition of a NOTI site at the 5' end of the hLF gene was designed. An EcoRI site was selected as a unique cloning site at the 3' end of the hLF gene; and, other existing EcoRI sites needed to be eliminated in order to make this site unique.

Figure 10A:
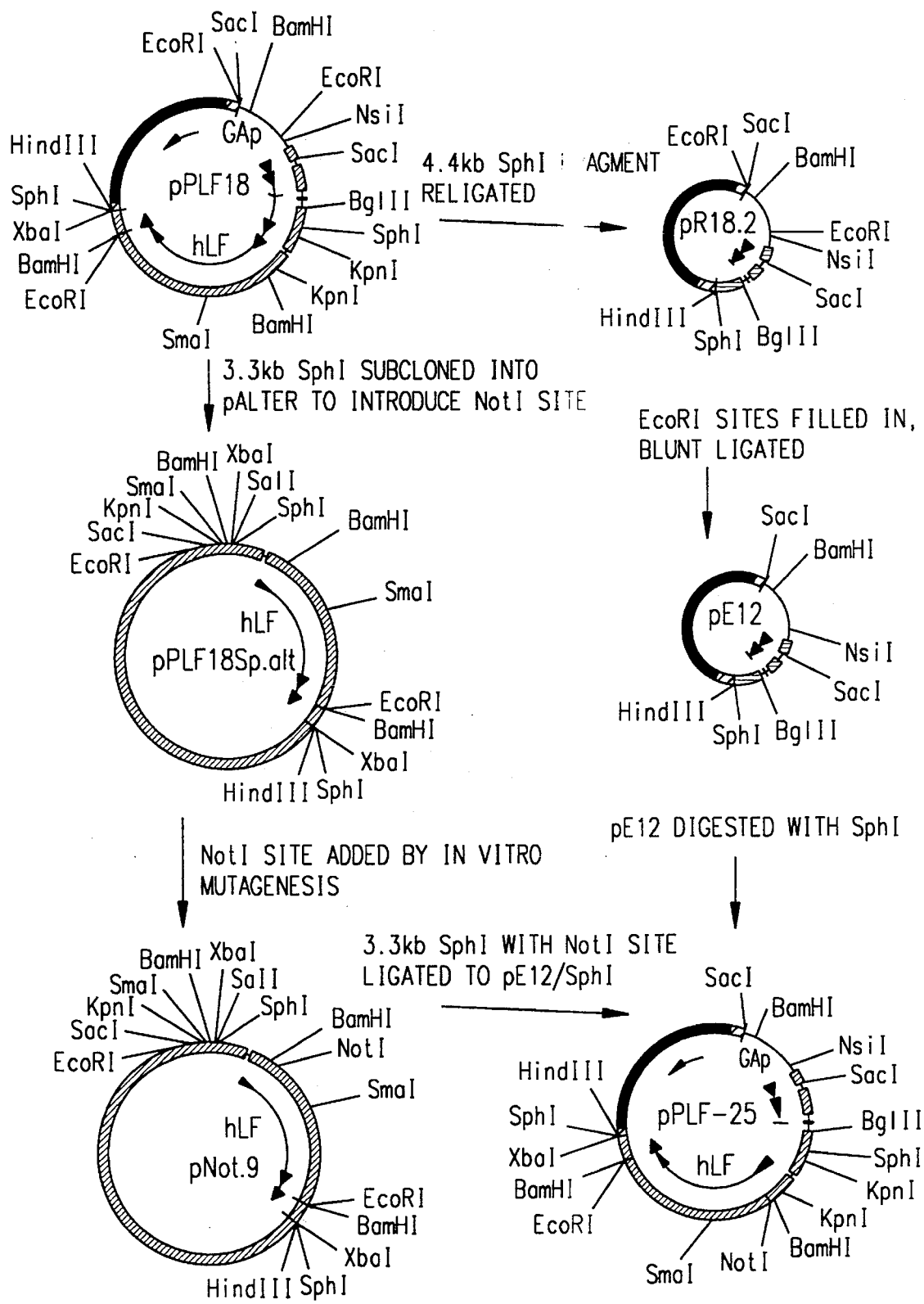
FIG. 10-A and FIG. 10-C outline the design, intermediates, and construction of universal *Aspergillus awamori* expression shuttle vector pPLF-26. Note that not all restriction sites are shown in these figures.

In addition to the unique cloning sites, pPLF-26 contains the *Aspergillus awamori* glucoamylase (GA) promoter, signal sequence, and 498 amino acids of the glucoamylase protein which is separated from hLF by a KEX-2 recognition site. The vector also contains the Aspergillus niger GA 3' untranslated region (UTR), and the phleomycin resistance gene from *Streptoallotetchus hindustanus* (CAYLA vector pUT713) expressed by the *A. niger* beta-tubulin promoter. For selection and replication in *E. coli*, the plasmid contains the ColEI origin of replication and the ampicillin resistance gene. The construction of hLF expression vector pPLF-26 is outlined in FIG. 10-A and FIG. 10-B, and a description of construction intermediates is listed below.

pPLF18Sp.Alt

Plasmid pPLF-18, which contains the promoter, signal sequence and partial protein sequence of glucoamylase separated from hLF by a KEX-2 recognition site, was selected as the starting plasmid for the desired site modifications. pPLF-18 was digested with SphI to isolate two fragments; the 3.3 kb fragment containing hLF was subcloned into the in vitro mutagenesis vector pALTER in the correct orientation to give pPLF18Sp.Alt.

pR18.2

The 4.4 kb Sph fragment from pPLF-18 was relegated to give pR18.2.

pNot.9

NotI restriction site spanning the KEX-2 cleavage site and hLF start site was created by in vitro mutagenesis of the vector pPLF18Sp.Alt. The NotI site, which is the result of a changing a "T" nucleotide to a "C" nucleotide, is in-frame, and does not change any amino acids. The following 21-her oligonucleotide (as shown in SEQ. ID. No. 8) was used for the mutagenesis, where the small case letter denotes a base change:

Oligo HLF NotI:

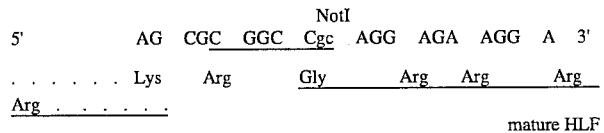

mature HLF

The mutagenic oligo HLF NotI was used in conjunction with the ampicillin repair oligo (Promega) to anneal to single-stranded pPLF18Sp.Alt DNA, which was then filled in using T4 DNA Polymerase and T4 DNA ligase. After transformation of the repair minus strain BMH 71-18 mutS and JM109, 50% of the selected transformants contained in the new NotI site, one of which was designated pNot.9.

pΔE12

Plasmid pR18.2 was digested with EcoRI and the two fragments were isolated by gel electrophoresis. Both fragments were filled in separately with Klenow, and the larger 3.6 kb fragment was dephosphorylated with calf intestinal phosphatase (CIP) at 50° C. for one hour. After phenol extractions and ethanol precipitation, both filled in fragments were blunt ligated to each other. Prior to transformation, the ligation mix was digested with EcoRI to linearize any vector still containing an EcoRI site. Three clones of sixteen had both EcoRI to linearize any vector still containing an EcoRI site. Three clones of sixteen had both EcoRI sites filled in, and were in the correct orientation. One of these was designated pΔE12.

pPLF-25 pΔE12 was digested with SphI and dephosphorylated with CIP. A 3.3 kb SphI fragment containing the new NotI site was isolated from pNot.9 and ligated to pΔE12/Sph. A clone with the correctly oriented SphI fragment was designated pPLF-25, which contained both unique EcoRI and NotI sites, and hLF fused to glucoamylase sequence expressed by the GA promoter.

pLO3ΔRI

In order to make pPLF-25 useful for selection in Aspergillus, a phleomycin resistance cassette was added. The cassette in the plasmid pLO3 contained two EcoRI sites which needed to be eliminated before the cassette could be added. Plasmid pLO3 was digested with EcoRI, both 4.3 and 0.9 kb fragments were isolated, and separately filled in with Klenow. After the fill-in reaction, the 4.3 kb fragment was treated with CIP, then purified and precipitated. Both filled-in fragments were ligated to each other overnight. Selected colonies after bacterial transformation revealed that five of twenty-four had both EcoRI sites filled in and were in the correct orientation, giving pLO3ΔRI.

pPLF-26

A 2.3 kb HindIII fragment from pLO3ΔRI, containing the phleomycin resistance gene transcribed by the B-tubulin promoter, was ligated to pPLF-25 digested with HindIII and dephosphorylated with CIP. Nine out of sixteen clones had the HindIII fragment in both orientations. The plasmid designated "pPLF-26" has the phleomycin resistance gene being transcribed in the same direction as the hLF gene.

Figure 11:
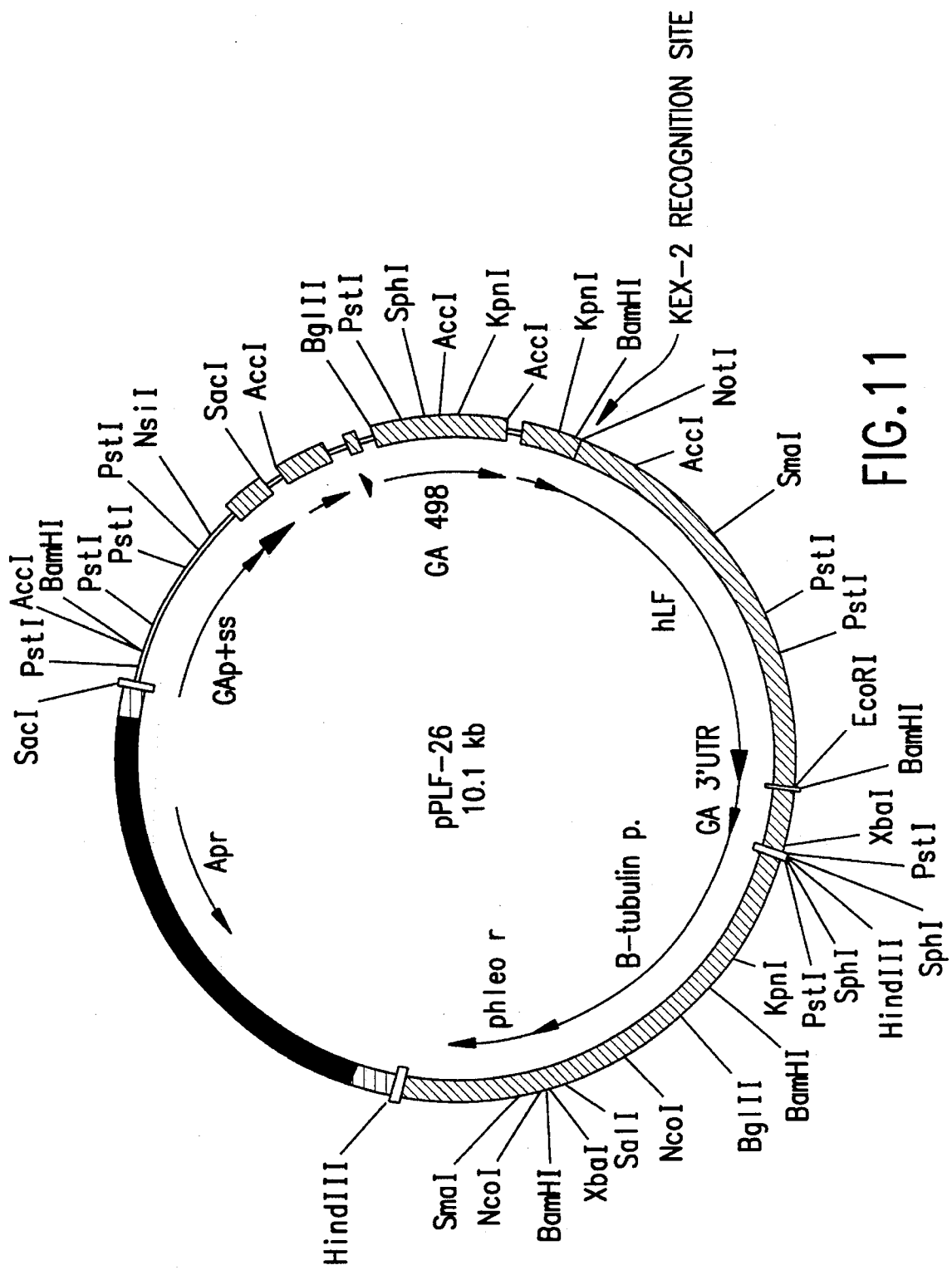
FIG. 11 presents a detailed description of a universal shuttle vector pPLF-26 which contains unique NotI and EcoRI sites for cloning.

FIG. 11 presents a detailed description of a universal shuttle vector pPLF-26 which contains unique NotI and EcoRI sites for cloning. A pre-existing EcoRI site in the glucoamylase (GA) promoter region was removed by fill-in. The vector also contains the GA untranslated region, a Kex-2 cleavage site, and phleomycin resistance for selection in A. awamori. Note that all known restriction sites are shown in this figure.

Figure 12:
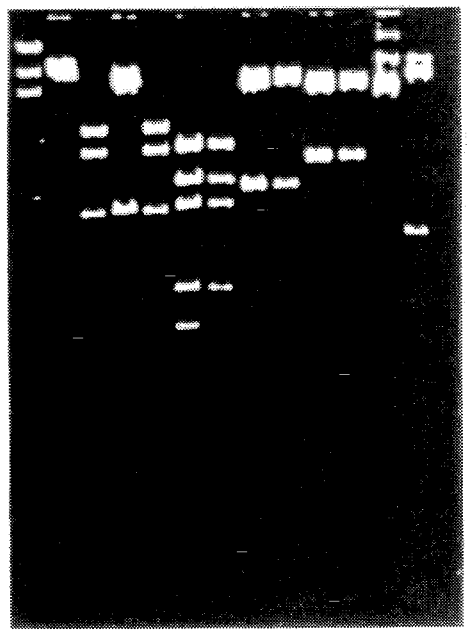
FIG. 12 presents the results from digesting pPLF-26 and pPLF-19 with various restriction enzymes to confirm the presence of the unique NotI and EcoRI sites, and the orientation of the plasmid.

FIG. 12 presents the results from digesting pPLF-26 and pPLF-19 with various restriction enzymes to confirm the presence of the unique NotI and EcoRI sites, and the orientation of the plasmid. One μg of either pPLF-26 or pPLF-19 DNA was digested in a 20 ul volume for one hour at 37° C., with the indicated restriction enzymes. Lane 1. One μg Lambda HindIII standard. Lane 2. pPLF-26 digested with EcoRI. Lane 3. pPLF-19/EcoRI. Lane 4. pPLF-26/EcoRI and NotI. Lane 5. pPLF-19/EcoRI and NotI. Lane 6. pPLF26/BamHI. Lane 7. pPLF-19/BamHI. Lane 8. pPLF-26/HindIII. Lane 9. pPLF-19/HindIII. Lane 10. pPLF-26/SphI. Lane 11. pPLF-19/SphI. Lane 12. pPLF-26/Xba (note: incomplete digest). Lane 13. pPLF-19/Xba.

This universal vector can readily be adapted to express a variety of different desired proteins. For example, the sequences of published hLF's can be inserted into this vector and expressed and isolated therefrom.

EXAMPLE 6

EXPRESSION OF BOVINE AND PORCINE LACTOFERRIN IN *ASPERGILLUS AWAMORI*

The universal A. awamori expression vector constructed in Example 5 can be used to allow in frame subcloning of any cDNA of interest. This vector, pPLF-26, is similar to pPLF-19 utilized for the expression of human lactoferrin in A.awamori. 5' and 3' oligonucleotide primers can be designed to contain Not1 and EcoR1 ends respectively and used to obtain the full length cDNA sequence encoding for mature porcine and bovine lactoferrin using polymerase chain reaction (PCR) amplification of their known DNA sequence. The PCR fragments can be digested with Not1, repaired using Mung Bean Nuclease (Stratagene) and all digested with EcoR1 which will allow in-frame subcloning to the Not1, repaired, EcoR1 digested pPLF-26. The plasmids can then be transformed into *A.awamori* to obtain expression and secretion from these cDNAs as previously described for human lactoferrin.

EXAMPLE 7

EXPRESSION OF HUMAN LACTOFERRIN IN DIFFERENT ASPERGILLUS STRAINS: A COMPARATIVE STUDY

This example compares the different levels of hLF expression in different strains of Aspergillus, specifically in *A. oryzae* and *A. nidulans*, obtained with different vector constructs. These data are to be compared with the data presented above for the expression of hLF in *A. awamori*.

A. Expression of Human Lactoferrin in *Aspergillus oryzae*

Expression plasmid, pAhLFG, was designed to contain the complete cDNA sequence encoding human lactoferrin and to be used for expression of the same in *A. oryzae*. The details of the design, construction, and schematic representation of pAhLFG was presented in co-pending patent application, U.S. Ser. No. 08/250,308, filed May 27, 1994, which is a continuation-in-part of application Ser. No. 07/873,304 filed Apr. 24, 1992, now abandoned. The disclosure of co-pending patent application U.S. Ser. No. 08/250,308 is herein incorporated by reference.

Expression plasmid pAhLFG contains 681 bp of 5'-flanking sequence of the *A. oryzae* AMY II gene that encodes the α-amylase promoter, secretory signal sequence and first codon of mature α-amylase. The cDNA coding for mature human lactoferrin is subcloned in frame downstream from these sequences allowing recombinant protein production by the addition of starch to the growth medium. The *Aspergillus niger* glucoamylase 3' untranslated region provides the transcription terminator and polyadenylation signals. The plasmid also contains the *Neurospora crassa* pyr4 selectable marker and an ampicillin resistance gene.

Southern blot analyses were performed on transformed *Aspergillus oryzae* strains and the data was previously presented in co-pending patent application, U.S. Ser. No. 08/250,308, filed May 27, 1994, which is a continuation-in-part of application Ser. No. 07/873,304 filed Apr. 24, 1992, now abandoned. Briefly, genomic DNA from individual transformants and control AO7 were hybridized with a radiolabelled hLF cDNA probe (2.1 kb). The results demonstrated a radiolabelled fragment (2.8 kb) generated upon EcoR I digestion of the expression plasmid which is present in all the transformants (#1–9) but is absent in control untransformed AO7.

Northern analyses were performed to determine if lactoferrin mRNA was transcribed correctly and efficiently in *A. oryzae* under the regulatory control elements of the expression plasmid. This data was previously presented in co-pending patent application, U.S. Ser. No. 08/250,308, filed May 27, 1994, which is a continuation-in-part of application Ser. No. 07/873,304 filed Apr. 24, 1992, now abandoned. Briefly, the results demonstrated that human lactoferrin mRNA was detected using $^{32}P$ labelled human LF cDNA (2.0 kb) probe. Hybridization with human LF radiolabelled cDNA probe detected a specific radiolabelled band at the correct size for lactoferrin mRNA (2.3kb) in the transformant but not in the control untransformed strain. Quantitation of mRNA levels by dot assay showed comparable levels of expression of endogenous α-amylase mRNA between the control AO7 and the transformant tested (#1).

In order to examine the levels of recombinant LF expressed and secreted from *A. oryzae*, a transformant (#1) was grown in the presence of 3% starch at 30° C. for 72 hours. The growth medium was harvested and the mycelia washed at pH 10 to release any protein loosely associated with the cell wall (Huge-Jensen, et al., *Lipids*, $^{24}$:781–785 (1989)). The results are shown in FIG. 16. Western immunoblot analysis using a specific IgG directed against human lactoferrin detected a 78 kD protein corresponding to the size of lactoferrin in the transformant which was absent in control AO7. (FIG. 16A, lanes 2 and 3).

Figure 16B:
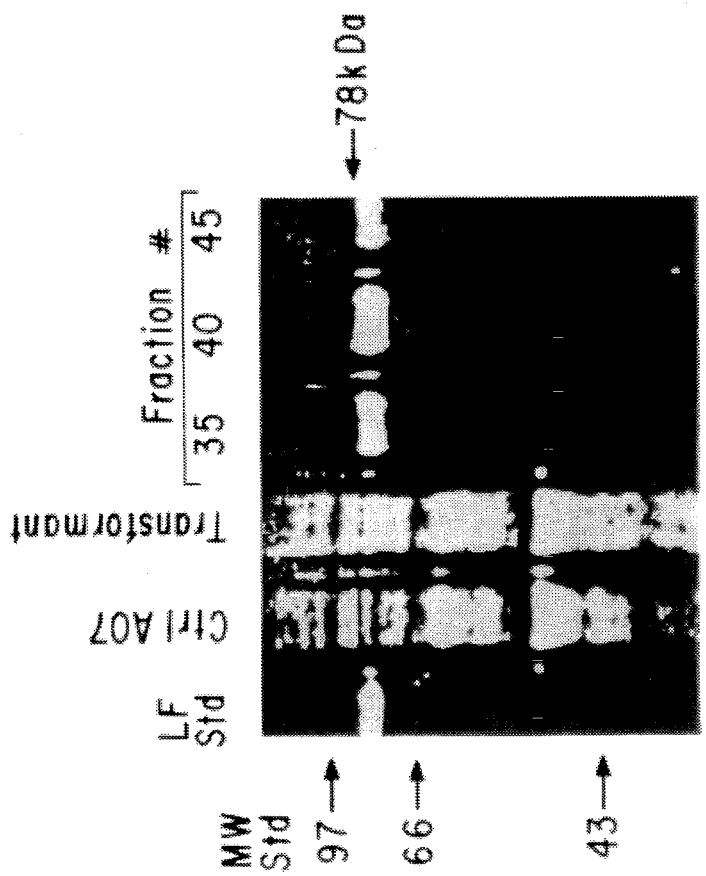
FIG. 16B represents silver-stained SDS-polyacrylamide gel analysis of duplicate samples as in Panel 16A.
Figure 16A:
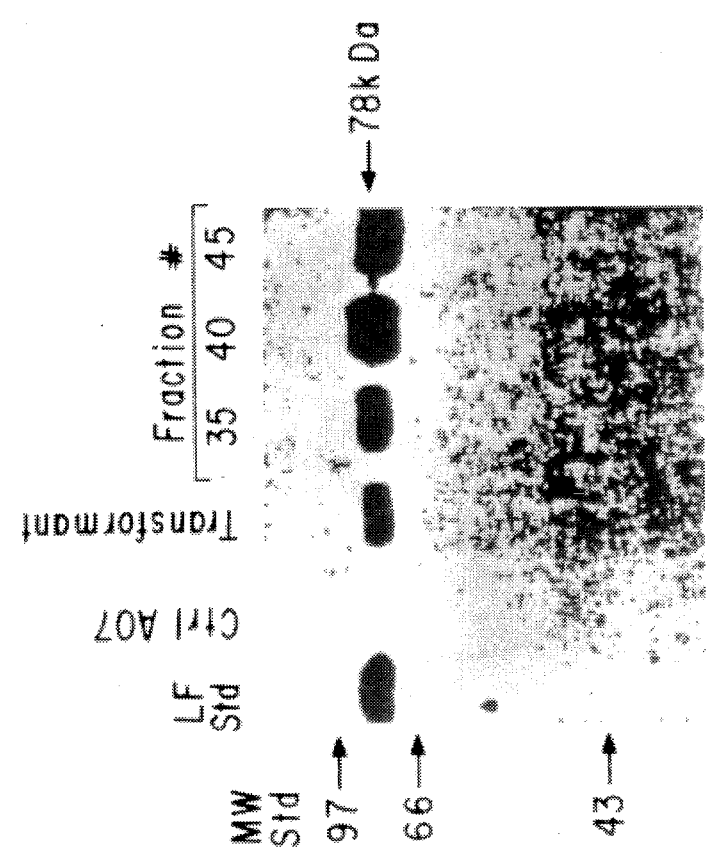
FIG. 16A represents Western immunoblot analysis of recombinant hLF produced in *A. oryzae*.

FIG. 16A: Lane 1 contains breast milk hLF standard (500 ng); Lanes 2 and 3 contain samples of the growth medium (40 ug protein) from induced control AO7 and transformant #1 respectively; Lanes 4–6 contain 25 ul aliquots of eluted fractions (#35, 40, and 45 respectively) collected from the CM-sephadex purification of recombinant hLF from the growth medium.

Analysis of a duplicate silver stained SDS-PAGE gel also showed the presence of a 78 kD protein in the transformant which was absent in A07 control (FIG. 16B, lanes 2 and 3). ELISA analysis using a specific biotinylated IgG directed against hLF (Vilja, et al. *J. Immunol. Methods* 76:73–83 (1985)) indicates that the recombinant hLF is secreted at levels of 5–25 mg/l and represents approximately 5% of the total growth medium protein from induced cultures. There was no correlation between copy number integrated and level of recombinant protein secretion. See Table below for vector design and production levels.

Recombinant lactoferrin was purified from the growth medium of transformant #1 by ion-exchange chromatography using CM-Sephadex C5026 (Stowell, et al. *Biochem. J.* 276:349–355 (1991)). Human lactoferrin was eluted from the column using a linear salt gradient. An immunoreactive band corresponding to the size of hLF was detected in fractions 35–45 by Western immunoblotting using a specific IgG directed against hLF (FIG. 16A, lanes 4–6). Analysis of duplicate samples by silver stain SDS-PAGE showed that this immunoreactive hLF corresponds to the major protein band in these fractions (FIG. 16B, lanes 4–6). These results indicate that this single ion exchange chromatography step led to approximately a 95% purification of the recombinant hLF. FIG. 16B: Silver-stained SDS-polyacryamide gel analysis of duplicate samples as described in FIG. 16A.

To determine if hLF was correctly processed at its N-terminus, the recombinant protein was sequenced from the N-terminus through 10 residues using the automated Edman degradation procedure. The bulk of this material was identical to the corresponding amino acids in native human milk LF (Metz-Boutigue, et al. *Eur J. Biochem.* 145:659–676 (1984)) with the exception of the additional alanine residue at the N-terminus (FIG. 16C) which was introduced into our plasmid construction to exactly mimic the linkage of the signal peptide to mature α-amylase. A small proportion had lost the N-terminal Ala-Gly-Arg tripeptide or the Ala-Gly-Arg-Arg tetrapeptide. Previous analysis of native hLF suggests that this processing pattern may be intrinsic to the hLF protein itself (Hutchens, et al. *Proc. Natl. Acad. Sci. U.S.A.*

88:2994–2998 (1991)) or may be due to heterogeneity in the N-terminal processing capabilities of the *A. oryzae* signal peptidases (Christensen, et al. *Bio/Technology* 6:1419–1422 (1988); Huge-Jensen et al. *Lipids* 24:781–783 (1989)).

A. Expression of Human Lactoferrin in *Aspergillus nidulans*

A plasmid was designed and constructed for the expression of hLF cDNA in *A. nidulans*. The details on this vector design and construction (including all intermediate vectors) were was previously described in co-pending patent application having U.S. Ser. No. 08/145,681, filed Oct. 28, 1993.

Briefly, the *A. nidulans* expression plasmid, pAL3hLFT, contains 300 bp of 5'-flanking sequence of the A. nidulans alcA gene containing all the regulatory elements necessary for controlled gene expression. This vector contains the alcohol dehydrogenase promoter from *A. nidulans*, the natural hLF signal sequence, cDNA encoding hLF, Ben A 3' untranslated sequences from *A. nidulans* and the Neurospora crassa pyr4 selectable marker.

Southern blot analyses were performed on transformed *Aspergillus nidulans* strains and the data was previously described in co-pending patent application having U.S. Ser. No. 08/145,681, filed Oct. 28, 1993, incorporated herein by reference. Briefly, Southern blot analyses were performed to confirm that transformants contained integrated plasmid with hLF cDNA. A hLF-specific radiolabelled band was detected at the expected size (2.3 kb) in lanes 1–10 but not in DNA from control spores. These results demonstrated that hLF cDNA was integrated into the genome of all *A. nidulans* transformants tested and varied randomly from one copy to 20 copies per cell. The site of integration of the plasmid into the *A. nidulans* genome is random due to the absence of homologous sequences to target the vector into a particular site.

The specific details for the production of hLF in *A. nidulans* was previously described in co-pending patent application having U.S. Ser. No.08/145,681, filed Oct. 28, 1993. Briefly, conidia ($1\times10^6$/ml) were cultured in minimal media with Na acetate as carbon source with or without addition of 1.2% ethanol to induce transcription of the hLF cDNA. Media and mycelia were harvested and separated using Miracloth (Calbiochem, San Diego, Calif.). Mycelia (200 mg) were freeze-dried and lyophilized overnight. Total cellular extracts were prepared by homogenization in a glass teflon homogenizer using phosphate-buffered saline in the presence of phenylmethylsulfonylfluoride. The homogenate was centrifuged and the supernatant containing the soluble fraction was recovered. The growth medium was concentrated by freeze drying and lyophilization and resuspended in PBS. Protein concentration was determined using the Bradford reagent according to manufacturer's instructions (BioRad, Richmond, Calif.). Concentrated media samples containing 40 µg protein and soluble extracts (50 µg protein) were subjected to SDS-PAGE. Purified lactoferrin was used as standard (hLF std). The resolved proteins were transferred to nitrocellulose filters electrophoretically using the Western blot procedure. The filters were blocked with Tris-buffered saline containing 2% dried milk and then incubated in the same buffer with the addition of a 1 µg/ml of a specific polyclonal IgG directed against hLF (Sigma, St. Louis, Mo.). The filter were washed in TBS/0.05% Nonidet P-40 followed by incubation with [$^{125}$I] protein A. The filter was then washed, dried and exposed overnight to Kodak XAR5 film at −70° C. The film was then developed by autoradiography. The autoradiographs demonstrate production of hLF.

Western analysis was performed to determine if the hLF cDNA was expressed in the *A. nidulans* transformants under the control of the alcA promoter. Conidia ($1\times10^6$/ml) from one transformant (No. 5), which contained the highest number of copies of integrated hLF cDNAs. The cultures were harvested, washed and reinoculated into minimal medium supplemented with ethanol and grown for an additional 12 or 24 h before harvesting the cultures. Cell extracts and samples of the growth medium were resolved by SDS-PAGE, transferred to nitrocellulose and immunoblotted using a specific polyclonal IgG directed against hLF. An immunoreactive band indistinguishable from native hLF was evident in the cells and growth medium from transformant No. 5 after 12 and 24 h growth only after ethanol induction. These results demonstrate that hLF is expressed in transformed *A. nidulans* under the control of the alcA promoter.

Western analysis revealed hLF in the cells in all of the remaining transformants (data not shown). In general, there was a correlation between the plasmid copy number and the expression levels obtained. In the medium, hLF was detected only with transformants containing multiple copies of integrated expressed plasmids (Nos. 1, 5, 7 and 10).

The pilot fermentation of transformant No. 5 was carried to determine the approximate amount of hLF produced ELISA analysis, using a specific biotinylated IgG directed against hLF, demonstrated that the total level of recombinant hLF produced was 5 mg/l with approx. 30% (1.5–2.0 µg/ml) of this material secreted into the medium.

See Table below for vector design and productions levels.

Thus, this Example demonstrates that the Applicants have improved and enhanced the expression of human lactoferrin by modifying the design of the expression vector plasmid constructs and by changing the host cells used. As noted in the table below, several different vector constructs have been used to produce human lactoferrin in at least four different Aspergillus strains. The amount of human lactoferrin produced is shown in milligrams hLF per liter.

For convenience, each vector component is listed in the order that it appears in the vector construct directionally positioned from left to right. The components included in the expression plasmid vector include: a promoter and the source of the promoter, a signal sequence and the source of the signal sequence, a linker sequence, DNA encoding for human lactoferrin, a transcription termination sequence, and a selectable marker.

TABLE 1

Human Lactoferrin Production Levels in Different Aspergillus Strains Using Different Vectors

| Vector | Host Cells | Promoter (Source) | Signal Sequence (Source) | Linker Sequence | cDNA | Transcription Termination Sequence | Selectable Marker | mg/liter HuLF Produced |
|---|---|---|---|---|---|---|---|---|
| A(92) | A. oryzae | ∝ - amylase (A. oryzae) | ∝ - amylase (A. oryzae) | — | hLF | 3' untranslated from glucoamylase (A. niger) | pyr4 (Neurospora crassa) | 5–25 |
| B(1093) | A. nidulans | alcohol dehydrogenase (alc - A) (A. nidulans) | natural huLF signal sequence | — | hLF | 3' untranslated from Ben A (A. nidulans) | pyr4 (Neurospora crassa) | 5 |
| C(0594) | A. awamori | glucoamylase (A. awamori) | glucoamylase (A. awamori) plus 5' 1/2 end of glucoamylase gene (A. awamori) | Synthetic Linker which codes for Kex2 peptidase cleavage site | hLF | 3' untranslated from glucoamylase (A. niger) | phleomycin | 500 |
| D(0894) | A. awamori | glucoamylase (A. awamori) | glucoamylase (A. awamori) plus 5' 1/2 end of glucoamylase gene (A. awamori) | Synthetic Linker which codes for Kex2 peptidase cleavage site | hLF | 3' untranslated from glucoamylase (A. niger) | phleomycin | 900 |

EXAMPLE 8

PRODUCTION OF LACTOFERRIN USING PUBLISHED DNA SEQUENCES WHICH CONTAIN ALLELIC VARIATIONS

One may employ any one of several known DNA sequences encoding for lactoferrins as identified in the published literature and patent applications referenced above, incorporated herein by reference. Additionally, one may employ DNA sequences encoding polypeptide fragments of lactoferrin which maintain characteristics of lactoferrin. One of ordinary skill in this art will understand and know that the scope of this invention also includes the production of the different published and obvious therefrom allelic variants of human, porcine or bovine lactoferrin. Some allelic variations have been reported in the literature and they are intended to be included as the types of lactoferrins that may be produced by the process of the subject invention.

EXAMPLE 9

FERMENTATION PROTOCOLS

Different growth and production conditions can be used for the expression of recombinant human lactoferrin in *Aspergillus awamori*. The following descriptions are presented for the purposes of illustrating various conditions which can be used for the expression of hLF in *Aspergillus awamori* and are not meant to be limitations of the present invention in any form. Presented below is a general outline of the fermentation production process and the process used to recover the produced lactoferrin. One of ordinary skill in this art understands that the protocol may be changed or modified in minor ways in order to enhance the production of the desired lactoferrin or lactoferrin polypeptide.

The following is a brief outline for producing lactoferrin by using a fermentation process.

I. FERMENTATION PROCESS

A. MEDIUM COMPONENTS

1) Seed medium

| | |
|---|---|
| Roquette Corn Steep Powder | 100 g/L |
| Glucose | 10 g/L |
| $MgSO_4$—$7H_2O$ | 1 g/L |
| $NaH_2PO_4$—$2H_2O$ | 1 g/L | pH to 5.8 before autoclaving and autoclave for 15 minutes.

2) Production medium (concentrations are post-inoculation)

| | |
|---|---|
| Amaizo Lodex-5 partially hydrolyzed corn starch | 175 g/L |
| Roquette Corn Steep Powder (Solulys ® A ST) | 60 g/L |
| Trisodium Citrate | 80 g/L |
| $MgSO_4$—$7H_2O$ | 2 g/L |
| $NaH_2PO_4$—$2H_2O$ | 1.3 g/L |
| Ammonium sulfate | 15 g/L |
| Antifoam 204 | 2 ml/L | pH to 6.2 before autoclaving and autoclave for 15 minutes.

The inventors have found that enhanced lactoferrin production can be achieved when partially hydrolyzed starches are used in the fermentation process. However, combinations of unmodified corn starch and dextrose have yielded reasonable production of lactoferrin. One may employ less amounts of starch products or substitute more expensive starch products to optimize production of the lactoferrin by routine experimentation.

B. FERMENTATION PROCESS

To date, the fermentation is run as a batch process. Maximum product concentration is reached at 5–6 days.
1) Seed stage 1:
 a) 450 mls of seed medium in a 2L Erlenmeyer flask
 b) Inoculate with $1\times10^6$ spores per ml of seed medium.
 c) Incubate for 24 hours at 33° C., 70% relative humidity at 240 rpm (50 mm throw shaker).

2) Seed stage 2:
   a) 20L seed medium in a NBS Micros 30 fermenter with two 12 cm six-blade rushton impellers.
   b) 30 minute sterilization.
   Inoculate with 2% of stage 1 seed.

| | |
|---|---|
| Agitation | 500 rpm |
| Airflow | 0.75 VVM |
| Pressure | 300 mbar |
| pH | not controlled |
| DO | not controlled |

3) Production:

The pilot vessel is a B. Braun Biotech UD100 with a 3:1 aspect ratio. Two 16 cm six-blade Rushton impellers are used for agitation. The fermentation is run at 80L post-inoculation.

| | | |
|---|---|---|
| Agitation | 450 rpm | Power input has not yet been examined. |
| Temperature | 33° C. | |
| Aeration | 0.75 VVM | This variable has not yet been examined. |
| Pressure | 300 mbar | |
| pH | not controlled | |
| DO | not controlled | This variable has not yet been examined. |
| Antifoam | not required | |

Vessel conditions are as described above. Vessel is charged with 80L of Medium Components and brought to a volume of 72L with deionized water. It is sterilized for 30 minutes. Eight liters (10%CV) of Stage 2 seed is transferred at 36–48 hours growth. Optimized seed processes are currently being developed.

Lactoferrin production is seen by 24 hours with maximum product accumulation at 5–6 days.

II. DOWNSTREAM PROCESSING

A. FILTRATION

The fermentation reaches a 30–40 % packed cell volume with a non-pelleted morphology. If filtration is used to clarify the broth, a filter aid is required. Because of the low process volumes, straight vacuum filtration over a 3,000 cm$^2$ support may be used. A polypropylene filter mat is used as a base.

Initial tests used diatomaceous earth as the filter aid. However, straight-calcined or flux-calcined diatomaceous earth cannot be used as a filter aid as they bind lactoferrin. Only acid-washed diatomaceous earth will not bind lactoferrin. Acid-washed diatomaceous earth (DE) can be purchased at 40–50 times the cost of the untreated product. Another option is to acid wash the DE at the production site. Preliminary tests determined that it can be slurried with 3N HCl, mixed for 45 minutes and then washed with deionized water until the wash water is pH 4.0. Lactoferrin did not bind to this treated material. The treated DE was used at a 1:5 W/V ratio with whole broth. The DE was slurried with deionized water prior to mixing with the broth. It was found that a 1:10 ratio did not allow filtration.

An alternative product is cellulose fiber. The inventors have found that Solkafloc 10IND (Protein Technologies International in Urbana, Ill.; 1-800-258-0351) works well with no binding of lactoferrin. The inventors use Solkafloc as a filler to aid filtration. For 100L of fermentation broth, 20 kg of Solkafloc is slurried with 100L of deionized water. The broth is mixed into the slurry. The mixture is then filtered easily. The clarity achieved at this step enables further downstream processing (ultrafiltration and column chromatography) to proceed without additional filtration requirements. The ratio of Solkafloc to broth and deionized water for a single batch filtration is in the process of being optimized. Recovery of lactoferrin should almost be quantitative if the filter cake is washed. With continuous filtration process equipment, the methods for using Solkafloc as a filter aid will change.

One may use existing strains or develop strains with improved rheology and filtration characteristics. For example, mutants that pellet in stirred tank fermentation will allow thicker filter cakes during processing and will not require filter aid except as a filter precoat.

B. ULTRAFILTRATION

The clarified broth is concentrated using ultrafiltration. Two Amicon S10Y30 (0.93 m$^2$ each) spiral cartridges with 30,000 MW membranes are used with an Amicon DC-30 system. The membranes are a low protein-binding cellulose-based material. Flux rates are 1–1.8 rpm depending on the stage of the process. Once a minimum operational process volume has been reached, the concentrated solution is continuously dialyzed with five volumes of a buffer containing 0.1M NaCl, 1 mM EDTA, and 25 mM TRIS pH 7.5. The buffer is then cooled to 4° C. and the dialyzed solution is concentrated to the minimum volume possible and recovered. Yields have been near 100% with this process.

The final ultrafiltration (UF) concentrate is 5–8 mg/ml total protein with lactoferrin at 10% of total protein. The recovery rate will be optimized as new strains are developed. For an 80L fermentation batch, concentration and dialysis with this system takes approximately 2 hours.

C. CHROMATOGRAPHIC SEPARATION

Pharmacia CM Sepharose Fast Flow gel is used. The binding capacity of this resin for lactoferrin in clarified broth is approximately 20 mg/ml.

UF concentrate is applied to the column. The loaded column is washed first with 0.1 M NaCl/25mM TRIS pH 7.5, and then with a 0.2M NaCl 25mM TRIS pH 7.5. No lactoferrin will be released unless the column is overloaded. The lactoferrin is eluted with 0.5M NaCl/25mM TRIS pH 7.5. The volume of the elution fractions containing lactoferrin is usually twice the volume of the resin bed.

D. CONVERSION TO APOLACTOFERRIN

The 0.5M NaCl fractions containing lactoferrin are combined. 1M ammonium citrate is added to bring the final concentration to 0.1M ammonium citrate. The pH is slowly adjusted to 2.0 with 10 N HCl. The solution is transferred to an appropriately sized ultrafiltration unit using 30,000 MW membranes where it is concentrated to an appropriate volume and then continuously dialyzed with five volumes of 0.5M NaCl/0.1M Ammonium citrate pH 2.0. After release and dialysis of iron is completed, the pH is adjusted to neutral to prevent precipitation in the next process. If there is residual iron present, it will rebind to the lactoferrin at the neutral pH. The dialysis buffer is changed to 50 mM ammonium bicarbonate (pH 7.8) and the solution is continuously dialyzed with five volumes of buffer. The solution is then concentrated to a minimum volume, recovered, and lyophilized.

The procedure is currently being optimized. Specific factors are considered on a case by case basis depending on the strain used. Some of the factors include (1) pH limits, (2) pre-treatment of equipment to eliminate iron, and (3) pre-treatment of buffers with Chelex resins to remove trace amounts of iron. It may be necessary to go through an intermediate buffer such as 0.2M NaCl 50 mM Ammonium bicarbonate to avoid precipitation of lactoferrin and rebinding of residual iron.

EXAMPLE 10

PRODUCTION OF LACTOFERRIN OR LACTOFERRIN POLYPEPTIDE FRAGMENTS AS A FUSION PRODUCT IN *ASPERGILLUS ORYZAE* OR *ASPERGILLUS NIGER* CELLS

A. Expression of Lactoferrin or Lactoferrin Polypeptide Fragments in *Aspergillus Oryzae*

A similar expression vector as that which has been previously described can be constructed to allow for the expression of lactoferrin or lactoferrin polypeptide fragments as a fusion protein product in *Aspergillus oryzae*. The *A. oryzae* expression vector would contain the following components operably linked from 5' to 3':

(a) a promoter from *Aspergillus oryzae* α-amylase gene;

(b) signal sequence from the *A. oryzae* α-amylase gene;

(c) 5' portion of the *A. oryzae* α-amylase gene;

(d) linker sequence encoding Kex2 peptidase cleavage site whereby there is an endogenous proteolytic enzyme specific for said linker sequence;

(e) transcription termination sequence from the *A. niger* glucoamylase gene; and (f) phleomycin resistance selectable marker gene;

wherein said vector is capable of producing lactoferrin or a lactoferrin polypeptide fragment as a fusion protein and expressing the same as a processed protein.

The vector would then be used to transform *A. oryzae* cells; the product of this novel plasmid vector construct is a fusion protein comprised of half of the highly expressed *A. oryzae* α-amylase gene fused to the lactoferrin or lactoferrin polypeptide fragment corresponding to the nucleotide sequence of step (e) above. The lactoferrin or lactoferrin polypeptide fragment fusion product would then be processed by an endogenous *A. oryzae* proteolytic enzyme which is specific for the Kex2 peptidase site.

B. Expression of Lactoferrin or Lactoferrin Polypeptide Fragments in *Aspergillus Niger*

A similar expression vector as that which has been previously described can be constructed to allow for the expression of lactoferrin or lactoferrin polypeptide fragments as a fusion protein product in *Aspergillus niger*. The *A. niger* expression vector would contain the following components operably linked from 5' to 3':

(a) promoter from Aspergillus niger glucoamylase gene;

(b) signal sequence from the *A. niger* glucoamylase gene;

(c) 5' portion of the *A. niger* glucoamylase gene;

(d) linker sequence encoding Kex2 peptidase cleavage site whereby there is an endogenous proteolytic enzyme specific for said linker sequence;

(e) transcription termination sequence from the *A. niger* glucoamylase gene; and (f) phleomycin resistance selectable marker gene;

wherein said vector is capable of producing lactoferrin or a lactoferrin polypeptide fragment as a fusion protein and expressing the same as a processed protein.

The vector would then be used to transform *A. niger* cells; the product of this novel plasmid vector construct is a fusion protein comprised of half of the highly expressed *A. niger* glycoamylase gene fused to the lactoferrin or lactoferrin polypeptide fragment corresponding to the nucleotide sequence of step (e) above. The lactoferrin or lactoferrin polypeptide fragment fusion product would then be processed by an endogenous *A. niger* proteolytic enzyme which is specific for the Kex2 peptidase site.

In conclusion, it is seen that the present invention and the embodiments disclosed herein are well adapted to carry out the objectives and obtain the end set forth in this application. Certain changes can be made in the method and apparatus without parting from the spirit and scopes of this invention. It is realized that changes are possible and that it is further intended that each element or step presided in any of the filing claims is to be understood as to referring to all equivalent elements or steps for accomplishing the essentially the same results in substantially the same or equivalent manner. It is intended to cover the invention broadly in whatever form its principles may be utilized. The present invention, therefore, is well adapted to carry out the objects and obtain the ends and advantages mentioned, as well as others inherent therein.

---

---

We claim:

1. A plasmid DNA sequence comprising nucleotide sequence elements operably linked in the following 5' to 3' order:

(a) a fungal promoter sequence;

(b) a sequence encoding a signal peptide;

(c) a sequence encoding an amino terminal portion of a highly expressed endogenous gene the product of which is secreted by Aspergillus cells; and, (d) a sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin.

2. The plasmid DNA sequence of claim 1, wherein the promoter is selected from genes of the group consisting of an alcohol dehydrogenase gene, an α-amylase gene, a glucoamylase gene, and a benA gene.

3. The plasmid DNA sequence of claim 2, wherein said promoter is a glucoamylase gene promoter.

4. The plasmid DNA sequence of claim 3, wherein the glucoamylase gene is endogenous to A. awamori or A. niger.

5. The plasmid DNA sequence of claim 2, wherein the promoter is an α-amylase gene promoter.

6. The plasmid DNA sequence of claim 5, wherein the α-amylase gene is endogenous to A. oryzae.

7. The plasmid DNA sequence of claim 1, wherein the signal peptide-encoding sequence is selected from the genes of the group consisting of a glucoamylase gene and an α-amylase gene.

8. The plasmid DNA sequence of claim 7, wherein the signal peptide-encoding sequence is an A. awamori glucoamylase gene or an A. niger glucoamylase gene.

9. The plasmid DNA sequence of claim 7, wherein the signal peptide-encoding sequence is selected from an A. oryzae α-amylase gene.

10. The plasmid DNA sequence of claim 1, wherein the sequence encoding an amino terminal portion of an endogenous, secreted, Aspergillus polypeptide is selected from the group of Aspergillus genes consisting of an α-amylase gene and a glucoamylase gene.

11. The plasmid DNA sequence of claim 10, wherein the endogenous Aspergillus gene is an A. oryzae α-amylase gene.

12. The plasmid DNA sequence of claim 10, wherein the endogenous Aspergillus gene is an A. awamori glucoamylase gene or an A. niger glucoamylase gene.

13. The plasmid DNA sequence of claim 1, wherein the native lactoferrin is selected from the group consisting of a human lactoferrin, a bovine lactoferrin and a porcine lactoferrin.

14. The plasmid DNA sequence of claim 1, further comprising a transcription termination sequence and a selectable marker gene.

15. The plasmid DNA sequence of claim 14, wherein the transcription termination sequence is selected from a gene of the group consisting of an α-amylase gene, a glucoamylase gene, an alcohol dehydrogenase gene and a benA gene.

16. The plasmid DNA sequence of claim 15, wherein the transcription termination sequence is from an *A. niger* glucoamylase gene.

17. The plasmid DNA sequence of claim 14, wherein the selectable marker gene is selected from the genes of the group consisting of a pyr4 gene, a pyrG gene, an amdS gene, an argB gene, a trpC gene, and a phleomycin resistance gene.

18. The plasmid DNA sequence of claim 17, wherein the selectable marker is the phleomycin resistance gene.

19. The plasmid DNA sequence of claim 1, further comprising a sequence encoding a peptide linker joining an amino terminal portion of said encoded endogenous Aspergillus polypeptide to the amino terminus of an encoded native lactoferrin polypeptide, iron-binding lobe of a native lactoferrin, or an antimicrobial peptide of a native lactoferrin, the peptide linker comprising a fungal peptidase cleavage site.

20. The plasmid DNA sequence of claim 19, wherein the linker peptide encoding sequence comprises codons encoding the Kex2 peptidase cleavage site.

21. The plasmid DNA sequence of claim 19, wherein the promoter is selected from genes of the group consisting of an alcohol dehydrogenase gene, an α-amylase gene, a glucoamylase gene, and a benA gene.

22. The plasmid DNA sequence of claim 21, wherein the promoter is a glucoamylase gene promoter.

23. The plasmid DNA sequence of claim 22, wherein the glucoamylase gene is an *A. awamori* glucoamylase gene or an *A. niger* glucoamylase gene.

24. The plasmid DNA sequence of claim 21, wherein the promoter is an α-amylase gene promoter.

25. The plasmid DNA sequence of claim 24, wherein the α-amylase gene is an *A. oryzae* α-amylase gene.

26. The plasmid DNA sequence of claim 19, wherein the signal peptide-encoding sequence is selected from the genes of the group consisting of a glucoamylase gene and an α-amylase gene.

27. The plasmid DNA sequence of claim 26, wherein the signal peptide encoding sequence is selected from an *A. awamori* glucoamylase gene or an *A. niger* glucoamylase gene.

28. The plasmid DNA sequence of claim 26, wherein the signal peptide-encoding sequence is selected from an *A. oryzae* α-amylase gene.

29. A plasmid DNA sequence comprising the following components operably linked from 5' to 3':

(a) a promoter from *A. niger* glucoamylase gene;

(b) a signal peptide-encoding sequence from the *A. niger* glucoamylase gene;

(c) a sequence encoding an amino terminal portion of the *A. niger* glucoamylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene.

30. A plasmid DNA sequence comprising the following components operably linked from 5' to 3':

(a) a promoter from *A. oryzae* α-amylase gene;

(b) a signal peptide-encoding sequence from the *A. oryzae* α-amylase gene;

(c) a sequence encoding an amino terminal portion of the *A. oryzae* α-amylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene.

31. A plasmid DNA sequence comprising the following components operably linked from 5' to 3':

(a) a promoter from *A. awamori* glucoamylase gene;

(b) a signal peptide-encoding sequence from the *A. awamori* glucoamylase gene;

(c) a sequence encoding an amino terminal portion of the *A. awamori* glucoamylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene.

32. The plasmid DNA sequence of claim 31, further defined as having ATCC Accession Number 74290 and designated Awa LF 24-1.

33. *Aspergillus awamori* fungal cells comprising the plasmid of claim 31.

34. A plasmid DNA sequence comprising nucleotide sequence elements operably linked in the following 5' to 3' order:

(a) a first DNA sequence as a means for encoding a fungal promoter sequence;

(b) a second DNA sequence as a means for encoding a signal peptide;

(c) a third DNA sequence as a means for encoding an amino terminal portion of a highly expressed endogenous gene the product of which is secreted by Aspergillus cells; and, (d) a fourth DNA sequence as a means for encoding a peptide selected from the group consisting of a mature, native, lactoferrin, an iron-binding lobe of a native lactoferrin, and an antimicrobial peptide of a native lactoferrin.

35. The plasmid DNA sequence of claim 34, further comprising a fifth DNA sequence as a means for encoding a peptide linker joining an amino terminal portion of said encoded endogenous Aspergillus polypeptide to the amino terminus of an encoded native lactoferrin polypeptide, iron-binding lobe of a native lactoferrin, or an antimicrobial peptide of a native lactoferrin, the peptide linker comprising a fungal peptidase cleavage site.

36. A process for producing lactoferrin which comprises culturing a transformed Aspergillus fungal cell containing a recombinant plasmid, wherein said plasmid comprises the following components operably linked from 5' to 3':

(a) a promoter;

(b) a signal sequence;

(c) a sequence encoding an amino terminal portion of a highly expressed endogenous gene the product of which is secreted by Aspergillus cells; and, (d) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

wherein said transformed Aspergillus fungal cells are cultured in a suitable nutrient medium until the mature, native, lactoferrin, the iron-binding lobe of a native lactoferrin, or the antimicrobial peptide of a native lactoferrin, is produced as a fusion product and then processed via an endogenous proteolytic enzyme specific for the linker sequence, wherein the processed mature, native, lactoferrin, the iron-binding lobe of a native lactoferrin, or the antimicrobial peptide of a native lactoferrin is secreted into the nutrient medium and isolated therefrom.

37. The process of claim 36, wherein the plasmid further comprises a sequence encoding a peptide linker joining an amino terminal portion of said encoded endogenous Aspergillus polypeptide to the amino terminus of an encoded native lactoferrin polypeptide, iron-binding lobe of a native lactoferrin, or an antimicrobial peptide of a native lactoferrin, the peptide linker comprising a fungal peptidase cleavage site.

38. The process of claim 37, wherein the peptide linker encoding sequence comprises codons encoding the Kex2 peptidase cleavage site.

39. The process of claim 37, wherein the promoter is selected from genes of the group consisting of an alcohol dehydrogenase gene, an α-amylase gene, a glucoamylase gene, and a benA gene.

40. The process of claim 39, wherein the promoter is the glucoamylase gene promoter.

41. The process of claim 40, wherein the glucoamylase gene is an *A. awamori* glucoamylase gene or an *A. niger* glucoamylase gene.

42. The process of claim 39, wherein said promoter is an α-amylase gene promoter.

43. The process of claim 42, wherein the α-amylase gene is an *A. oryzae* α-amylase gene.

44. The process of claim 37, wherein the signal peptide-encoding sequence is selected from the genes of the group consisting of a glucoamylase gene and an α-amylase gene.

45. The process of claim 44, wherein the signal peptide-encoding sequence is selected from an *A. awamori* glucoamylase gene.

46. The process of claim 44, wherein the signal peptide-encoding sequence is selected from an *A. oryzae* α-amylase gene.

47. The process of claim 37, wherein the sequence encoding an amino terminal portion of a highly expressed endogenous gene the product of which is secreted from Aspergillus cells is selected from the group consisting of an α-amylase gene and a glucoamylase gene.

48. The process of claim 47, wherein the sequence encoding an amino terminal portion of a highly expressed endogenous gene the product of which is secreted from Aspergillus cells is selected from an *A. oryzae* α-amylase gene.

49. The process of claim 47, wherein the sequence encoding an amino terminal portion of a highly expressed endogenous gene the product of which is secreted from Aspergillus cells is selected from an *A. awamori* glucoamylase gene.

50. The process of claim 37, wherein the plasmid further comprises a transcription termination sequence and a selectable marker gene.

51. The process of claim 50, wherein said transcription termination sequence is selected from the group of genes consisting of an α-amylase gene, a glucoamylase gene, an alcohol dehydrogenase gene, and a benA gene.

52. The process of claim 51, wherein the transcription termination sequence is selected from an *A. niger* glucoamylase gene.

53. The process of claim 50, wherein the selectable marker gene is selected from the group of genes consisting of a pyr4 gene, a pyrG gene, an amdS gene, an argB gene, a trpC gene, and a phleomycin resistance gene.

54. The process of claim 53, wherein the selectable marker gene is the phleomycin resistance gene.

55. A process for producing a mature, native, lactoferrin, an iron-binding lobe of a native lactoferrin, or an antimicrobial peptide of a native lactoferrin which comprises culturing a transformed *Aspergillas niger* fungal cell containing a recombinant plasmid, wherein said plasmid comprises the following components operably linked from 5' to 3':

(a) a promoter from *A. niger* glucoamylase gene;

(b) a signal peptide-encoding sequence from the *A. niger* glucoamylase gene;

(c) a sequence encoding an amino terminal of the *A. niger* glucoamylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene; wherein said transformed *Aspergillus niger* fungal cell is cultured in a suitable nutrient medium until the mature, native, lactoferrin, the iron-binding lobe of a native lactoferrin, or the antimicrobial peptide of a native lactoferrin is produced as a fusion product and then processed via an endogenous proteolytic enzyme specific for said linker sequence, wherein the processed mature, native, lactoferrin, the processed iron-binding lobe of a native lactoferrin, or the processed antimicrobial peptide of a native lactoferrin is secreted into the nutrient medium and isolated therefrom.

56. A process for producing lactoferrin which comprises culturing a transformed *Aspergillus oryzae* fungal cell containing a recombinant plasmid, wherein said plasmid comprises the following components operably linked from 5' to 3':

(a) a promoter from *A. oryzae* α-amylase gene;

(b) a signal peptide-encoding sequence from the *A. oryzae* α-amylase gene;

(c) a sequence encoding an amino terminal portion of the *A. oryzae* α-amylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene; wherein said transformed *Aspergillus oryzae* fungal cell is cultured in a suitable nutrient medium until the mature, native, lactoferrin, the iron-binding lobe of a native lactoferrin, or the antimicrobial peptide of a native lactoferrin is produced as a fusion product and then processed via an endogenous proteolytic enzyme specific for said linker sequence, wherein the processed mature, native, lactoferrin, the processed iron-binding lobe of a native lactoferrin, or the processed antimicrobial peptide of a native lactoferrin is secreted into the nutrient medium and isolated therefrom.

57. A process for producing lactoferrin which comprises culturing a transformed *Aspergillus awamori* fungal cell containing a recombinant plasmid, wherein said plasmid comprises the following components operably linked from 5' to 3':

(a) a promoter from *A. awamori* glucoamylase gene;

(b) a signal peptide-encoding sequence from the *A. awamori* glucoamylase gene;

(c) a sequence encoding an amino terminal portion of the *A. awamori* glucoamylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, human lactoferrin, a nucleotide sequence encoding an iron-binding lobe of a native human lactoferrin and a nucleotide sequence encoding an antimicrobial peptide of a native human lactoferrin;

(f) a transcription termination sequence from the *A. niger* glucoamylase gene; and (g) a phleomycin resistance selectable marker gene; wherein said transformed *Aspergillus awamori* fungal cell is cultured in a suitable nutrient medium until the human lactoferrin, the iron-binding lobe of a native human lactoferrin or the antimicrobial peptide of a native human lactoferrin is produced as a fusion product and then processed via an endogenous proteolytic enzyme specific for said linker sequence, wherein the processed mature, native, human lactoferrin, the processed iron-binding lobe of native human lactoferrin, or the processed antimicrobial peptide of a native human lactoferrin is secreted into the nutrient medium and isolated therefrom.

58. A method of isolating a mature, native, lactoferrin, an iron-binding lobe of a native lactoferrin, or an antimicrobial peptide of a native lactoferrin from fungal nutrient medium comprising culturing a transformed *Aspergillus awamori* fungal cell containing a recombinant plasmid vector, wherein said plasmid vector comprises a promoter from *A. awamori* glucoamylase gene, a signal peptide-encoding sequence from the *A. awamori* glucoamylase gene, a sequence encoding an amino terminal of the *A. awamori* glucoamylase gene, a sequence encoding a peptide linker comprising a Kex2 peptidase cleavage site whereby there is an endogenous proteolytic enzyme is specific for said linker sequence, a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin, a transcription termination sequence from the *A. niger* glucoamylase gene, and a phleomycin resistance selectable marker gene and wherein said transformed *Aspergillus awamori* fungal cells are cultured in a suitable nutrient medium until the mature, native, lactoferrin, the iron-binding lobe of a native lactoferrin, or the antimicrobial peptide of a native lactoferrin is produced as a fusion product and then processed via an endogenous proteolytic enzyme specific for said linker sequence, wherein the processed mature, native, lactoferrin, the processed iron-binding lobe of a native lactoferrin, or the processed antimicrobial peptide of a native lactoferrin is secreted into the nutrient medium and isolated therefrom.

59. A mature, native, lactoferrin, an iron-binding lobe of a native lactoferrin, or an antimicrobial peptide of a native lactoferrin produced when the plasmid DNA sequence of claim 1, is transformed into an Aspergillus fungal cell, and the transformed Aspergillus fungal cell is grown under conditions suitable for expression of the mature, native, lactoferrin, the iron-binding lobe of a native lactoferrin, or the antimicrobial peptide of a native lactoferrin.

60. An antimicrobial peptide of a native lactoferrin produced when the plasmid DNA sequence of claim 1 is transformed into an Aspergillus fungal cell and the transformed Aspergillus fungal cell is grown under conditions suitable for expression of the antimicrobial peptide of a native lactoferrin, wherein said antimicrobial peptide comprises an iron-binding domain.

61. A mature, native, lactoferrin, an iron binding lobe of a native lactoferrin polypeptide, or an antimicrobial peptide of a native lactoferrin produced when the plasmid DNA sequence of claim 19, is used to transform an Aspergillus fungal cell, and the transformed Aspergillus fungal cell is grown under conditions suitable for expression of the lactoferrin.

62. An antimicrobial peptide of a native lactoferrin produced when the plasmid DNA sequence of claim 19 is transformed into an Aspergillus fungal cell, and the transformed Aspergillus fungal cell is grown under conditions suitable for expression of the antimicrobial peptide of a native lactoferrin, wherein said antimicrobial peptide comprises an iron-binding domain.

63. A mature, native, lactoferrin, an iron binding lobe of a native lactoferrin polypeptide, or an antimicrobial peptide of a native lactoferrin produced and processed when the vector of claim 31 is used to transform an *Aspergillus awamori* fungal cell, and the transformed *Aspergillus awamori* fungal cell is grown under conditions suitable for expression of the lactoferrin.

64. An antimicrobial peptide of a native lactoferrin produced when the plasmid DNA sequence of claim 31 is transformed into an *Aspergillus awamori* fungal cell, and the transformed *Aspergillus awamori* fungal cell is grown under conditions suitable for expression of the antimicrobial peptide of a native lactoferrin, wherein said antimicrobial peptide comprises an iron-binding domain.

65. A mature, native, lactoferrin, an iron binding lobe of a native lactoferrin polypeptide, or an antimicrobial peptide of a native lactoferrin produced and processed when the vector of claim 30 is used to transform an *A. oryzae* fungal cell, and the transformed *A. oryzae* fungal cell is grown under conditions suitable for expression of the lactoferrin.

66. An antimicrobial peptide of a native lactoferrin produced when the plasmid DNA sequence of claim 30 is transformed into an *Aspergillus oryzae* fungal cell, and the transformed *Aspergillus oryzae* fungal cell is grown under conditions suitable for expression of the antimicrobial peptide of a native lactoferrin, wherein said antimicrobial peptide comprises an iron-binding domain.

67. A mature, native, lactoferrin, an iron binding lobe of a native lactoferrin polypeptide, or an antimicrobial peptide of a native lactoferrin produced by the process of claim 36.

68. An antimicrobial peptide of a native lactoferrin produced by the process of claim 36, wherein said antimicrobial peptide comprises an iron-binding domain.

69. A mature, native, lactoferrin, an iron binding lobe of a native lactoferrin polypeptide, or an antimicrobial peptide of a native lactoferrin produced by the process of claim 37.

70. An antimicrobial peptide of a native lactoferrin produced by the process of claim 37, wherein said antimicrobial peptide comprises an iron-binding domain.

71. The mature, native, lactoferrin, the iron binding lobe of a native lactoferrin polypeptide, or the antimicrobial peptide of a native lactoferrin of claim 69, wherein the lactoferrin is selected from the group consisting of human lactoferrin, bovine lactoferrin and porcine lactoferrin.

72. An antimicrobial peptide of a native lactoferrin of claim 69, wherein the lactoferrin is selected from the group consisting of human lactoferrin, bovine lactoferrin and porcine lactoferrin and wherein said antimicrobial peptide comprises an iron-binding domain.

73. A mature, native, lactoferrin, an iron-binding lobe of a native lactoferrin, or an antimicrobial peptide of native lactoferrin produced by a process which comprises culturing a transformed *Aspergillas awamori* fungal cell containing a recombinant plasmid, wherein said plasmid comprises the following components operably linked from 5' to 3':

(a) a promoter from *A. awamori* glucoamylase gene;

(b) a signal peptide-encoding sequence from the *A. awamori* glucoamylase gene;

(c) a sequence encoding an amino terminal portion of the *A. awamori* glucoamylase gene;

(d) a sequence encoding a peptide linker comprising a Kex2 peptidase cleavage site whereby there is an endogenous proteolytic enzyme specific for said linker sequence;

(e) a nucleotide sequence selected from the group consisting of a nucleotide sequence encoding a mature, native, lactoferrin, a nucleotide sequence encoding an iron-binding lobe of a native lactoferrin and a nucleotide sequence encoding an antimicrobial peptide of a native lactoferrin;

(f) a transcription termination sequence from the *A. niger* glucoamylase gene; and (g) a phleomycin resistance selectable marker gene;

wherein said transformed *Aspergillus awamori* fungal cell is cultured in a suitable nutrient medium until the mature, native, lactoferrin, the iron-binding lobe of a native lactoferrin, or the antimicrobial peptide of a native lactoferrin is produced as a fusion product and then processed via an endogenous proteolytic enzyme specific for said linker sequence, wherein the processed mature, native, lactoferrin, the processed iron-binding lobe of a native lactoferrin, or the processed antimicrobial peptide of a native lactoferrin is secreted into the nutrient medium and isolated therefrom.

74. An antimicrobial peptide of a native lactoferrin of claim 73, wherein said antimicrobial peptide comprises an iron-binding domain.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:1:

GGGGTACCGC GCCGGCCGTA GGAGAAGGAG TG                                  32

( 2 ) INFORMATION FOR SEQ ID NO:2:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:2:

TTCGGTCCCG TAGACTTCCG CCGCT                                          25

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:3:

TATGCAGAGG AGCTCTCCCC TGAC                                           24

( 2 ) INFORMATION FOR SEQ ID NO:4:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:4:

GATTCCGCCG GCCAACCCTG TGCAGACGAG GC                                  32

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:5:

GAATTTCAAG CTAGATGCT                                                 19

( 2 ) INFORMATION FOR SEQ ID NO:6:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:6:

AGCGTGACCT CGACCAGCAA GAATGTGATT TCCAAGCGC                                         39

( 2 ) INFORMATION FOR SEQ ID NO:7:

( i ) SEQUENCE CHARACTERISTICS:
        ( A ) LENGTH: 39 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:7:

TCGCACTGGA GCTGGTCGTT CTTACACTAA AGGTTCGCG                                         39

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i i ) HYPOTHETICAL: NO ( i v ) ANTI-SENSE: NO ( x i ) SEQUENCE DESCRIPTION: SEQ ID NO:8:

AGCGCGGCCG CAGGAGAAGG A                                                            21